US012409032B2

United States Patent
Reich et al.

(10) Patent No.: US 12,409,032 B2
(45) Date of Patent: *Sep. 9, 2025

(54) PERCUTANEOUS IMPLANTATION OF AN ANNULOPLASTY STRUCTURE

(71) Applicant: Edwards Lifesciences Innovation (Israel) Ltd., Caesarea (IL)

(72) Inventors: Tal Reich, Moledet (IL); Amir Gross, Tel Aviv-Jaffa (IL); Tal Sheps, Givat Shmuel (IL)

(73) Assignee: Edwards Lifesciences Innovation (Israel) Ltd., Caesarea (IL)

( * ) Notice: Subject to any disclaimer, the term of this patent is extended or adjusted under 35 U.S.C. 154(b) by 934 days.

This patent is subject to a terminal disclaimer.

(21) Appl. No.: 17/063,549

(22) Filed: Oct. 5, 2020

(65) Prior Publication Data

US 2021/0015617 A1   Jan. 21, 2021

Related U.S. Application Data

(60) Continuation of application No. 15/919,452, filed on Mar. 13, 2018, now Pat. No. 10,792,152, which is a
(Continued)

(51) Int. Cl.
*A61F 2/24* (2006.01)
*A61B 17/00* (2006.01)
(Continued)

(52) U.S. Cl.
CPC .......... *A61F 2/2445* (2013.01); *A61F 2/2466* (2013.01); *A61B 2017/00243* (2013.01);
(Continued)

(58) Field of Classification Search
None
See application file for complete search history.

(56) References Cited

U.S. PATENT DOCUMENTS 3,604,488 A   9/1971   Wishart et al.
3,656,185 A   4/1972   Carpentier
(Continued)

FOREIGN PATENT DOCUMENTS

CA   2728078 A1 *  1/2010  ........... A61F 2/2442
CN   113331995 A    9/2021
(Continued)

OTHER PUBLICATIONS

Agarwal et al. International Cardiology Perspective Functional Tricuspid Regurgitation, Circ Cardiovasc Interv 2009;2;2;565-573 (2009).
(Continued)

*Primary Examiner* — Leslie A Lopez
(74) *Attorney, Agent, or Firm* — Anya Adams

(57) ABSTRACT

During a percutaneous transcatheter procedure, an annuloplasty structure is secured at least partially around an annulus of a mitral valve of a subject by coupling a plurality of tissue anchors to the annulus such that (i) a longitudinal contracting member of the annuloplasty structure extends at least partially around the annulus, and (ii) the plurality of tissue anchors is distributed at least partially around the annulus. A longitudinal density of the anchors along a middle scallop of a posterior leaflet of the mitral valve is at least twice as great as a longitudinal density of the anchors along a lateral scallop of the posterior leaflet, and/or at least twice as great as a longitudinal density of the anchors along a medial scallop of the posterior leaflet. Thereafter, at least
(Continued)

part of the annulus is contracted by contracting a longitudinal portion of the annuloplasty structure by tightening the longitudinal contracting member.

29 Claims, 37 Drawing Sheets

Related U.S. Application Data continuation-in-part of application No. 15/474,543, filed on Mar. 30, 2017, now Pat. No. 10,470,882, and a division of application No. 14/589,100, filed on Jan. 5, 2015, now Pat. No. 9,918,840, said application No. 15/474,543 is a continuation of application No. 14/128,756, filed as application No. PCT/IL2012/000250 on Jun. 21, 2012, now Pat. No. 9,662,209, which is a continuation-in-part of application No. 13/167,444, filed on Jun. 23, 2011, now Pat. No. 9,011,530, and a continuation-in-part of application No. 13/167,476, filed on Jun. 23, 2011, now Pat. No. 8,940,044, and a continuation-in-part of application No. 13/167,492, filed on Jun. 23, 2011, now Pat. No. 8,926,697.

(51) Int. Cl.
*A61B 17/04* (2006.01)
*A61B 17/34* (2006.01)

(52) U.S. Cl.
CPC ............... *A61B 2017/0441* (2013.01); *A61B 2017/0464* (2013.01); *A61B 17/3468* (2013.01); *A61F 2/2448* (2013.01); *A61F 2220/0008* (2013.01); *A61F 2250/001* (2013.01)

(56) References Cited

U.S. PATENT DOCUMENTS

| | | | |
|---|---|---|---|
| 3,840,018 A | 10/1974 | Heifetz |
| 3,881,366 A | 5/1975 | Bradley et al. |
| 3,898,701 A | 8/1975 | La Russa |
| 4,042,979 A | 8/1977 | Angell |
| 4,118,805 A | 10/1978 | Reimels |
| 4,214,349 A | 7/1980 | Munch |
| 4,261,342 A | 4/1981 | Aranguren Duo |
| 4,290,151 A | 9/1981 | Massana |
| 4,434,828 A | 3/1984 | Trincia |
| 4,473,928 A | 10/1984 | Johnson |
| 4,602,911 A | 7/1986 | Ahmadi et al. |
| 4,625,727 A | 12/1986 | Leiboff |
| 4,712,549 A | 12/1987 | Peters et al. |
| 4,778,468 A | 10/1988 | Hunt et al. |
| 4,917,698 A | 4/1990 | Carpentier et al. |
| 4,935,027 A | 6/1990 | Yoon |
| 4,961,738 A | 10/1990 | Mackin |
| 5,042,707 A | 8/1991 | Taheri |
| 5,061,277 A | 10/1991 | Carpentier et al. |
| 5,064,431 A | 11/1991 | Gilbertson et al. |
| 5,104,407 A | 4/1992 | Lam et al. |
| 5,108,420 A | 4/1992 | Marks |
| 5,201,880 A | 4/1993 | Wright et al. |
| 5,258,008 A | 11/1993 | Wilk |
| 5,300,034 A | 4/1994 | Behnke et al. |
| 5,306,296 A | 4/1994 | Wright et al. |
| 5,325,845 A | 7/1994 | Adair |
| 5,346,498 A | 9/1994 | Greelis et al. |
| 5,383,852 A | 1/1995 | Stevens-Wright |
| 5,449,368 A | 9/1995 | Kuzmak |
| 5,450,860 A | 9/1995 | O'Connor |
| 5,464,404 A | 11/1995 | Abela et al. |
| 5,474,518 A | 12/1995 | Farrer Velazquez |
| 5,477,856 A | 12/1995 | Lundquist |
| 5,501,683 A | 3/1996 | Trott |
| 5,593,424 A | 1/1997 | Northrup, III |
| 5,601,572 A | 2/1997 | Middleman et al. |
| 5,626,609 A | 5/1997 | Zvenyatsky et al. |
| 5,643,317 A | 7/1997 | Pavcnik et al. |
| 5,669,919 A | 9/1997 | Sanders et al. |
| 5,674,279 A | 10/1997 | Wright et al. |
| 5,676,653 A | 10/1997 | Taylor et al. |
| 5,683,402 A | 11/1997 | Cosgrove et al. |
| 5,702,397 A | 12/1997 | Goble et al. |
| 5,702,398 A | 12/1997 | Tarabishy |
| 5,709,695 A | 1/1998 | Northrup, III |
| 5,716,370 A | 2/1998 | Williamson, IV et al. |
| 5,716,397 A | 2/1998 | Myers |
| 5,728,116 A | 3/1998 | Rosenman |
| 5,730,150 A | 3/1998 | Peppel et al. |
| 5,749,371 A | 5/1998 | Zadini et al. |
| 5,752,963 A | 5/1998 | Allard et al. |
| 5,782,844 A | 7/1998 | Yoon et al. |
| 5,782,862 A | 7/1998 | Bonutti |
| 5,810,882 A | 9/1998 | Bolduc et al. |
| 5,824,066 A | 10/1998 | Gross |
| 5,830,221 A | 11/1998 | Stein et al. |
| 5,843,120 A | 12/1998 | Israel et al. |
| 5,855,614 A | 1/1999 | Stevens et al. |
| 5,876,373 A | 3/1999 | Giba et al. |
| 5,935,098 A | 8/1999 | Blaisdell et al. |
| 5,957,953 A | 9/1999 | DiPoto et al. |
| 5,961,440 A | 10/1999 | Schweich, Jr. et al. |
| 5,961,539 A | 10/1999 | Northrup, III et al. |
| 5,984,959 A | 11/1999 | Robertson et al. |
| 5,993,459 A | 11/1999 | Larsen et al. |
| 6,042,554 A | 3/2000 | Rosenman et al. |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,074,341 A | 6/2000 | Anderson et al. |
| 6,074,401 A | 6/2000 | Gardiner et al. |
| 6,074,417 A | 6/2000 | Peredo |
| 6,086,582 A | 7/2000 | Altman et al. |
| 6,102,945 A | 8/2000 | Campbell |
| 6,106,550 A | 8/2000 | Magovern et al. |
| 6,110,200 A | 8/2000 | Hinnenkamp |
| 6,132,390 A | 10/2000 | Cookston et al. |
| 6,143,024 A | 11/2000 | Campbell et al. |
| 6,159,240 A | 12/2000 | Sparer et al. |
| 6,165,119 A | 12/2000 | Schweich, Jr. et al. |
| 6,174,332 B1 | 1/2001 | Loch et al. |
| 6,183,411 B1 | 2/2001 | Mortier et al. |
| 6,187,040 B1 | 2/2001 | Wright |
| 6,210,347 B1 | 4/2001 | Forsell |
| 6,217,610 B1 | 4/2001 | Carpentier et al. |
| 6,228,032 B1 | 5/2001 | Eaton et al. |
| 6,231,602 B1 | 5/2001 | Carpentier et al. |
| 6,251,092 B1 | 6/2001 | Qin et al. |
| 6,296,656 B1 | 10/2001 | Bolduc et al. |
| 6,315,784 B1 | 11/2001 | Djurovic |
| 6,319,281 B1 | 11/2001 | Patel |
| 6,328,746 B1 | 12/2001 | Gambale |
| 6,332,893 B1 | 12/2001 | Mortier et al. |
| 6,355,030 B1 | 3/2002 | Aldrich et al. |
| 6,361,559 B1 | 3/2002 | Houser et al. |
| 6,368,348 B1 | 4/2002 | Gabbay |
| 6,402,780 B2 | 6/2002 | Williamson, IV et al. |
| 6,406,420 B1 | 6/2002 | McCarthy et al. |
| 6,406,493 B1 | 6/2002 | Tu et al. |
| 6,419,696 B1 | 7/2002 | Ortiz et al. |
| 6,451,054 B1 | 9/2002 | Stevens |
| 6,458,076 B1 | 10/2002 | Pruitt |
| 6,461,336 B1 | 10/2002 | Larre |
| 6,461,366 B1 | 10/2002 | Seguin |
| 6,470,892 B1 | 10/2002 | Forsell |
| 6,503,274 B1 | 1/2003 | Howanec, Jr. et al. |
| 6,524,338 B1 | 2/2003 | Gundry |
| 6,527,780 B1 | 3/2003 | Wallace et al. |
| 6,530,952 B2 | 3/2003 | Vesely |
| 6,533,772 B1 | 3/2003 | Sherts et al. |
| 6,537,314 B2 | 3/2003 | Langberg et al. |

(56) References Cited

U.S. PATENT DOCUMENTS

| | | |
|---|---|---|
| 6,547,801 B1 | 4/2003 | Dargent et al. |
| 6,554,845 B1 | 4/2003 | Fleenor et al. |
| 6,564,805 B2 | 5/2003 | Garrison et al. |
| 6,565,603 B2 | 5/2003 | Cox |
| 6,569,198 B1 | 5/2003 | Wilson et al. |
| 6,579,297 B2 | 6/2003 | Bicek et al. |
| 6,589,160 B2 | 7/2003 | Schweich, Jr. et al. |
| 6,592,593 B1 | 7/2003 | Parodi et al. |
| 6,602,288 B1 | 8/2003 | Cosgrove et al. |
| 6,602,289 B1 | 8/2003 | Colvin et al. |
| 6,613,078 B1 | 9/2003 | Barone |
| 6,613,079 B1 | 9/2003 | Wolinsky et al. |
| 6,619,291 B1 | 9/2003 | Hlavka et al. |
| 6,626,899 B2 | 9/2003 | Houser et al. |
| 6,626,917 B1 | 9/2003 | Craig |
| 6,626,930 B1 | 9/2003 | Allen et al. |
| 6,629,534 B1 | 10/2003 | St. Goar et al. |
| 6,629,921 B1 | 10/2003 | Schweich, Jr. et al. |
| 6,651,671 B1 | 11/2003 | Donlon et al. |
| 6,652,556 B1 | 11/2003 | VanTassel et al. |
| 6,682,558 B2 | 1/2004 | Tu et al. |
| 6,689,125 B1 | 2/2004 | Keith et al. |
| 6,689,164 B1 | 2/2004 | Seguin |
| 6,695,866 B1 | 2/2004 | Kuehn et al. |
| 6,702,826 B2 | 3/2004 | Liddicoat et al. |
| 6,702,846 B2 | 3/2004 | Mikus et al. |
| 6,706,065 B2 | 3/2004 | Langberg et al. |
| 6,709,385 B2 | 3/2004 | Forsell |
| 6,709,456 B2 | 3/2004 | Langberg et al. |
| 6,711,444 B2 | 3/2004 | Koblish |
| 6,719,786 B2 | 4/2004 | Ryan et al. |
| 6,723,038 B1 | 4/2004 | Schroeder et al. |
| 6,726,716 B2 | 4/2004 | Marquez |
| 6,726,717 B2 | 4/2004 | Alfieri et al. |
| 6,730,121 B2 | 5/2004 | Ortiz et al. |
| 6,749,630 B2 | 6/2004 | McCarthy et al. |
| 6,752,813 B2 | 6/2004 | Goldfarb et al. |
| 6,764,310 B1 | 7/2004 | Ichihashi et al. |
| 6,764,510 B2 | 7/2004 | Vidlund et al. |
| 6,764,810 B2 | 7/2004 | Ma et al. |
| 6,770,083 B2 | 8/2004 | Seguin |
| 6,786,924 B2 | 9/2004 | Ryan et al. |
| 6,786,925 B1 | 9/2004 | Schoon et al. |
| 6,790,231 B2 | 9/2004 | Liddicoat et al. |
| 6,797,001 B2 | 9/2004 | Mathis et al. |
| 6,797,002 B2 | 9/2004 | Spence et al. |
| 6,802,319 B2 | 10/2004 | Stevens et al. |
| 6,805,710 B2 | 10/2004 | Bolling et al. |
| 6,805,711 B2 | 10/2004 | Quijano et al. |
| 6,855,126 B2 | 2/2005 | Flinchbaugh |
| 6,858,039 B2 | 2/2005 | McCarthy |
| 6,884,250 B2 | 4/2005 | Monassevitch et al. |
| 6,893,459 B1 | 5/2005 | Macoviak |
| 6,908,478 B2 | 6/2005 | Alferness et al. |
| 6,908,482 B2 | 6/2005 | McCarthy et al. |
| 6,918,917 B1 | 7/2005 | Nguyen et al. |
| 6,926,730 B1 | 8/2005 | Nguyen et al. |
| 6,960,217 B2 | 11/2005 | Bolduc |
| 6,964,684 B2 | 11/2005 | Ortiz et al. |
| 6,964,686 B2 | 11/2005 | Gordon |
| 6,976,995 B2 | 12/2005 | Mathis et al. |
| 6,986,775 B2 | 1/2006 | Morales et al. |
| 6,989,028 B2 | 1/2006 | Lashinski et al. |
| 6,997,951 B2 | 2/2006 | Solem et al. |
| 7,004,176 B2 | 2/2006 | Lau |
| 7,007,798 B2 | 3/2006 | Happonen et al. |
| 7,011,669 B2 | 3/2006 | Kimblad |
| 7,011,682 B2 | 3/2006 | Lashinski et al. |
| 7,018,406 B2 | 3/2006 | Seguin et al. |
| 7,037,334 B1 | 5/2006 | Hlavka et al. |
| 7,077,850 B2 | 7/2006 | Kortenbach |
| 7,077,862 B2 | 7/2006 | Vidlund et al. |
| 7,087,064 B1 | 8/2006 | Hyde |
| 7,101,395 B2 | 9/2006 | Tremulis et al. |
| 7,101,396 B2 | 9/2006 | Artof et al. |
| 7,112,207 B2 | 9/2006 | Allen et al. |
| 7,118,595 B2 | 10/2006 | Ryan et al. |
| 7,125,421 B2 | 10/2006 | Tremulis et al. |
| 7,150,737 B2 | 12/2006 | Purdy et al. |
| 7,159,593 B2 | 1/2007 | McCarthy et al. |
| 7,166,127 B2 | 1/2007 | Spence et al. |
| 7,169,187 B2 | 1/2007 | Datta et al. |
| 7,172,625 B2 | 2/2007 | Shu et al. |
| 7,175,660 B2 | 2/2007 | Cartledge et al. |
| 7,186,262 B2 | 3/2007 | Saadat |
| 7,186,264 B2 | 3/2007 | Liddicoat et al. |
| 7,189,199 B2 | 3/2007 | McCarthy et al. |
| 7,192,443 B2 | 3/2007 | Solem et al. |
| 7,220,277 B2 | 5/2007 | Arru et al. |
| 7,226,467 B2 | 6/2007 | Lucatero et al. |
| 7,226,477 B2 | 6/2007 | Cox |
| 7,226,647 B2 | 6/2007 | Kasperchik et al. |
| 7,229,452 B2 | 6/2007 | Kayan |
| 7,238,191 B2 | 7/2007 | Bachmann |
| 7,288,097 B2 | 10/2007 | Seguin |
| 7,294,148 B2 | 11/2007 | McCarthy |
| 7,311,728 B2 | 12/2007 | Solem et al. |
| 7,311,729 B2 | 12/2007 | Mathis et al. |
| 7,314,485 B2 | 1/2008 | Mathis |
| 7,316,710 B1 | 1/2008 | Cheng et al. |
| 7,329,279 B2 | 2/2008 | Haug et al. |
| 7,329,280 B2 | 2/2008 | Bolling et al. |
| 7,335,213 B1 | 2/2008 | Hyde et al. |
| 7,361,190 B2 | 4/2008 | Shaoulian et al. |
| 7,364,588 B2 | 4/2008 | Mathis et al. |
| 7,377,941 B2 | 5/2008 | Rhee et al. |
| 7,390,329 B2 | 6/2008 | Westra et al. |
| 7,404,824 B1 | 7/2008 | Webler et al. |
| 7,431,692 B2 | 10/2008 | Zollinger et al. |
| 7,442,207 B2 | 10/2008 | Rafiee |
| 7,452,376 B2 | 11/2008 | Lim et al. |
| 7,455,690 B2 | 11/2008 | Cartledge et al. |
| 7,485,142 B2 | 2/2009 | Milo |
| 7,485,143 B2 | 2/2009 | Webler et al. |
| 7,500,989 B2 | 3/2009 | Solem et al. |
| 7,507,252 B2 | 3/2009 | Lashinski et al. |
| 7,510,575 B2 | 3/2009 | Spenser et al. |
| 7,510,577 B2 | 3/2009 | Moaddeb et al. |
| 7,527,647 B2 | 5/2009 | Spence |
| 7,530,995 B2 | 5/2009 | Quijano et al. |
| 7,549,983 B2 | 6/2009 | Roue et al. |
| 7,559,936 B2 | 7/2009 | Levine |
| 7,562,660 B2 | 7/2009 | Saadat |
| 7,563,267 B2 | 7/2009 | Goldfarb et al. |
| 7,563,273 B2 | 7/2009 | Goldfarb et al. |
| 7,569,062 B1 | 8/2009 | Kuehn et al. |
| 7,585,321 B2 | 9/2009 | Cribier |
| 7,588,582 B2 | 9/2009 | Starksen et al. |
| 7,591,826 B2 | 9/2009 | Alferness et al. |
| 7,604,646 B2 | 10/2009 | Goldfarb et al. |
| 7,608,091 B2 | 10/2009 | Goldfarb et al. |
| 7,608,103 B2 | 10/2009 | McCarthy |
| 7,618,449 B2 | 11/2009 | Tremulis et al. |
| 7,625,403 B2 | 12/2009 | Krivoruchko |
| 7,632,303 B1 | 12/2009 | Stalker et al. |
| 7,635,329 B2 | 12/2009 | Goldfarb et al. |
| 7,635,386 B1 | 12/2009 | Gammie |
| 7,655,015 B2 | 2/2010 | Goldfarb et al. |
| 7,666,204 B2 | 2/2010 | Thornton et al. |
| 7,682,319 B2 | 3/2010 | Martin et al. |
| 7,682,369 B2 | 3/2010 | Seguin |
| 7,686,822 B2 | 3/2010 | Shayani |
| 7,699,892 B2 | 4/2010 | Rafiee et al. |
| 7,704,269 B2 | 4/2010 | St. Goar et al. |
| 7,704,277 B2 | 4/2010 | Zakay et al. |
| 7,722,666 B2 | 5/2010 | Lafontaine |
| 7,736,388 B2 | 6/2010 | Goldfarb et al. |
| 7,748,389 B2 | 7/2010 | Salahieh et al. |
| 7,753,924 B2 | 7/2010 | Starksen et al. |
| 7,758,632 B2 | 7/2010 | Hojeibane et al. |
| 7,780,726 B2 | 8/2010 | Seguin |
| 7,871,368 B2 | 1/2011 | Zollinger et al. |
| 7,871,433 B2 | 1/2011 | Lattouf |
| 7,883,475 B2 | 2/2011 | Dupont et al. |

(56) References Cited

U.S. PATENT DOCUMENTS

| | | |
|---|---|---|
| 7,883,538 B2 | 2/2011 | To et al. |
| 7,892,281 B2 | 2/2011 | Seguin et al. |
| 7,927,370 B2 | 4/2011 | Webler et al. |
| 7,927,371 B2 | 4/2011 | Navia et al. |
| 7,942,927 B2 | 5/2011 | Kaye et al. |
| 7,947,056 B2 | 5/2011 | Griego et al. |
| 7,955,315 B2 | 6/2011 | Feinberg et al. |
| 7,955,377 B2 | 6/2011 | Melsheimer |
| 7,981,152 B1 | 7/2011 | Webler et al. |
| 7,992,567 B2 | 8/2011 | Hirotsuka et al. |
| 7,993,368 B2 | 8/2011 | Gambale et al. |
| 7,993,397 B2 | 8/2011 | Lashinski et al. |
| 8,012,201 B2 | 9/2011 | Lashinski et al. |
| 8,034,103 B2 | 10/2011 | Burriesci et al. |
| 8,052,592 B2 | 11/2011 | Goldfarb et al. |
| 8,057,493 B2 | 11/2011 | Goldfarb et al. |
| 8,062,355 B2 | 11/2011 | Figulla et al. |
| 8,070,804 B2 | 12/2011 | Hyde et al. |
| 8,070,805 B2 | 12/2011 | Vidlund et al. |
| 8,075,616 B2 | 12/2011 | Solem et al. |
| 8,100,964 B2 | 1/2012 | Spence |
| 8,123,801 B2 | 2/2012 | Milo |
| 8,142,493 B2 | 3/2012 | Spence et al. |
| 8,142,495 B2 | 3/2012 | Hasenkam et al. |
| 8,142,496 B2 | 3/2012 | Berreklouw |
| 8,147,542 B2 | 4/2012 | Maisano et al. |
| 8,152,844 B2 | 4/2012 | Rao et al. |
| 8,163,013 B2 | 4/2012 | Machold et al. |
| 8,187,299 B2 | 5/2012 | Goldfarb et al. |
| 8,187,324 B2 | 5/2012 | Webler et al. |
| 8,202,315 B2 | 6/2012 | Hlavka et al. |
| 8,206,439 B2 | 6/2012 | Gomez Duran |
| 8,216,302 B2 | 7/2012 | Wilson et al. |
| 8,231,671 B2 | 7/2012 | Kim |
| 8,262,725 B2 | 9/2012 | Subramanian |
| 8,265,758 B2 | 9/2012 | Policker et al. |
| 8,277,502 B2 | 10/2012 | Miller et al. |
| 8,287,584 B2 | 10/2012 | Salahieh et al. |
| 8,287,591 B2 | 10/2012 | Keidar et al. |
| 8,292,884 B2 | 10/2012 | Levine et al. |
| 8,303,608 B2 | 11/2012 | Goldfarb et al. |
| 8,323,334 B2 | 12/2012 | Deem et al. |
| 8,328,868 B2 | 12/2012 | Paul et al. |
| 8,333,777 B2 | 12/2012 | Schaller et al. |
| 8,343,173 B2 | 1/2013 | Starksen et al. |
| 8,343,174 B2 | 1/2013 | Goldfarb et al. |
| 8,343,213 B2 | 1/2013 | Salahieh et al. |
| 8,349,002 B2 | 1/2013 | Milo |
| 8,353,956 B2 | 1/2013 | Miller et al. |
| 8,357,195 B2 | 1/2013 | Kuehn |
| 8,382,829 B1 | 2/2013 | Call et al. |
| 8,388,680 B2 | 3/2013 | Starksen et al. |
| 8,393,517 B2 | 3/2013 | Milo |
| 8,419,825 B2 | 4/2013 | Burgler et al. |
| 8,430,926 B2 | 4/2013 | Kirson |
| 8,449,573 B2 | 5/2013 | Chu |
| 8,449,599 B2 | 5/2013 | Chau et al. |
| 8,454,686 B2 | 6/2013 | Alkhatib |
| 8,460,370 B2 | 6/2013 | Zakay |
| 8,460,371 B2 | 6/2013 | Hlavka et al. |
| 8,475,491 B2 | 7/2013 | Milo |
| 8,475,525 B2 | 7/2013 | Maisano et al. |
| 8,480,732 B2 | 7/2013 | Subramanian |
| 8,518,107 B2 | 8/2013 | Tsukashima et al. |
| 8,523,940 B2 | 9/2013 | Richardson et al. |
| 8,545,553 B2 | 10/2013 | Zipory et al. |
| 8,551,161 B2 | 10/2013 | Dolan |
| 8,585,755 B2 | 11/2013 | Chau et al. |
| 8,591,576 B2 | 11/2013 | Hasenkam et al. |
| 8,608,797 B2 | 12/2013 | Gross et al. |
| 8,628,569 B2 | 1/2014 | Benichou et al. |
| 8,628,571 B1 | 1/2014 | Hacohen et al. |
| 8,641,727 B2 | 2/2014 | Starksen et al. |
| 8,652,202 B2 | 2/2014 | Alon et al. |
| 8,652,203 B2 | 2/2014 | Quadri et al. |
| 8,679,174 B2 | 3/2014 | Ottma et al. |
| 8,685,086 B2 | 4/2014 | Navia et al. |
| 8,728,097 B1 | 5/2014 | Sugimoto et al. |
| 8,728,155 B2 | 5/2014 | Montorfano et al. |
| 8,734,467 B2 | 5/2014 | Miller et al. |
| 8,734,699 B2 | 5/2014 | Heideman et al. |
| 8,740,920 B2 | 6/2014 | Goldfarb et al. |
| 8,747,463 B2 | 6/2014 | Fogarty et al. |
| 8,778,021 B2 | 7/2014 | Cartledge |
| 8,784,481 B2 | 7/2014 | Alkhatib et al. |
| 8,790,367 B2 | 7/2014 | Nguyen et al. |
| 8,790,394 B2 | 7/2014 | Miller et al. |
| 8,795,298 B2 | 8/2014 | Hernlund et al. |
| 8,795,355 B2 | 8/2014 | Alkhatib |
| 8,795,356 B2 | 8/2014 | Quadri et al. |
| 8,795,357 B2 | 8/2014 | Yohanan et al. |
| 8,808,366 B2 | 8/2014 | Braido et al. |
| 8,808,368 B2 | 8/2014 | Maisano et al. |
| 8,845,717 B2 | 9/2014 | Khairkhahan et al. |
| 8,845,723 B2 | 9/2014 | Spence et al. |
| 8,852,261 B2 | 10/2014 | White |
| 8,852,272 B2 | 10/2014 | Gross et al. |
| 8,858,623 B2 | 10/2014 | Miller et al. |
| 8,864,822 B2 | 10/2014 | Spence et al. |
| 8,870,948 B1 | 10/2014 | Erzberger et al. |
| 8,870,949 B2 | 10/2014 | Rowe |
| 8,888,843 B2 | 11/2014 | Khairkhahan et al. |
| 8,889,861 B2 | 11/2014 | Skead et al. |
| 8,894,702 B2 | 11/2014 | Quadri et al. |
| 8,911,461 B2 | 12/2014 | Traynor et al. |
| 8,911,494 B2 | 12/2014 | Hammer et al. |
| 8,926,696 B2 | 1/2015 | Cabiri et al. |
| 8,926,697 B2 | 1/2015 | Gross et al. |
| 8,932,343 B2 | 1/2015 | Alkhatib et al. |
| 8,932,348 B2 | 1/2015 | Solem et al. |
| 8,940,044 B2 | 1/2015 | Hammer et al. |
| 8,945,211 B2 | 2/2015 | Sugimoto |
| 8,951,285 B2 | 2/2015 | Sugimoto et al. |
| 8,951,286 B2 | 2/2015 | Sugimoto et al. |
| 8,961,595 B2 | 2/2015 | Alkhatib |
| 8,961,602 B2 | 2/2015 | Kovach et al. |
| 8,979,922 B2 | 3/2015 | Jayasinghe et al. |
| 8,992,604 B2 | 3/2015 | Gross et al. |
| 9,005,273 B2 | 4/2015 | Salahieh et al. |
| 9,011,520 B2 | 4/2015 | Miller et al. |
| 9,011,530 B2 | 4/2015 | Reich et al. |
| 9,023,100 B2 | 5/2015 | Quadri et al. |
| 9,072,603 B2 | 7/2015 | Tuval et al. |
| 9,107,749 B2 | 8/2015 | Bobo et al. |
| 9,119,719 B2 | 9/2015 | Zipory et al. |
| 9,125,632 B2 | 9/2015 | Loulmet et al. |
| 9,125,742 B2 | 9/2015 | Yoganathan et al. |
| 9,138,316 B2 | 9/2015 | Bielefeld |
| 9,173,646 B2 | 11/2015 | Fabro |
| 9,180,005 B1 | 11/2015 | Lashinski et al. |
| 9,180,007 B2 | 11/2015 | Reich et al. |
| 9,192,472 B2 | 11/2015 | Gross et al. |
| 9,198,756 B2 | 12/2015 | Aklog et al. |
| 9,226,825 B2 | 1/2016 | Starksen et al. |
| 9,265,608 B2 | 2/2016 | Miller et al. |
| 9,326,857 B2 | 5/2016 | Cartledge et al. |
| 9,414,921 B2 | 8/2016 | Miller et al. |
| 9,427,316 B2 | 8/2016 | Schweich, Jr. et al. |
| 9,474,606 B2 | 10/2016 | Zipory et al. |
| 9,526,613 B2 | 12/2016 | Gross et al. |
| 9,561,104 B2 | 2/2017 | Miller et al. |
| 9,579,090 B1 | 2/2017 | Simms et al. |
| 9,693,865 B2 | 7/2017 | Gilmore et al. |
| 9,724,084 B2 | 8/2017 | Groothuis et al. |
| 9,730,793 B2 | 8/2017 | Reich et al. |
| 9,788,941 B2 | 10/2017 | Hacohen |
| 9,801,720 B2 | 10/2017 | Gilmore et al. |
| 9,907,547 B2 | 3/2018 | Gilmore et al. |
| 10,368,852 B2 | 8/2019 | Gerhardt et al. |
| 2001/0021874 A1 | 9/2001 | Carpentier et al. |
| 2002/0022862 A1 | 2/2002 | Grafton et al. |
| 2002/0042621 A1* | 4/2002 | Liddicoat ......... A61B 17/00234 606/151 |
| 2002/0082525 A1 | 6/2002 | Oslund et al. |

(56) References Cited

U.S. PATENT DOCUMENTS

| | | |
|---|---|---|
| 2002/0087048 A1 | 7/2002 | Brock et al. |
| 2002/0095139 A1 | 7/2002 | Keogh et al. |
| 2002/0103532 A1 | 8/2002 | Langberg et al. |
| 2002/0120292 A1 | 8/2002 | Morgan |
| 2002/0151916 A1 | 10/2002 | Muramatsu et al. |
| 2002/0151970 A1 | 10/2002 | Garrison et al. |
| 2002/0169358 A1 | 11/2002 | Mortier et al. |
| 2002/0177904 A1 | 11/2002 | Huxel et al. |
| 2002/0188301 A1 | 12/2002 | Dallara et al. |
| 2002/0188350 A1 | 12/2002 | Arru et al. |
| 2002/0198586 A1 | 12/2002 | Inoue |
| 2003/0018358 A1 | 1/2003 | Saadat |
| 2003/0050693 A1 | 3/2003 | Quijano et al. |
| 2003/0078465 A1 | 4/2003 | Pai et al. |
| 2003/0078653 A1 | 4/2003 | Vesely et al. |
| 2003/0083538 A1 | 5/2003 | Adams et al. |
| 2003/0093148 A1 | 5/2003 | Bolling et al. |
| 2003/0100943 A1 | 5/2003 | Bolduc |
| 2003/0105519 A1 | 6/2003 | Fasol et al. |
| 2003/0114901 A1 | 6/2003 | Loeb et al. |
| 2003/0120340 A1 | 6/2003 | Liska et al. |
| 2003/0144657 A1 | 7/2003 | Bowe et al. |
| 2003/0171760 A1 | 9/2003 | Gambale |
| 2003/0199974 A1 | 10/2003 | Lee et al. |
| 2003/0204193 A1 | 10/2003 | Gabriel et al. |
| 2003/0204195 A1 | 10/2003 | Keane et al. |
| 2003/0208208 A1 | 11/2003 | Chu |
| 2003/0229350 A1 | 12/2003 | Kay |
| 2003/0229395 A1 | 12/2003 | Cox |
| 2004/0002735 A1 | 1/2004 | Lizardi et al. |
| 2004/0010287 A1 | 1/2004 | Bonutti |
| 2004/0019359 A1 | 1/2004 | Worley et al. |
| 2004/0019377 A1 | 1/2004 | Taylor et al. |
| 2004/0024451 A1 | 2/2004 | Johnson et al. |
| 2004/0039442 A1 | 2/2004 | St. Goar et al. |
| 2004/0044350 A1 | 3/2004 | Martin et al. |
| 2004/0049211 A1 | 3/2004 | Tremulis et al. |
| 2004/0059413 A1 | 3/2004 | Argento |
| 2004/0068273 A1 | 4/2004 | Fariss et al. |
| 2004/0111095 A1 | 6/2004 | Gordon et al. |
| 2004/0122514 A1 | 6/2004 | Fogarty et al. |
| 2004/0127982 A1 | 7/2004 | Machold et al. |
| 2004/0133274 A1 | 7/2004 | Webler et al. |
| 2004/0133374 A1 | 7/2004 | Kattan |
| 2004/0138744 A1 | 7/2004 | Lashinski et al. |
| 2004/0138745 A1 | 7/2004 | Macoviak et al. |
| 2004/0148019 A1 | 7/2004 | Vidlund et al. |
| 2004/0148020 A1 | 7/2004 | Vidlund et al. |
| 2004/0148021 A1 | 7/2004 | Cartledge et al. |
| 2004/0176788 A1 | 9/2004 | Opolski |
| 2004/0181287 A1 | 9/2004 | Gellman |
| 2004/0186566 A1 | 9/2004 | Hindrichs et al. |
| 2004/0193191 A1 | 9/2004 | Starksen et al. |
| 2004/0220593 A1 | 11/2004 | Greenhalgh |
| 2004/0243227 A1 | 12/2004 | Starksen et al. |
| 2004/0260317 A1 | 12/2004 | Bloom et al. |
| 2004/0260344 A1 | 12/2004 | Lyons et al. |
| 2004/0260393 A1 | 12/2004 | Rahdert et al. |
| 2004/0260394 A1 | 12/2004 | Douk et al. |
| 2004/0267358 A1 | 12/2004 | Reitan |
| 2005/0004668 A1 | 1/2005 | Aklog et al. |
| 2005/0010287 A1 | 1/2005 | Macoviak et al. |
| 2005/0010787 A1 | 1/2005 | Tarbouriech |
| 2005/0016560 A1 | 1/2005 | Voughlohn |
| 2005/0049692 A1 | 3/2005 | Numamoto et al. |
| 2005/0055038 A1 | 3/2005 | Kelleher et al. |
| 2005/0055087 A1 | 3/2005 | Starksen |
| 2005/0060030 A1 | 3/2005 | Lashinski et al. |
| 2005/0065601 A1 | 3/2005 | Lee et al. |
| 2005/0070999 A1 | 3/2005 | Spence |
| 2005/0075654 A1 | 4/2005 | Kelleher |
| 2005/0075727 A1 | 4/2005 | Wheatley |
| 2005/0090827 A1 | 4/2005 | Gedebou |
| 2005/0090834 A1 | 4/2005 | Chiang et al. |
| 2005/0096740 A1 | 5/2005 | Langberg et al. |
| 2005/0107871 A1 | 5/2005 | Realyvasquez et al. |
| 2005/0119734 A1 | 6/2005 | Spence et al. |
| 2005/0125002 A1 | 6/2005 | Baran et al. |
| 2005/0125011 A1* | 6/2005 | Spence ............... A61F 2/2466 606/151 |
| 2005/0131533 A1 | 6/2005 | Alfieri et al. |
| 2005/0137686 A1 | 6/2005 | Salahieh et al. |
| 2005/0137688 A1 | 6/2005 | Salahieh et al. |
| 2005/0137695 A1 | 6/2005 | Salahieh et al. |
| 2005/0159728 A1 | 7/2005 | Armour et al. |
| 2005/0159810 A1 | 7/2005 | Filsoufi |
| 2005/0171601 A1 | 8/2005 | Cosgrove et al. |
| 2005/0177180 A1 | 8/2005 | Kaganov et al. |
| 2005/0177228 A1 | 8/2005 | Solem et al. |
| 2005/0187568 A1 | 8/2005 | Klenk et al. |
| 2005/0187613 A1 | 8/2005 | Bolduc et al. |
| 2005/0192596 A1 | 9/2005 | Jugenheimer et al. |
| 2005/0203549 A1 | 9/2005 | Realyvasquez |
| 2005/0203606 A1 | 9/2005 | VanCamp |
| 2005/0216039 A1 | 9/2005 | Lederman |
| 2005/0216079 A1 | 9/2005 | MaCoviak |
| 2005/0222665 A1 | 10/2005 | Aranyi |
| 2005/0234481 A1 | 10/2005 | Waller |
| 2005/0240199 A1 | 10/2005 | Martinek et al. |
| 2005/0245821 A1 | 11/2005 | Govari et al. |
| 2005/0256532 A1 | 11/2005 | Nayak et al. |
| 2005/0267478 A1 | 12/2005 | Corradi et al. |
| 2005/0273138 A1 | 12/2005 | To et al. |
| 2005/0288776 A1* | 12/2005 | Shaoulian ............ A61F 2/2445 623/2.37 |
| 2005/0288778 A1 | 12/2005 | Shaoulian et al. |
| 2006/0004442 A1 | 1/2006 | Spenser et al. |
| 2006/0004443 A1 | 1/2006 | Liddicoat et al. |
| 2006/0020326 A9 | 1/2006 | Bolduc et al. |
| 2006/0020327 A1 | 1/2006 | Lashinski et al. |
| 2006/0020333 A1 | 1/2006 | Lashinski et al. |
| 2006/0020336 A1 | 1/2006 | Liddicoat |
| 2006/0025787 A1 | 2/2006 | Morales et al. |
| 2006/0025858 A1 | 2/2006 | Alameddine |
| 2006/0030885 A1 | 2/2006 | Hyde |
| 2006/0041319 A1 | 2/2006 | Taylor et al. |
| 2006/0069429 A1 | 3/2006 | Spence et al. |
| 2006/0074486 A1 | 4/2006 | Liddicoat et al. |
| 2006/0085012 A1 | 4/2006 | Dolan |
| 2006/0095009 A1 | 5/2006 | Lampropoulos et al. |
| 2006/0106423 A1 | 5/2006 | Weisel et al. |
| 2006/0116757 A1 | 6/2006 | Lashinski et al. |
| 2006/0122633 A1 | 6/2006 | To et al. |
| 2006/0129166 A1 | 6/2006 | Lavelle |
| 2006/0142694 A1 | 6/2006 | Bednarek et al. |
| 2006/0149280 A1 | 7/2006 | Harvie et al. |
| 2006/0149368 A1 | 7/2006 | Spence |
| 2006/0161265 A1 | 7/2006 | Levine et al. |
| 2006/0173251 A1 | 8/2006 | Govari et al. |
| 2006/0184240 A1 | 8/2006 | Jimenez et al. |
| 2006/0184242 A1 | 8/2006 | Lichtenstein |
| 2006/0195134 A1 | 8/2006 | Crittenden |
| 2006/0206203 A1 | 9/2006 | Yang et al. |
| 2006/0241622 A1 | 10/2006 | Zergiebel |
| 2006/0241656 A1 | 10/2006 | Starksen et al. |
| 2006/0241748 A1 | 10/2006 | Lee et al. |
| 2006/0247763 A1 | 11/2006 | Slater |
| 2006/0259135 A1 | 11/2006 | Navia et al. |
| 2006/0271175 A1 | 11/2006 | Woolfson et al. |
| 2006/0276871 A1 | 12/2006 | Lamson et al. |
| 2006/0282161 A1 | 12/2006 | Huynh et al. |
| 2006/0287661 A1 | 12/2006 | Bolduc et al. |
| 2006/0287716 A1 | 12/2006 | Banbury et al. |
| 2007/0001627 A1 | 1/2007 | Lin et al. |
| 2007/0010800 A1 | 1/2007 | Weitzner et al. |
| 2007/0016286 A1 | 1/2007 | Herrmann et al. |
| 2007/0016287 A1* | 1/2007 | Cartledge ............ A61F 2/2448 623/2.37 |
| 2007/0016288 A1 | 1/2007 | Gurskis et al. |
| 2007/0021781 A1 | 1/2007 | Jervis et al. |
| 2007/0027533 A1 | 2/2007 | Douk |
| 2007/0027536 A1 | 2/2007 | Mihaljevic et al. |
| 2007/0032823 A1 | 2/2007 | Tegg |
| 2007/0038221 A1 | 2/2007 | Fine et al. |

(56) References Cited

U.S. PATENT DOCUMENTS

| | | |
|---|---|---|
| 2007/0038293 A1 | 2/2007 | St.Goar et al. |
| 2007/0038296 A1 | 2/2007 | Navia et al. |
| 2007/0039425 A1 | 2/2007 | Wang |
| 2007/0049942 A1 | 3/2007 | Hindrichs et al. |
| 2007/0049970 A1 | 3/2007 | Belef et al. |
| 2007/0051377 A1 | 3/2007 | Douk et al. |
| 2007/0055206 A1 | 3/2007 | To et al. |
| 2007/0060922 A1 | 3/2007 | Dreyfuss |
| 2007/0061010 A1 | 3/2007 | Hauser et al. |
| 2007/0066863 A1 | 3/2007 | Rafiee et al. |
| 2007/0078297 A1 | 4/2007 | Rafiee et al. |
| 2007/0080188 A1 | 4/2007 | Spence et al. |
| 2007/0083168 A1 | 4/2007 | Whiting et al. |
| 2007/0083235 A1 | 4/2007 | Jervis et al. |
| 2007/0100427 A1 | 5/2007 | Perouse |
| 2007/0106328 A1 | 5/2007 | Wardle et al. |
| 2007/0112359 A1 | 5/2007 | Kimura et al. |
| 2007/0112422 A1 | 5/2007 | Dehdashtian |
| 2007/0112425 A1 | 5/2007 | Schaller et al. |
| 2007/0118151 A1 | 5/2007 | Davidson |
| 2007/0118154 A1 | 5/2007 | Crabtree |
| 2007/0118213 A1 | 5/2007 | Loulmet |
| 2007/0118215 A1 | 5/2007 | Moaddeb |
| 2007/0142907 A1 | 6/2007 | Moaddeb et al. |
| 2007/0162111 A1 | 7/2007 | Fukamachi et al. |
| 2007/0173931 A1 | 7/2007 | Tremulis et al. |
| 2007/0197858 A1 | 8/2007 | Goldfarb et al. |
| 2007/0198082 A1 | 8/2007 | Kapadia et al. |
| 2007/0219558 A1 | 9/2007 | Deutsch |
| 2007/0239208 A1 | 10/2007 | Crawford |
| 2007/0244554 A1 | 10/2007 | Rafiee et al. |
| 2007/0244556 A1 | 10/2007 | Rafiee et al. |
| 2007/0244557 A1* | 10/2007 | Rafiee ............... A61F 2/2448 623/2.37 |
| 2007/0255397 A1 | 11/2007 | Ryan et al. |
| 2007/0255400 A1 | 11/2007 | Parravicini et al. |
| 2007/0265491 A1 | 11/2007 | Krag et al. |
| 2007/0270679 A1 | 11/2007 | Nguyen et al. |
| 2007/0270755 A1 | 11/2007 | Von Oepen et al. |
| 2007/0276437 A1 | 11/2007 | Call et al. |
| 2007/0282375 A1 | 12/2007 | Hindrichs et al. |
| 2007/0282429 A1 | 12/2007 | Hauser et al. |
| 2007/0295172 A1 | 12/2007 | Swartz |
| 2007/0299424 A1 | 12/2007 | Cumming et al. |
| 2008/0004697 A1 | 1/2008 | Lichtenstein et al. |
| 2008/0027483 A1 | 1/2008 | Cartledge et al. |
| 2008/0027555 A1 | 1/2008 | Hawkins |
| 2008/0035160 A1 | 2/2008 | Woodson et al. |
| 2008/0039935 A1 | 2/2008 | Buch et al. |
| 2008/0051703 A1 | 2/2008 | Thornton et al. |
| 2008/0058595 A1 | 3/2008 | Snoke et al. |
| 2008/0065011 A1 | 3/2008 | Marchand et al. |
| 2008/0065204 A1 | 3/2008 | Macoviak et al. |
| 2008/0071366 A1 | 3/2008 | Tuval et al. |
| 2008/0082132 A1 | 4/2008 | Annest et al. |
| 2008/0086138 A1 | 4/2008 | Stone et al. |
| 2008/0086203 A1 | 4/2008 | Roberts |
| 2008/0091169 A1 | 4/2008 | Heideman et al. |
| 2008/0091257 A1 | 4/2008 | Andreas et al. |
| 2008/0097483 A1 | 4/2008 | Ortiz et al. |
| 2008/0097523 A1 | 4/2008 | Bolduc et al. |
| 2008/0103572 A1 | 5/2008 | Gerber |
| 2008/0140116 A1 | 6/2008 | Bonutti |
| 2008/0167713 A1 | 7/2008 | Bolling |
| 2008/0167714 A1 | 7/2008 | St. Goar et al. |
| 2008/0177380 A1 | 7/2008 | Starksen et al. |
| 2008/0195126 A1 | 8/2008 | Solem |
| 2008/0195200 A1 | 8/2008 | Vidlund et al. |
| 2008/0208265 A1 | 8/2008 | Frazier et al. |
| 2008/0221672 A1 | 9/2008 | Lamphere et al. |
| 2008/0228030 A1 | 9/2008 | Godin |
| 2008/0228223 A1 | 9/2008 | Alkhatib |
| 2008/0234729 A1 | 9/2008 | Page et al. |
| 2008/0262480 A1 | 10/2008 | Stahler et al. |
| 2008/0262609 A1* | 10/2008 | Gross ............... A61F 2/2445 623/2.38 |
| 2008/0275300 A1 | 11/2008 | Rothe et al. |
| 2008/0275469 A1 | 11/2008 | Fanton et al. |
| 2008/0275551 A1 | 11/2008 | Alfieri |
| 2008/0281353 A1 | 11/2008 | Aranyi et al. |
| 2008/0281411 A1 | 11/2008 | Berreklouw |
| 2008/0287862 A1 | 11/2008 | Weitzner et al. |
| 2008/0288044 A1 | 11/2008 | Osborne |
| 2008/0288062 A1 | 11/2008 | Andrieu et al. |
| 2008/0294251 A1 | 11/2008 | Annest et al. |
| 2008/0300537 A1 | 12/2008 | Bowman |
| 2008/0300629 A1 | 12/2008 | Surti |
| 2008/0312506 A1 | 12/2008 | Spivey et al. |
| 2009/0024110 A1 | 1/2009 | Heideman et al. |
| 2009/0028670 A1 | 1/2009 | Garcia et al. |
| 2009/0043381 A1 | 2/2009 | Macoviak et al. |
| 2009/0054723 A1 | 2/2009 | Khairkhahan et al. |
| 2009/0054969 A1 | 2/2009 | Salahieh et al. |
| 2009/0062866 A1 | 3/2009 | Jackson |
| 2009/0076586 A1 | 3/2009 | Hauser et al. |
| 2009/0076600 A1 | 3/2009 | Quinn |
| 2009/0082797 A1 | 3/2009 | Fung et al. |
| 2009/0088837 A1 | 4/2009 | Gillinov et al. |
| 2009/0093877 A1 | 4/2009 | Keidar et al. |
| 2009/0099650 A1 | 4/2009 | Bolduc et al. |
| 2009/0105816 A1 | 4/2009 | Olsen et al. |
| 2009/0125102 A1 | 5/2009 | Cartledge et al. |
| 2009/0166913 A1 | 7/2009 | Guo et al. |
| 2009/0171439 A1 | 7/2009 | Nissl |
| 2009/0177266 A1 | 7/2009 | Powell et al. |
| 2009/0177274 A1 | 7/2009 | Scorsin et al. |
| 2009/0177277 A1* | 7/2009 | Milo ............... A61F 2/2445 623/2.36 |
| 2009/0187216 A1 | 7/2009 | Schmieding et al. |
| 2009/0222083 A1 | 9/2009 | Nguyen et al. |
| 2009/0248148 A1 | 10/2009 | Shaolian et al. |
| 2009/0254103 A1 | 10/2009 | Deutsch |
| 2009/0264994 A1 | 10/2009 | Saadat |
| 2009/0287231 A1 | 11/2009 | Brooks et al. |
| 2009/0287304 A1 | 11/2009 | Dahlgren et al. |
| 2009/0299409 A1 | 12/2009 | Coe et al. |
| 2009/0326648 A1 | 12/2009 | Machold et al. |
| 2010/0001038 A1 | 1/2010 | Levin et al. |
| 2010/0010538 A1 | 1/2010 | Juravic et al. |
| 2010/0023118 A1 | 1/2010 | Medlock et al. |
| 2010/0030014 A1 | 2/2010 | Ferrazzi |
| 2010/0030328 A1 | 2/2010 | Seguin et al. |
| 2010/0042147 A1 | 2/2010 | Janovsky et al. |
| 2010/0049213 A1 | 2/2010 | Serina et al. |
| 2010/0063542 A1 | 3/2010 | van der Burg et al. |
| 2010/0063550 A1 | 3/2010 | Felix et al. |
| 2010/0076499 A1 | 3/2010 | McNamara et al. |
| 2010/0094248 A1 | 4/2010 | Nguyen et al. |
| 2010/0094314 A1 | 4/2010 | Hernlund et al. |
| 2010/0106141 A1 | 4/2010 | Osypka et al. |
| 2010/0114180 A1 | 5/2010 | Rock et al. |
| 2010/0121349 A1 | 5/2010 | Meier et al. |
| 2010/0121435 A1 | 5/2010 | Subramanian et al. |
| 2010/0121437 A1 | 5/2010 | Subramanian et al. |
| 2010/0130989 A1 | 5/2010 | Bourque et al. |
| 2010/0130992 A1 | 5/2010 | Machold et al. |
| 2010/0152845 A1 | 6/2010 | Bloom et al. |
| 2010/0161042 A1 | 6/2010 | Maisano et al. |
| 2010/0161043 A1 | 6/2010 | Maisano et al. |
| 2010/0161047 A1 | 6/2010 | Cabiri |
| 2010/0168827 A1 | 7/2010 | Schultz |
| 2010/0168845 A1 | 7/2010 | Wright |
| 2010/0174358 A1 | 7/2010 | Rabkin et al. |
| 2010/0179574 A1 | 7/2010 | Longoria et al. |
| 2010/0211166 A1* | 8/2010 | Miller ............... A61F 2/2448 623/2.37 |
| 2010/0217184 A1 | 8/2010 | Koblish et al. |
| 2010/0217382 A1 | 8/2010 | Chau et al. |
| 2010/0234935 A1 | 9/2010 | Bashiri et al. |
| 2010/0249497 A1 | 9/2010 | Peine et al. |
| 2010/0249908 A1 | 9/2010 | Chau et al. |
| 2010/0249915 A1 | 9/2010 | Zhang |
| 2010/0249920 A1 | 9/2010 | Bolling et al. |

(56) References Cited

U.S. PATENT DOCUMENTS

| | | |
|---|---|---|
| 2010/0262232 A1 | 10/2010 | Annest |
| 2010/0262233 A1 | 10/2010 | He |
| 2010/0280604 A1 | 11/2010 | Zipory et al. |
| 2010/0280605 A1 | 11/2010 | Hammer et al. |
| 2010/0286628 A1 | 11/2010 | Gross |
| 2010/0298929 A1 | 11/2010 | Thornton et al. |
| 2010/0305475 A1 | 12/2010 | Hinchliffe et al. |
| 2010/0324598 A1 | 12/2010 | Anderson |
| 2011/0004210 A1 | 1/2011 | Johnson et al. |
| 2011/0004298 A1 | 1/2011 | Lee et al. |
| 2011/0009956 A1 | 1/2011 | Cartledge et al. |
| 2011/0011917 A1 | 1/2011 | Loulmet |
| 2011/0026208 A1 | 2/2011 | Utsuro et al. |
| 2011/0029066 A1 | 2/2011 | Gilad et al. |
| 2011/0035000 A1 | 2/2011 | Nieminen et al. |
| 2011/0066231 A1 | 3/2011 | Cartledge et al. |
| 2011/0067770 A1 | 3/2011 | Pederson et al. |
| 2011/0071626 A1 | 3/2011 | Wright et al. |
| 2011/0082538 A1 | 4/2011 | Dahlgren et al. |
| 2011/0087146 A1 | 4/2011 | Ryan et al. |
| 2011/0093002 A1 | 4/2011 | Rucker et al. |
| 2011/0106247 A1 | 5/2011 | Miller et al. |
| 2011/0118832 A1* | 5/2011 | Punjabi .......... A61F 2/2445 623/2.36 |
| 2011/0137410 A1 | 6/2011 | Hacohen |
| 2011/0144576 A1 | 6/2011 | Rothe et al. |
| 2011/0144703 A1 | 6/2011 | Krause et al. |
| 2011/0202130 A1 | 8/2011 | Cartledge et al. |
| 2011/0208283 A1 | 8/2011 | Rust |
| 2011/0230941 A1 | 9/2011 | Markus |
| 2011/0230961 A1 | 9/2011 | Langer et al. |
| 2011/0238088 A1 | 9/2011 | Bolduc et al. |
| 2011/0257433 A1 | 10/2011 | Walker |
| 2011/0257633 A1 | 10/2011 | Cartledge et al. |
| 2011/0264208 A1 | 10/2011 | Duffy et al. |
| 2011/0276062 A1 | 11/2011 | Bolduc |
| 2011/0288435 A1 | 11/2011 | Christy et al. |
| 2011/0301498 A1 | 12/2011 | Maenhout et al. |
| 2012/0022557 A1 | 1/2012 | Cabiri et al. |
| 2012/0053628 A1 | 3/2012 | Sojka et al. |
| 2012/0065464 A1 | 3/2012 | Ellis et al. |
| 2012/0078355 A1 | 3/2012 | Zipory et al. |
| 2012/0078359 A1 | 3/2012 | Li et al. |
| 2012/0089022 A1 | 4/2012 | House et al. |
| 2012/0089125 A1 | 4/2012 | Scheibe et al. |
| 2012/0095552 A1 | 4/2012 | Spence et al. |
| 2012/0101571 A1 | 4/2012 | Thambar et al. |
| 2012/0109155 A1 | 5/2012 | Robinson et al. |
| 2012/0150290 A1 | 6/2012 | Gabbay |
| 2012/0158021 A1 | 6/2012 | Morrill |
| 2012/0158023 A1 | 6/2012 | Mitelberg et al. |
| 2012/0179086 A1 | 7/2012 | Shank et al. |
| 2012/0191182 A1 | 7/2012 | Hauser et al. |
| 2012/0226349 A1 | 9/2012 | Tuval et al. |
| 2012/0239142 A1 | 9/2012 | Liu et al. |
| 2012/0245604 A1 | 9/2012 | Tegzes |
| 2012/0271198 A1 | 10/2012 | Whittaker et al. |
| 2012/0283757 A1 | 11/2012 | Miller et al. |
| 2012/0296349 A1 | 11/2012 | Smith et al. |
| 2012/0296417 A1 | 11/2012 | Hill et al. |
| 2012/0310330 A1* | 12/2012 | Buchbinder ........ A61F 2/2448 623/2.11 |
| 2012/0323313 A1 | 12/2012 | Seguin |
| 2012/0330411 A1* | 12/2012 | Gross ................ A61F 2/2445 623/2.37 |
| 2013/0030522 A1 | 1/2013 | Rowe et al. |
| 2013/0046373 A1 | 2/2013 | Cartledge et al. |
| 2013/0053884 A1 | 2/2013 | Roorda |
| 2013/0079873 A1 | 3/2013 | Migliazza et al. |
| 2013/0085529 A1 | 4/2013 | Housman |
| 2013/0090724 A1 | 4/2013 | Subramanian et al. |
| 2013/0096673 A1 | 4/2013 | Hill et al. |
| 2013/0116776 A1 | 5/2013 | Gross et al. |
| 2013/0123910 A1 | 5/2013 | Cartledge et al. |
| 2013/0131791 A1 | 5/2013 | Hlavka et al. |
| 2013/0166017 A1 | 6/2013 | Cartledge et al. |
| 2013/0190863 A1 | 7/2013 | Call et al. |
| 2013/0204361 A1 | 8/2013 | Adams et al. |
| 2013/0226289 A1 | 8/2013 | Shaolian et al. |
| 2013/0226290 A1 | 8/2013 | Yellin et al. |
| 2013/0231701 A1 | 9/2013 | Voss et al. |
| 2013/0268069 A1 | 10/2013 | Zakai et al. |
| 2013/0282059 A1 | 10/2013 | Ketai et al. |
| 2013/0289718 A1 | 10/2013 | Tsukashima et al. |
| 2013/0297013 A1 | 11/2013 | Klima et al. |
| 2013/0304093 A1 | 11/2013 | Serina et al. |
| 2013/0331930 A1 | 12/2013 | Rowe et al. |
| 2014/0067054 A1 | 3/2014 | Chau et al. |
| 2014/0081394 A1 | 3/2014 | Keranen et al. |
| 2014/0088368 A1 | 3/2014 | Park |
| 2014/0088646 A1 | 3/2014 | Wales et al. |
| 2014/0094826 A1 | 4/2014 | Sutherland et al. |
| 2014/0094903 A1 | 4/2014 | Miller et al. |
| 2014/0094906 A1 | 4/2014 | Spence et al. |
| 2014/0114390 A1 | 4/2014 | Tobis et al. |
| 2014/0135799 A1 | 5/2014 | Henderson |
| 2014/0142619 A1 | 5/2014 | Serina et al. |
| 2014/0142695 A1 | 5/2014 | Gross et al. |
| 2014/0148849 A1 | 5/2014 | Serina et al. |
| 2014/0155783 A1 | 6/2014 | Starksen et al. |
| 2014/0163670 A1 | 6/2014 | Alon et al. |
| 2014/0163690 A1 | 6/2014 | White |
| 2014/0188108 A1 | 7/2014 | Goodine et al. |
| 2014/0188140 A1 | 7/2014 | Meier et al. |
| 2014/0188215 A1 | 7/2014 | Hlavka et al. |
| 2014/0194976 A1 | 7/2014 | Starksen et al. |
| 2014/0207231 A1 | 7/2014 | Hacohen et al. |
| 2014/0243859 A1 | 8/2014 | Robinson |
| 2014/0243894 A1 | 8/2014 | Groothuis et al. |
| 2014/0243963 A1 | 8/2014 | Sheps et al. |
| 2014/0251042 A1 | 9/2014 | Asselin et al. |
| 2014/0275757 A1 | 9/2014 | Goodwin et al. |
| 2014/0276648 A1 | 9/2014 | Hammer et al. |
| 2014/0296962 A1 | 10/2014 | Cartledge et al. |
| 2014/0303649 A1 | 10/2014 | Nguyen et al. |
| 2014/0303720 A1 | 10/2014 | Sugimoto et al. |
| 2014/0309661 A1 | 10/2014 | Sheps et al. |
| 2014/0309730 A1 | 10/2014 | Alon et al. |
| 2014/0343668 A1 | 11/2014 | Zipory et al. |
| 2014/0350660 A1 | 11/2014 | Cocks et al. |
| 2014/0379006 A1 | 12/2014 | Sutherland et al. |
| 2015/0018940 A1 | 1/2015 | Quill et al. |
| 2015/0051697 A1 | 2/2015 | Spence et al. |
| 2015/0081014 A1 | 3/2015 | Gross et al. |
| 2015/0094800 A1 | 4/2015 | Chawla |
| 2015/0100116 A1 | 4/2015 | Mohl et al. |
| 2015/0112432 A1 | 4/2015 | Reich et al. |
| 2015/0127097 A1 | 5/2015 | Neumann et al. |
| 2015/0133997 A1 | 5/2015 | Deitch et al. |
| 2015/0182336 A1 | 7/2015 | Zipory et al. |
| 2015/0230919 A1 | 8/2015 | Chau et al. |
| 2015/0272586 A1 | 10/2015 | Herman et al. |
| 2015/0272734 A1 | 10/2015 | Sheps et al. |
| 2015/0282931 A1 | 10/2015 | Brunnett et al. |
| 2015/0351906 A1 | 12/2015 | Hammer et al. |
| 2015/0351910 A1 | 12/2015 | Gilmore et al. |
| 2016/0008132 A1 | 1/2016 | Cabiri et al. |
| 2016/0029920 A1 | 2/2016 | Kronstrom et al. |
| 2016/0058557 A1 | 3/2016 | Reich et al. |
| 2016/0113767 A1 | 4/2016 | Miller et al. |
| 2016/0120642 A1 | 5/2016 | Shaolian et al. |
| 2016/0120645 A1 | 5/2016 | Alon |
| 2016/0158008 A1 | 6/2016 | Miller et al. |
| 2016/0242762 A1 | 8/2016 | Gilmore et al. |
| 2016/0256149 A1 | 9/2016 | Sampson et al. |
| 2016/0262755 A1 | 9/2016 | Zipory et al. |
| 2016/0302917 A1 | 10/2016 | Schewel |
| 2016/0317302 A1 | 11/2016 | Madjarov et al. |
| 2016/0361058 A1 | 12/2016 | Bolduc et al. |
| 2016/0361168 A1 | 12/2016 | Gross et al. |
| 2016/0361169 A1 | 12/2016 | Gross et al. |
| 2017/0000609 A1 | 1/2017 | Gross et al. |
| 2017/0042670 A1 | 2/2017 | Shaolian et al. |
| 2017/0100119 A1 | 4/2017 | Baird et al. |

(56) References Cited

U.S. PATENT DOCUMENTS

| | | |
|---|---|---|
| 2017/0224489 A1 | 8/2017 | Starksen et al. |
| 2017/0245993 A1 | 8/2017 | Gross et al. |
| 2017/0325959 A1 | 11/2017 | Sheps et al. |
| 2018/0008409 A1 | 1/2018 | Kutzik et al. |
| 2018/0049875 A1 | 2/2018 | Iflah et al. |
| 2018/0140420 A1 | 5/2018 | Hayoz et al. |
| 2018/0168803 A1 | 6/2018 | Pesce et al. |
| 2018/0228608 A1 | 8/2018 | Sheps et al. |
| 2018/0256334 A1 | 9/2018 | Sheps et al. |
| 2018/0289480 A1 | 10/2018 | D'ambra et al. |
| 2018/0318080 A1 | 11/2018 | Quill et al. |
| 2018/0318083 A1 | 11/2018 | Bolling et al. |
| 2019/0029498 A1 | 1/2019 | Mankowski et al. |
| 2019/0038411 A1 | 2/2019 | Alon |
| 2019/0111239 A1 | 4/2019 | Bolduc et al. |
| 2019/0117400 A1 | 4/2019 | Medema et al. |
| 2019/0125325 A1 | 5/2019 | Sheps et al. |
| 2019/0151093 A1 | 5/2019 | Keidar et al. |
| 2019/0159898 A1 | 5/2019 | Kutzik et al. |
| 2019/0175344 A1 | 6/2019 | Khairkhahan |
| 2019/0175345 A1 | 6/2019 | Schaffner et al. |
| 2019/0175346 A1 | 6/2019 | Schaffner et al. |
| 2019/0183648 A1 | 6/2019 | Trapp et al. |
| 2019/0240023 A1 | 8/2019 | Spence et al. |
| 2019/0290260 A1 | 9/2019 | Caffes et al. |
| 2019/0290431 A1 | 9/2019 | Genovese et al. |
| 2019/0321049 A1 | 10/2019 | Herman et al. |
| 2019/0343633 A1 | 11/2019 | Garvin et al. |
| 2020/0015971 A1 | 1/2020 | Brauon et al. |
| 2020/0289267 A1 | 9/2020 | Peleg et al. |
| 2020/0337840 A1 | 10/2020 | Reich |
| 2021/0015475 A1 | 1/2021 | Lau |
| 2021/0059820 A1 | 3/2021 | Clark et al. |
| 2021/0085461 A1 | 3/2021 | Neumark et al. |
| 2021/0093453 A1 | 4/2021 | Peleg et al. |
| 2021/0145584 A1 | 5/2021 | Kasher et al. |
| 2022/0071620 A1 | 3/2022 | Brauon et al. |
| 2022/0096232 A1 | 3/2022 | Skaro et al. |
| 2022/0142779 A1 | 5/2022 | Sharon |
| 2022/0176076 A1 | 6/2022 | Keidar |
| 2022/0233316 A1 | 7/2022 | Sheps et al. |
| 2022/0273436 A1 | 9/2022 | Aviv et al. |
| 2022/0313438 A1 | 10/2022 | Chappel-Ram |
| 2022/0323221 A1 | 10/2022 | Sharon et al. |
| 2023/0016867 A1 | 1/2023 | Tennenbaum |
| 2023/0218291 A1 | 7/2023 | Zarbatany et al. |

FOREIGN PATENT DOCUMENTS

| | | | |
|---|---|---|---|
| EP | 1034753 A1 | 9/2000 | |
| EP | 3531975 A1 | 9/2019 | |
| WO | 9205093 A1 | 4/1992 | |
| WO | 9846149 A1 | 10/1998 | |
| WO | 02085250 A3 | 2/2003 | |
| WO | 03047467 A1 | 6/2003 | |
| WO | 2007098512 A1 | 9/2007 | |
| WO | 2010000454 A1 | 1/2010 | |
| WO | WO-2010004546 A1 * | 1/2010 | ........... A61F 2/2442 |
| WO | 2012176195 A3 | 3/2013 | |
| WO | 2014064964 A1 | 5/2014 | |
| WO | 2019145941 A1 | 8/2019 | |
| WO | 2019145947 A1 | 8/2019 | |
| WO | 2019182645 A1 | 9/2019 | |
| WO | 2019224814 A1 | 11/2019 | |
| WO | 2020240282 A2 | 12/2020 | |
| WO | 2021014440 A2 | 1/2021 | |
| WO | 2021038559 A1 | 3/2021 | |
| WO | 2021038560 A1 | 3/2021 | |
| WO | 2022064401 A2 | 3/2022 | |
| WO | 2022090907 A1 | 5/2022 | |
| WO | 2022101817 A2 | 5/2022 | |
| WO | 2022153131 A1 | 7/2022 | |
| WO | 2022157592 A1 | 7/2022 | |
| WO | 2022172108 A1 | 8/2022 | |
| WO | 2022172149 A1 | 8/2022 | |
| WO | 2022200972 A1 | 9/2022 | |
| WO | 2022224071 A1 | 10/2022 | |
| WO | 2022229815 A1 | 11/2022 | |
| WO | 2022250983 A1 | 12/2022 | |

OTHER PUBLICATIONS

Ahmadi, A., G. Spillner, and Th Johannesson. "Hemodynamic changes following experimental production and correction of acute mitral regurgitation with an adjustable ring prosthesis." The Thoracic and cardiovascular surgeon36.06 (1988): 313-319.

Ahmadi, Ali et al. "Percutaneously adjustable pulmonary artery band." The Annals of thoracic surgery 60 (1995): S520-S522.

Alfieri et al."Novel Suture Device for Beating-Heart Mitral Leaflet Approximation", Ann Thorac Surg. 2002, 74:1488-1493.

Alfieri et al., "An effective technique to correct anterior mitral leaflet prolapse," J Card 14(6):468-470 (1999).

Alfieri et al., "The double orifice technique in mitral valve repair: a simple solution for complex problems," Journal of Thoracic Cardiovascular Surgery 122:674-681 (2001).

Alfieri et al., "The edge to edge technique," The European Association for Cardio-Thoracic Surgery 14th Annual Meeting Oct. 7-11, Book of Procees. (2000).

Alfieri, "The edge-to-edge repair of the mitral valve," [Abstract] 6th Annual NewEra Cardiac Care: Innovation & Technology, Heart Surgery Forum pp. 103. (2000).

Amplatzer Cardiac Plug brochure (English pages), AGA Medical Corporation (Plymouth, MN) (copyright 2008-2010, downloaded Jan. 11, 2011).

Amplatzer® Cribriform Occluder. A patient guide to Percutaneous, Transcatheter, Atrial Septal Defect Closuer, AGA Medical Corporation, Apr. 2008.

Amplatzer® Septal Occluder. A patient guide to the Non-Surgical Closuer of the Atrial Septal Defect Using the Amplatzer Septal Occluder System, AGA Medical Corporation, Apr. 2008.

Assad, Renato S. "Adjustable Pulmonary Artery Banding." (2014).

Brennan, Jennifer, 510(k) Summary of safety and effectiveness, Jan. 2008.

Daebritz, S. et al. "Experience with an adjustable pulmonary artery banding device in two cases: initial success-midterm failure." The Thoracic and cardiovascular surgeon 47.01 (1999): 51-52.

Dang NC et al. "Simplified Placement of Multiple Artificial Mitral Valve Chords," The Heart Surgery Forum #2005-1005, 8 (3) (2005).

Dictionary.com definition of "lock", Jul. 29, 2013.

Dieter RS, "Percutaneous valve repair: Update on mitral regurgitation and endovascular approaches to the mitral valve," Applications in Imaging, Cardiac Interventions, Supported by an educational grant from Amersham Health pp. 11-14 (2003).

Elliott, Daniel S., Gerald W. Timm, and David M. Barrett. "An implantable mechanical urinary sphincter: a new nonhydraulic design concept." Urology52.6 (1998): 1151-1154.

Langer et al. Ring plus String: Papillary muscle repositioning as an adjunctive repair technique for ischemic mitral regurgitation, The Journal of Thoracic Cardiovascular surgery vol. 133 No. 1, Jan. 2007.

Langer et al. Ring+String, Successful Repair technique for ischemic mitral regurgitation with severe leaflet Tethering, The Department of Thoracic Cardiovascular surgery, Hamburg, Germany, Nov. 2008.

Maisano, "The double-orifice technique as a standardized approach to treat mitral," European Journal of Cardio-thoracic Surgery 17 (2000) 201-205.

O'Reilly S et al., "Heart valve surgery pushes the envelope," Medtech Insight 8(3): 73, 99-108 (2006).

Odell JA et al., "Early Results o4yf a Simplified Method of Mitral Valve Annuloplasty," Circulation 92:150-154 (1995).

Park, Sang C. et al. "A percutaneously adjustable device for banding of the pulmonary trunk." International journal of cardiology 9.4 (1985): 477-484.

Swain CP et al., "An endoscopically deliverable tissue-transfixing device for securing biosensors in the gastrointestinal tract," Gastrointestinal Endoscopy 40(6): 730-734 (1994).

(56) References Cited

OTHER PUBLICATIONS

Swenson, O. An experimental implantable urinary sphincter. Invest Urol. Sep. 1976;14(2):100-3.

Swenson, O. and Malinin, T.I., 1978. An improved mechanical device for control of urinary incontinence. Investigative urology, 15(5), pp. 389-391.

Swenson, Orvar. "Internal device for control of urinary incontinence." Journal of pediatric surgery 7.5 (1972): 542-545.

Tajik, Abdul, "Two dimensional real-time ultrasonic imaging of the heart and great vessels", Mayo Clin Proc. vol. 53:271-303, 1978.

\* cited by examiner

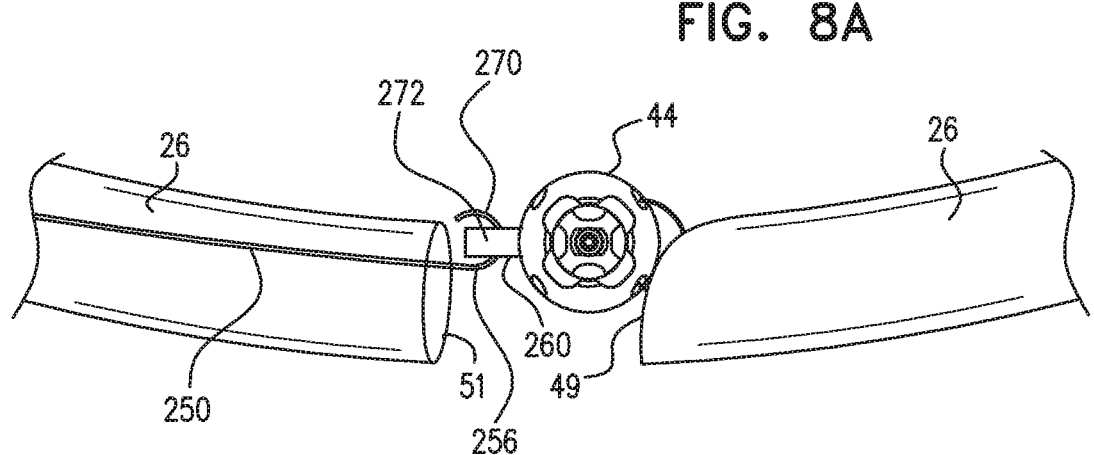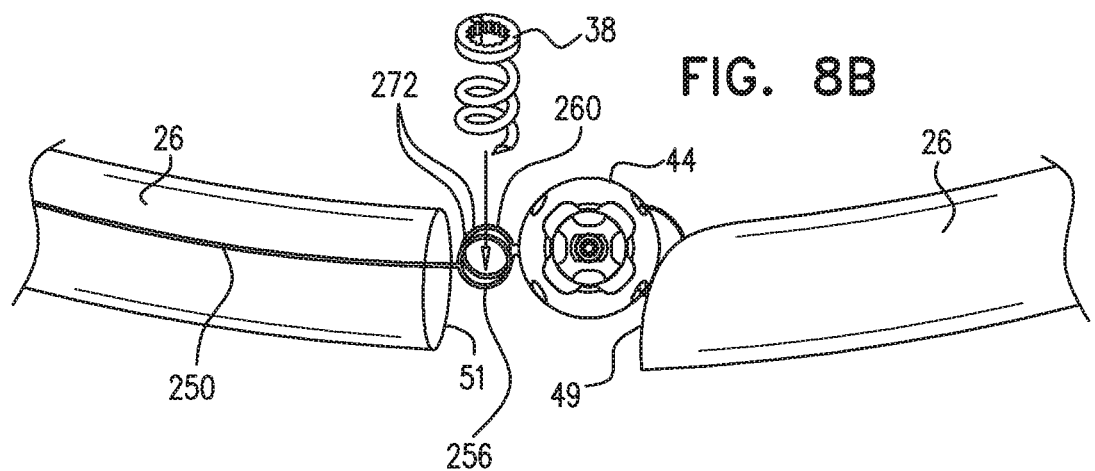

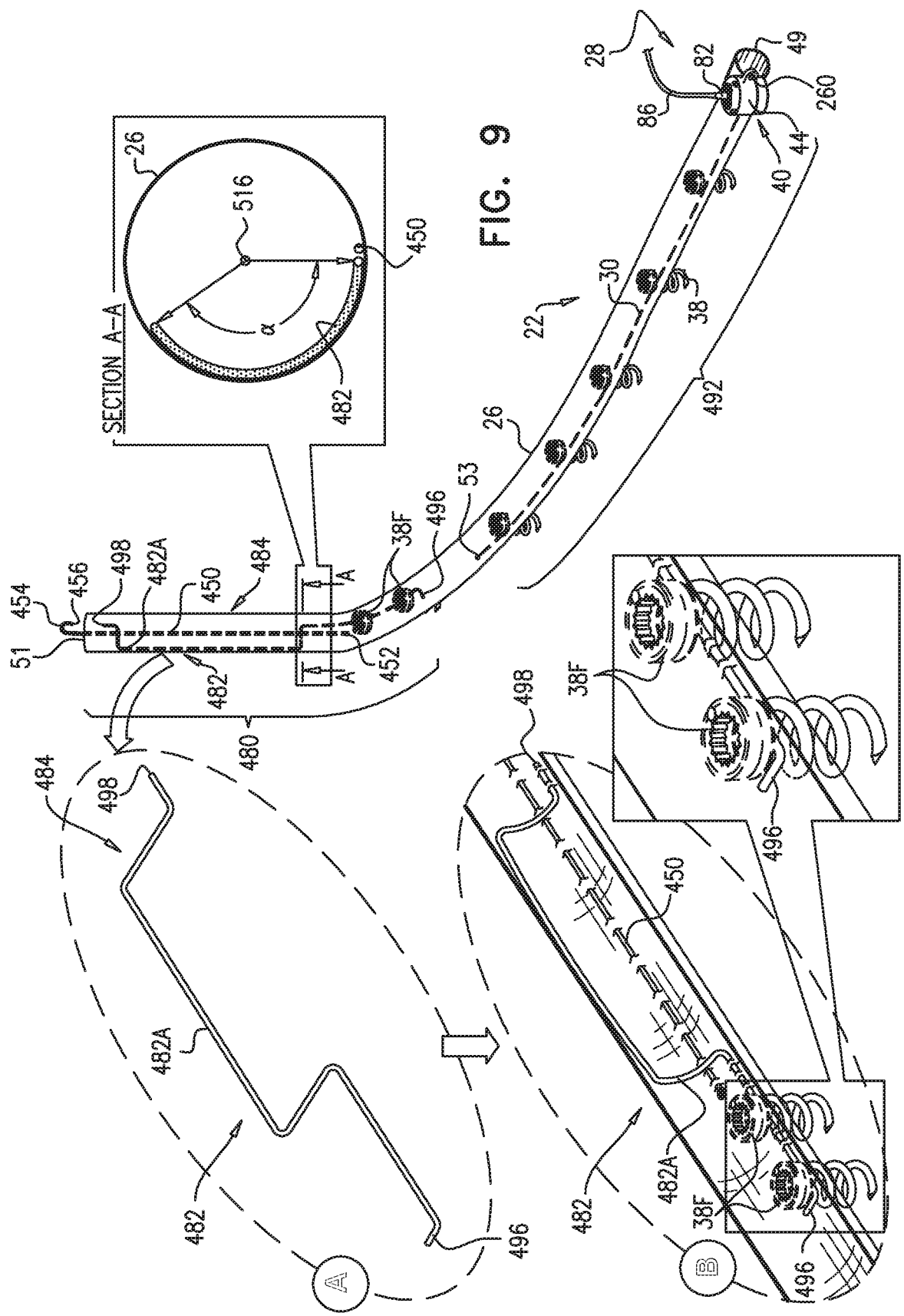

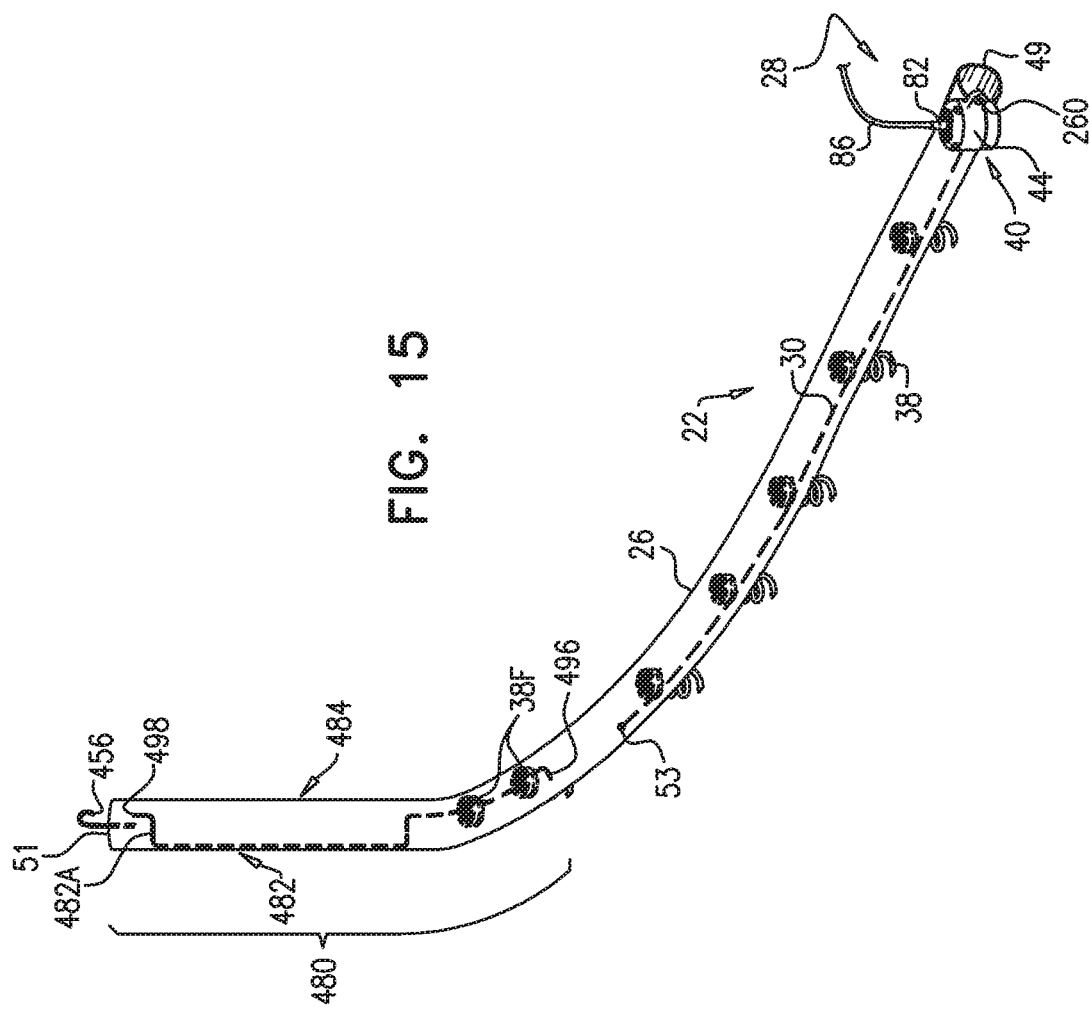

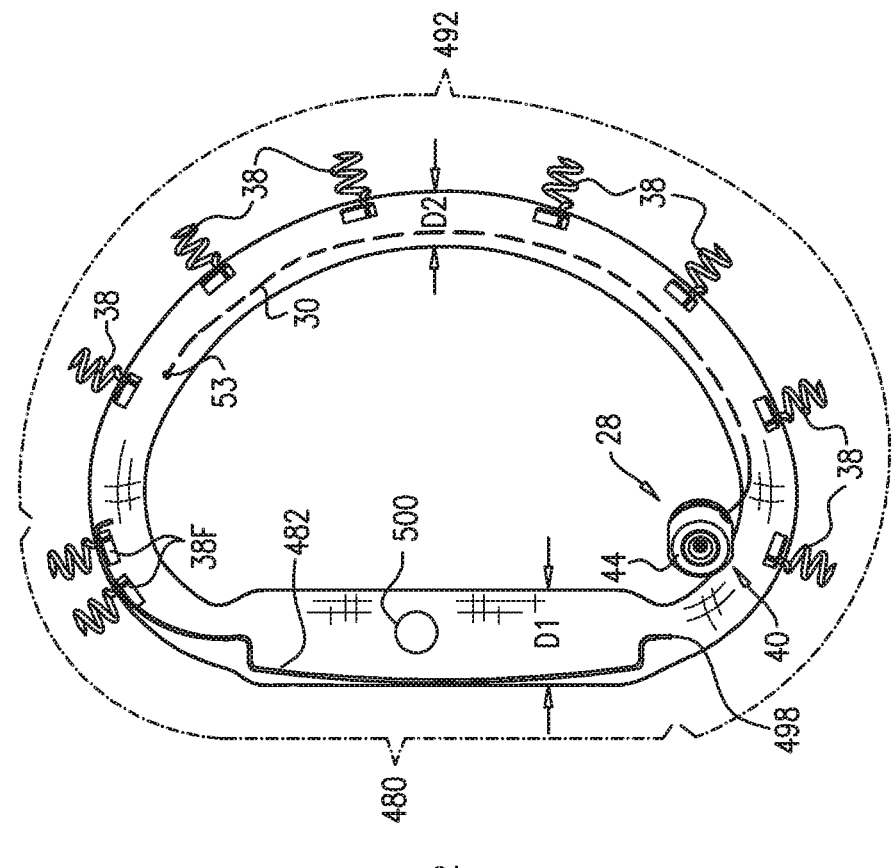
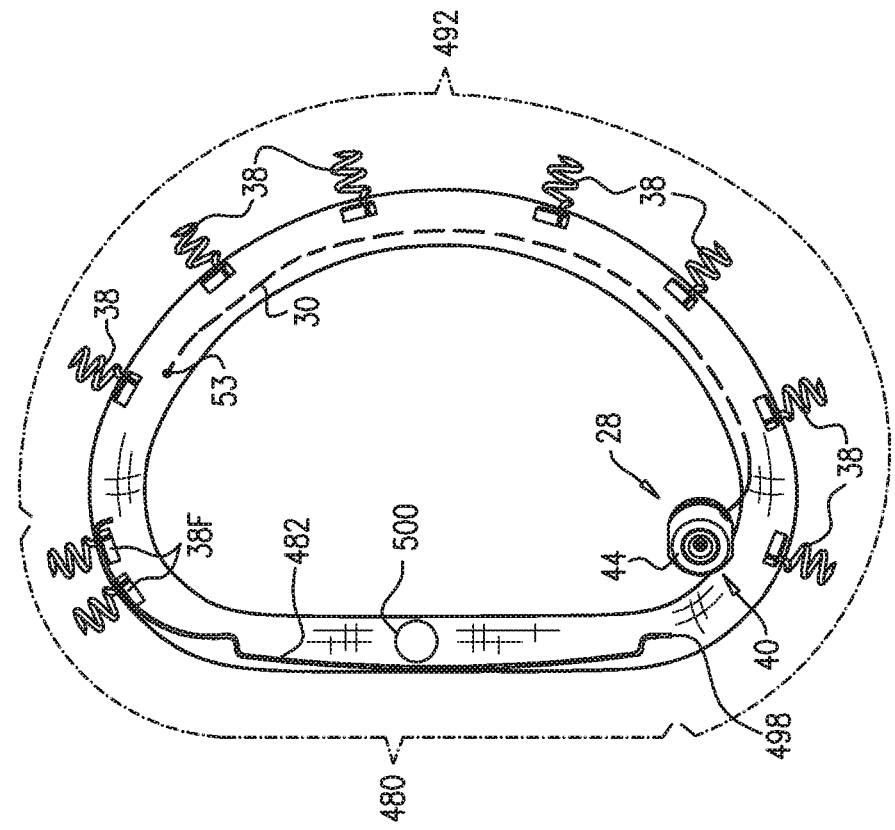

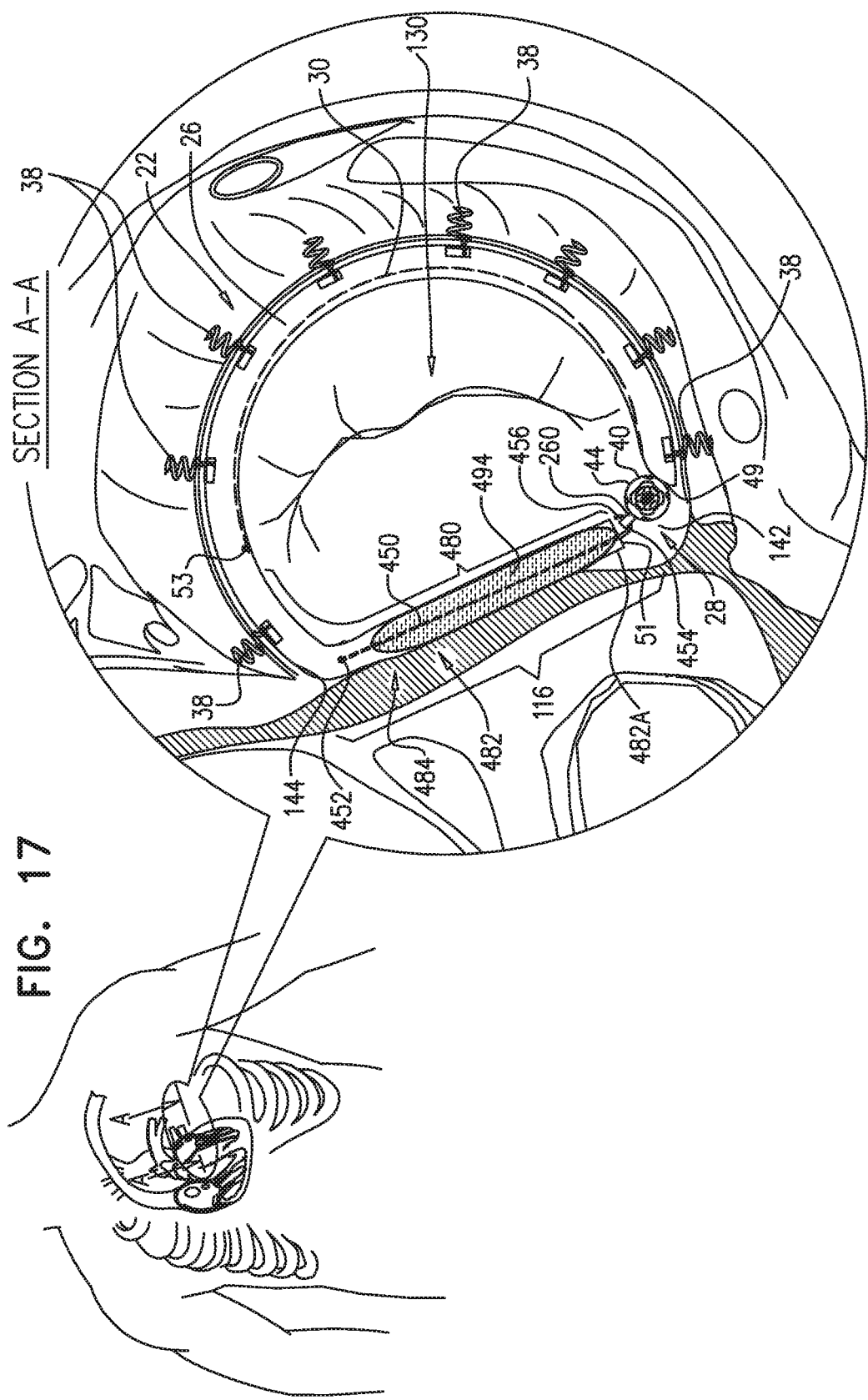

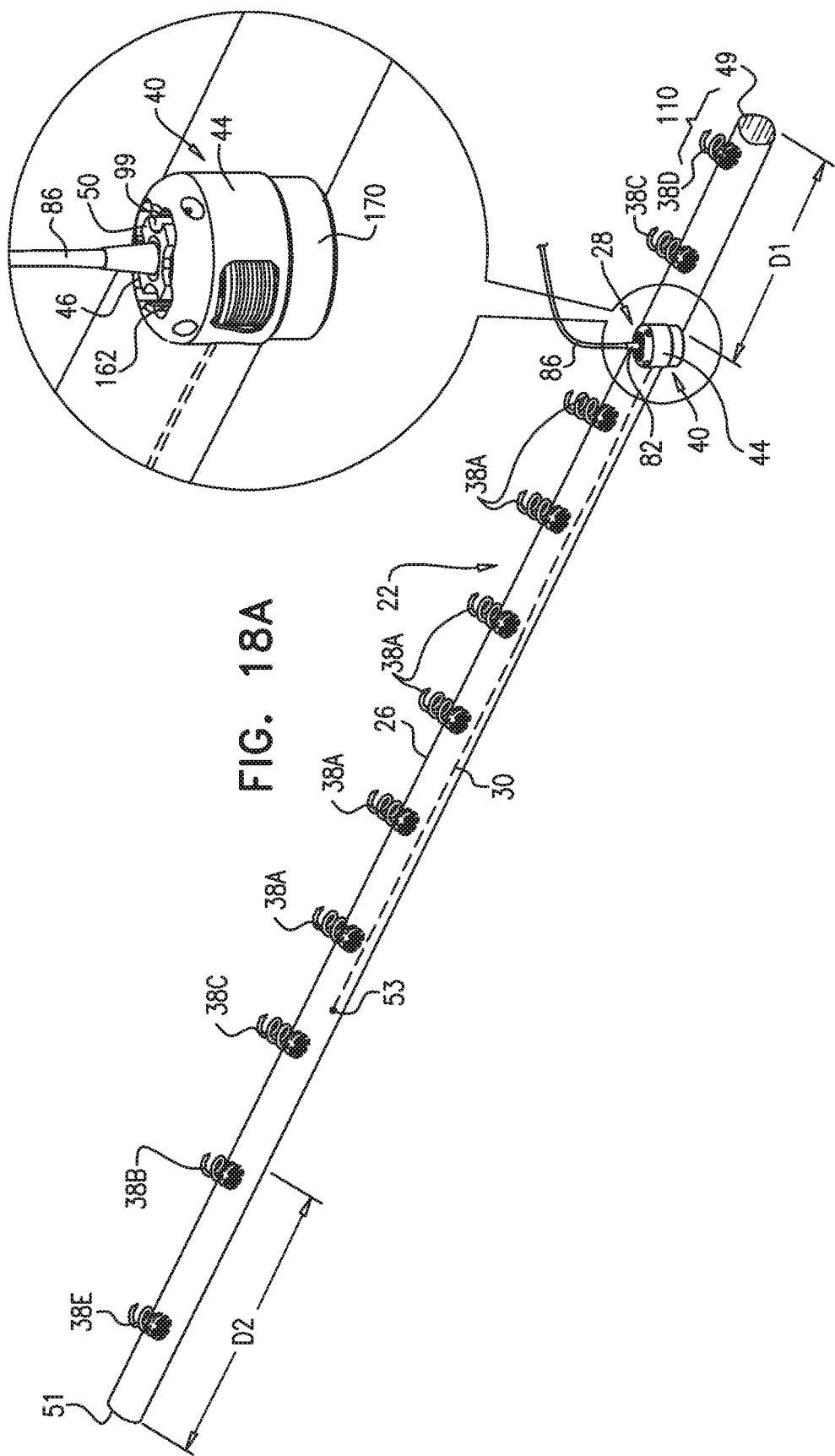

PERCUTANEOUS IMPLANTATION OF AN ANNULOPLASTY STRUCTURE

CROSS-REFERENCE TO RELATED APPLICATIONS

The present application is a Continuation of U.S. application Ser. No. 15/919,452, filed Mar. 13, 2018, which is:
a divisional of U.S. application Ser. No. 14/589,100, filed Jan. 5, 2015 (now U.S. Pat. No. 9,918,840); and
a continuation-in-part of U.S. application Ser. No. 15/474,543, filed Mar. 30, 2017 (now U.S. Pat. No. 10,470,882), which is a continuation of U.S. application Ser. No. 14/128,756, filed Feb. 6, 2014 (now U.S. Pat. No. 9,662,209), which is the US national phase of International Application PCT/IL2012/000250, filed Jun. 21, 2012, which (a) is a continuation-in-part of U.S. application Ser. No. 13/167,444, filed Jun. 23, 2011 (now U.S. Pat. No. 9,011,530), (b) is a continuation-in-part of U.S. application Ser. No. 13/167,476, filed Jun. 23, 2011 (now U.S. Pat. No. 8,940,044), and (c) is a continuation-in-part of U.S. application Ser. No. 13/167,492, filed Jun. 23, 2011 (now U.S. Pat. No. 8,926,697), which is assigned to the assignee of the present application and is incorporated herein by reference.

FIELD OF THE APPLICATION

Some applications of the present invention relate in general to valve repair, and more specifically to repair of an atrioventricular valve of a patient.

BACKGROUND OF THE APPLICATION

Dilation of the annulus of the mitral valve prevents the valve leaflets from fully coapting when the valve is closed. Mitral regurgitation of blood from the left ventricle into the left atrium results in increased total stroke volume and decreased cardiac output, and ultimate weakening of the left ventricle secondary to a volume overload and a pressure overload of the left atrium. Dilation of the annulus is sometimes treated by annuloplasty, in which a partial or full ring is implanted around the annulus to cause the leaflets to coapt when the valve is closed.

SUMMARY

In some applications of the present invention, an implantable structure is provided that comprises a flexible sleeve having first and second sleeve ends, a contracting assembly, and a plurality of tissue anchors. The contracting assembly is configured to longitudinally contract the sleeve, and comprises a contracting mechanism and a longitudinal contracting member having first and second member ends. The contracting mechanism is disposed longitudinally at a first site of the sleeve, and the second member end is coupled to the sleeve longitudinally at a second site longitudinally between the first site and the second sleeve end, exclusive. The contracting member also has a first member end portion, which extends from the first member end toward the second member end along only a longitudinal portion of the contracting member, and is coupled to the contracting mechanism. A first portion of the sleeve longitudinally extends from the first sleeve end toward the first site, and a second portion of the sleeve longitudinally extends from the second sleeve end toward the second site. The sleeve is arranged in a closed loop, such that the first and second portions of the sleeve together define a longitudinally overlapping portion of the sleeve. The implantable structure is configured such that the contracting assembly applies a longitudinal contracting force only between the first and the second sites, and not along the overlapping portion. The longitudinal contracting force longitudinally contracts at least a portion of the sleeve only between the first and the second sites, and not along the overlapping portion. Typically, the contracting member extends along neither the first nor the second portion of the sleeve.

In some applications of the present invention, the contracting assembly includes one or more longitudinal contracting members coupled to the contracting mechanism. The implantable structure is placed completely around an annulus of an atrioventricular valve of a subject, such that none of the one or more longitudinal contracting members is positioned along an anterior portion of the annulus between fibrous trigones of the valve. The implantable structure is fastened to the annulus. The contracting assembly is then actuated to contract a longitudinal portion of the sleeve not positioned along the anterior portion of the annulus. Tightening of the implantable structure therefore tightens at least a portion of the posterior portion of the annulus, while preserving the length of the anterior portion of the annulus. (The anterior portion of the annulus should generally not be contracted because its tissue is part of the skeleton of the heart.) However, the portion of the sleeve deployed along the anterior portion of the annulus prevents dilation of the anterior annulus, because the sleeve is anchored at both ends of the anterior annulus, and the sleeve typically comprises a longitudinally non-extensible material. This deployment configuration may help prevent long-term resizing of annulus, especially the anterior annulus, which sometimes occurs after implantation of partial annuloplasty rings, such as C-bands.

In some applications of the present invention, one or more of the tissue anchors are coupled to the sleeve at respective third sites longitudinally between the second site and the second sleeve end, exclusive. Typically, the implantable structure is configured such that the contracting assembly applies a longitudinal contracting force only between the first and the second sites. The longitudinal contracting force contracts at least a portion of the sleeve only between the first and the second sites. Providing the one or more anchors beyond the ends of the contracting member generally distributes force applied by contraction of the contracting assembly over the tissue interfaces of these anchors. In contrast, in some configurations of the implantable structure in which anchors are not provided beyond the ends of the contracting member, the force applied by the contracting assembly is applied predominantly to the single anchor nearest the first end of the contracting member, and the single anchor nearest the second end of the contracting member.

For some applications, at least two of the tissue anchors are coupled to the sleeve at respective third sites longitudinally between the second member end and the second sleeve end, exclusive. For some applications, the second site is at least 5 mm from the second sleeve end, measured when the sleeve is in a straight, relaxed, non-contracted state, such as at least 9 mm, e.g., at least 18 mm. For some applications, the second site is at a longitudinal distance from the second sleeve end, which distance is no greater than 30% of a total length of the sleeve, the distance and length measured when the sleeve is in the straight, relaxed, non-contracted state. For some applications, at least three of the tissue anchors are coupled to the sleeve alongside the contracting member, longitudinally between the first and second sites, exclusive. Typically, the sleeve is substantially longitudinally non-extensible.

For some applications, the sleeve has first and second sleeve ends, and first and second portions that longitudinally extend from the first and the second sleeve ends, respectively. The sleeve is arranged in a closed loop, such that the first and second portions of the sleeve together define a longitudinally overlapping portion of the sleeve positioned at least partially along the anterior portion of the annulus, and none of the one or more longitudinal contracting members is positioned along the overlapping portion of the sleeve. For some applications, at least one of the tissue anchors penetrates both the first and second portions of the sleeve at the overlapping portion. Such a mutual anchor helps ensure that the first and second portions remain tightly coupled together and to the tissue, so that the sleeve retains its closed loop shape. Alternatively, for some applications, the sleeve is shaped so as to define an integrally closed loop having no sleeve ends.

The implantable structure, when in this closed-loop configuration, is deployed around the entire annulus of the native valve, including an anterior portion of the annulus (on the aortic side of the valve) between the fibrous trigones. Typically, the contracting member does not extend along the portion of the sleeve deployed along the anterior portion of the annulus, and thus does not extend along the first portion, the second portion, or the overlapping portion of the sleeve. The portion of the sleeve deployed along the anterior portion of the annulus (between the trigones) is thus non-contractible. As mentioned above, tightening of the implantable structure therefore tightens the posterior portion of the annulus, while preserving the length of the anterior portion of the annulus. For some applications, this deployment configuration may also help achieve a closed loop that serves as a base ring to which a prosthetic valve is coupled.

In some applications of the present invention, the implantable structure further comprises an elongated linking member, which is positioned along an anterior portion of the annulus, so as to join the ends of the implantable structure in a complete loop. Over time after implantation, the linking member becomes fixed to the anterior portion of the annulus, thereby helping prevent long-term dilation of the anterior annulus. Typically, at least a portion of the linking member is disposed within and covered by the sleeve, into and/or over which fibrous tissue grows over time, helping anchor the linking member to tissue of the anterior annulus. Typically, in this configuration of the implantable structure, none of the anchors is coupled to the anterior portion of the annulus.

A first end of the linking member is typically fixed between 2 and 6 cm from a first end of the sleeve. A second end of the linking member is positioned within 1.5 cm of the same end of the sleeve, either protruding from the end of the sleeve, or recessed within the sleeve. The second end of the linking member comprises (e.g., is shaped so as to define) a first coupling element. The implantable structure further comprises a second coupling element, which is configured to be coupleable to the first coupling element. The second coupling element is coupled to the implantable structure within 1.5 cm of the second end of the sleeve. The second coupling element may be coupled to the housing, directly to the sleeve, or otherwise coupled to the implantable structure. Typically, the linking member is substantially longitudinally non-extensible, i.e., its length is fixed.

For some applications, the linking member is configured as a spring, which is typically curved, so as to be elastic in a radial direction, i.e., to be compressible like a bow or deflected beam. In these applications, the linking member is oriented such that it is pressed by elasticity against the anterior portion of the mitral annulus, i.e., the outer wall of the aorta, thereby holding the sleeve covering the linking member against the aortic wall. For some applications, at least two of the tissue anchors are coupled to the sleeve at respective, different longitudinal sites alongside the linking member, within 6 cm of the first end of the linking member. These tissue anchors may help set the proper direction of curvature of the linking member, for applications in which the linking member is curved.

For some applications, the implantable structure further comprises an elongated radial-force application element, which is disposed entirely within a first longitudinal portion of the sleeve. The elongated radial-force application element is configured to apply a force against a wall of the first longitudinal portion of the sleeve in at least one radially-outward direction. The applied force pushes the first longitudinal portion of the sleeve against tissue of the left atrium, such as against tissue of the annulus and/or the atrial wall, so as to inhibit blood flow between the sleeve and the tissue. It is generally desirable to inhibit blood flow between the sleeve and the annulus on anterior side, to avoid creating turbulence. When implanting the implantable structure, the elongated radial-force application element is placed along the anterior portion of the annulus, between the fibrous trigones.

For some applications, the elongated radial-force application element comprises a springy element. For some applications, at least a portion of the springy element is curved at least partially about an inner surface of the wall of the sleeve.

For some applications, the elongated radial-force application element is rotationally asymmetric and not helically symmetric. For other applications, the elongated radial-force application element is helically symmetric; for these applications, the springy element typically comprises a coiled spring.

For some applications, the sleeve has first and second sleeve ends. For some applications, the elongated radial-force application element has (a) a first radial-force-application-element longitudinal end that is between 2 and 6 cm from the first sleeve end, measured when the sleeve is fully longitudinally extended, and (b) a second radial-force-application-element longitudinal end that is within 1.5 cm of the first sleeve end, measured when the sleeve is fully longitudinally extended.

For some applications, the annuloplasty ring further comprises (a) a first coupling element, which is coupled to the annuloplasty ring within 1.5 cm of the first sleeve end, measured when the sleeve is fully longitudinally extended, and (b) a second coupling element. The second coupling element is configured to be coupleable to the first coupling element, and is fixed to the implantable structure (e.g., the annuloplasty ring) within 1.5 cm of the second sleeve end, measured when the sleeve is fully longitudinally extended. For some applications, at least one of the first and second coupling elements comprises a hook.

For some applications, the contracting mechanism (e.g., the housing thereof) is fixed along the sleeve within 30 mm, such as within 15 mm, of the second sleeve end (i.e., the same end of the sleeve near which the second coupling element is coupled), measured when the sleeve is fully longitudinally extended. For example, the contracting mechanism (e.g., the housing thereof) may be fixed at the second sleeve end. Alternatively, for some applications, the contracting mechanism (e.g., the housing thereof) is fixed at least 5 mm from the second sleeve end, e.g., between 5 and 30 mm, such as between 5 and 15 mm, from the second sleeve end. The second coupling element may be coupled to the contracting mechanism (e.g., to the housing).

For some applications, the annuloplasty ring further comprises a substantially longitudinally non-extensible linking member, i.e., a length thereof is substantially constant, i.e., cannot be longitudinally stretched, under normal usage conditions. The linking member typically helps prevent long-term dilation of the anterior annulus. The linking member is typically configured not to apply any force to the wall of the first longitudinal portion of the sleeve. Typically, the linking member is not configured as a spring.

For some applications, at least the first longitudinal portion of the sleeve is substantially longitudinally non-extensible, i.e., a length thereof is substantially constant, i.e., cannot be longitudinally stretched, under normal usage conditions. In these applications, the first longitudinal portion typically helps prevent long-term dilation of the anterior annulus. For some applications, the first coupling element is fixed to the wall of the sleeve within 1.5 cm of first sleeve end 51, measured when the sleeve is fully longitudinally extended. The implantable structure typically does not comprise the linking member in these applications. In these applications, at least the first longitudinal portion of the sleeve is substantially longitudinally non-extensible, and the first longitudinal portion typically helps prevent long-term dilation of the anterior annulus.

For some applications, during placement, after fastening the sleeve to the portion of the annulus, the healthcare professional twists the first longitudinal portion of the sleeve. Optionally, such twisting may serve one or both of the following purposes: (1) the twisting may store energy in the springy element for exertion of torque against the wall of the sleeve, and (2) the twisting may rotationally align the springy element in the desired radial direction. Alternatively or additionally to twisting for the first of these purposes, the springy element may be pre-loaded (twisted) to store energy before implantation in the subject, such as immediately before implantation or during manufacture.

For some applications, the sleeve is fastened to the annulus by coupling a plurality of tissue anchors to the annulus. The tissue anchors are coupled with:
  a first non-zero longitudinal density along a posterior portion of the annulus between the left and right fibrous trigones of the annulus, including the trigones, which density is equal to (a) a number of the tissue anchors coupled to the annulus along the posterior portion of the annulus divided by (b) a length of the posterior portion of the annulus (measured along the annulus),
  and a second non-zero longitudinal density along the anterior portion of the annulus between the left and right fibrous trigones of the annulus, not including the trigones, which density is equal to (a) a number of the tissue anchors coupled to the annulus along the anterior portion of the annulus divided by (b) a length of the anterior portion of the annulus (measured along the annulus).

The first longitudinal density is greater than the second longitudinal density. For some applications, the first longitudinal density is at least twice the second longitudinal density, such as at least 2.5 the second longitudinal density, e.g., at least 3 times the second longitudinal density. After the tissue anchors are fastened to the annulus, a longitudinal portion of the sleeve is contracted, such as by causing the longitudinal contracting member to apply a force to the longitudinal portion of the sleeve, such as by actuating the contracting assembly.

For some applications, the sleeve is fastened to the annulus by coupling a plurality of tissue anchors to the annulus, including first, second, and third tissue anchors, as follows:
  one or more first tissue anchors are coupled to the annulus along a lateral scallop (P1) of the posterior leaflet, with a first longitudinal density, which density is equal to (a) a number of the first tissue anchors coupled to the annulus along the lateral scallop (P1) divided by (b) a length of the lateral scallop (P1) along the annulus,
  a plurality of second tissue anchors (e.g., at least 3 tissue anchors) are coupled to the annulus along a middle scallop (P2) of the posterior leaflet, with a second longitudinal density, which density is equal to (a) a number of the second tissue anchors coupled to the annulus along the middle scallop (P2) divided by (b) a length of the middle scallop (P2) along the annulus, and
  one or more third tissue anchors are coupled to the annulus along a medial scallop (P3) of the posterior leaflet, with a third longitudinal density, which density is equal to (a) a number of the third tissue anchors coupled to the annulus along the medial scallop (P3) divided by (b) a length of the medial scallop (P3) along the annulus.

The longitudinal densities are characterized by at least one of the following: (a) the second longitudinal density is at least twice the first longitudinal density, and (b) the second longitudinal density is at least twice the third longitudinal density. For some applications, both (a) the second longitudinal density is at least twice the first longitudinal density, and (b) the second longitudinal density is at least twice the third longitudinal density.

For some applications, the tissue anchors, including the second tissue anchors, comprise respective anchor heads and tissue coupling elements. Typically, the anchor heads are circular; alternatively, they have another shape, such as of an ellipse or a polygon (e.g., a hexagon or a square). The plurality of tissue anchors are coupled to the annulus such that, after the longitudinal portion of the sleeve has been contracted, each of the anchor heads of at least two of the second tissue anchors coupled along the middle scallop (P2) touches at least one longitudinally-adjacent anchor head; for example, each of the anchor heads of at least three of tissue anchors touches at least one longitudinally-adjacent anchor head 320.

Typically, before the longitudinal portion of the sleeve has been contracted, the anchor heads of the at least two of the second tissue anchors do not touch any longitudinally-adjacent the anchor heads. Before the longitudinal portion of the sleeve has been contracted, the anchors are coupled to the sleeve and tissue at distances between the anchors that are less than the planned distances that the anchors move toward each other during contraction of the longitudinal portion of the sleeve. As a result, the anchor heads touch each other upon such contraction.

This touching of the longitudinally-adjacent anchors heads inhibits longitudinal contraction of the sleeve in the longitudinal area of these anchors, so as to facilitate reshaping of the annulus in a desired manner. These longitudinally-adjacent the anchor heads thus are dual-function, and serve to both anchor their respective anchors to the sleeve and to inhibit contraction of the sleeve.

For some applications, the plurality of tissue anchors is coupled to the annulus such that, after the longitudinal portion of the sleeve has been contracted:

none of the anchor heads of the first tissue anchors coupled along the lateral scallop (P1) touches any of the other anchor heads of the tissue anchors; and/or none of the anchor heads of the third tissue anchors coupled along the medial scallop (P3) touches any of the other anchor heads of the tissue anchors.

For some applications, the plurality of tissue anchors are coupled to the annulus such that, after the longitudinal portion of the sleeve has been contracted:

a first number of the anchor heads of the first tissue anchors coupled along the lateral scallop (P1) touch at least one longitudinally-adjacent anchor head, and (b) a second number of the anchors heads of the tissue anchors coupled along the middle scallop (P2) touch at least one longitudinally-adjacent anchor head, the second number greater than the first number; and/or a second number of the anchor heads of the second tissue anchors coupled along the middle scallop (P2) touch at least one longitudinally-adjacent anchor head, and (b) a third number of the anchors heads of the third tissue anchors coupled along the medial scallop (P3) touch at least one longitudinally-adjacent anchor head, the second number greater than the third number.

For some applications, the sleeve is fastened to the annulus by coupling a plurality of tissue anchors to the annulus, such that:

a first set of exactly three of the tissue anchors is disposed in succession along a first portion of the longitudinal contracting member with a first distance between longitudinal-end tissue anchors of the first set, measured along the annulus, and a second set of exactly three of the tissue anchors is disposed in succession along a second portion of the longitudinal contracting member with a second distance between longitudinal-end tissue anchors of the second set, measured along the annulus, The first distance equals at least twice the second distance, such as at least 2.5 times the second distance, e.g., at least 3 times the second distance. The first distance is measured between closest portions of the longitudinal-end tissue anchors of the first set, and the second distance is measured between closest portions of the longitudinal-end tissue anchors of the second set. The first and second sets do not share any common tissue anchors. After the tissue anchors are fastened to the annulus, a longitudinal portion of the sleeve is contracted. Providing the greater number of anchoring points with the second set better distributes forces among the anchors of this set.

For some applications, the contracting mechanism comprises a rotatable structure, and a housing in which the rotatable structure is positioned. The contracting mechanism and the longitudinal contracting member are arranged such that rotation of the rotatable structure contracts the implantable structure. Typically, an anchor deployment manipulator is advanced into a lumen of the sleeve, and, from within the lumen, deploys the anchors through a wall of the sleeve and into cardiac tissue, thereby anchoring the sleeve around a portion of a valve annulus.

For some applications, the implantable structure comprises an adjustable annuloplasty ring for repairing a dilated valve annulus of an atrioventricular valve, such as a mitral valve. The annuloplasty ring may be used for treating functional mitral regurgitation (FMR) or degenerative mitral valve disease. For other applications, a prosthetic heart valve is further provided, which is configured to be coupled to the sleeve.

For some applications in which the implantable structure is implanted around the annulus of a valve, the implantable structure may be advanced toward the annulus of a valve in any suitable procedure, e.g., a transcatheter procedure, a percutaneous procedure, a minimally invasive procedure, or an open heart procedure.

There is therefore provided, in accordance with an application of the present invention, a method including:

providing an annuloplasty ring, which includes (a) a flexible sleeve, and (b) a contracting assembly;

during a percutaneous transcatheter procedure, placing the flexible sleeve entirely around an annulus of a mitral valve of a subject in a closed loop;

fastening the sleeve to the annulus by coupling a plurality of tissue anchors to a posterior portion of the annulus, without coupling any tissue anchors to an anterior portion of the annulus between left and right fibrous trigones of the annulus; and thereafter, contracting a longitudinal portion of the sleeve.

For some applications, the contracting assembly further includes a longitudinal contracting member and a locking mechanism, and the method further includes, after contracting the longitudinal portion of the sleeve, locking the longitudinal contracting member with respect to the contracting assembly using the locking mechanism.

For some applications, contracting the longitudinal portion of the sleeve includes actuating the contracting assembly to contract the longitudinal portion of the sleeve.

For some applications, providing the annuloplasty ring includes providing the annuloplasty ring in which the sleeve is shaped so as to define an integrally closed loop having no sleeve ends.

For some applications, the sleeve has first and second sleeve ends, and placing the sleeve includes introducing the flexible sleeve into a left atrium while the first and the second sleeve ends are not coupled to each other; and thereafter, in the left atrium, arranging the flexible sleeve entirely around the annulus to form the closed loop.

For some applications, the annuloplasty ring further includes an elongated linking member, which is coupled to and disposed within the sleeve, and placing the flexible sleeve entirely around the annulus includes placing the linking member along the anterior portion of the annulus.

For some applications, the linking member is configured as a spring. For some applications, the linking member is curved. For some applications, the linking member has a length of between 2 and 6 cm. For some applications, the linking member includes metal. For some applications, the linking member is substantially longitudinally non-extensible.

For some applications:

the linking member includes a first coupling element, the annuloplasty ring includes a second coupling element, which is configured to be coupleable to the first coupling element, and which is coupled to the annuloplasty ring within 1.5 cm of one of the first and the second sleeve ends, measured when the sleeve is fully longitudinally extended, the first and the second coupling elements are configured to provide an adjustable-length connection between the linking member and the one of the first and the second sleeve ends, and placing the linking member along the anterior portion of the annulus includes setting an effective length of the linking member while coupling the first and the second coupling elements together.

For some applications:
the linking member is disposed within a longitudinal portion of the sleeve,
the annuloplasty ring further includes an elongated radial-force application element, which is disposed within the longitudinal portion of the sleeve, and
placing the linking member includes placing the elongated radial-force application element along the anterior portion of the annulus, such that the elongated radial-force application element applies a force against a wall of the longitudinal portion of the sleeve in at least one radially-outward direction.

For some applications, placing the elongated radial-force application element includes placing the elongated radial-force application element along the anterior portion of the annulus, such that the elongated radial-force application element pushes the longitudinal portion of the sleeve against atrial tissue.

For some applications, the elongated radial-force application element is springy.

For some applications, the elongated radial-force application element includes an inflatable element.

For some applications, the linking member is not configured as a spring.

For some applications, placing the linking member includes placing the linking member such that the linking member does not apply any force to the wall of the longitudinal portion of the sleeve.

For some applications, at least 90% of a length of the linking member is straight when in a resting state.

For some applications, the linking member is substantially longitudinally non-extensible.

For some applications, the elongated radial-force application element has a length of between 2 and 6 cm, measured when the sleeve is fully longitudinally extended.

For some applications:
the longitudinal portion of the sleeve is a first longitudinal portion of the sleeve,
the contracting assembly includes (a) a contracting mechanism, and (b) a longitudinal contracting member, which is arranged along a second longitudinal portion of the sleeve that is entirely longitudinally distinct from the first longitudinal portion of the sleeve, and
the elongated radial-force application element is disposed entirely within the first longitudinal portion of the sleeve.

There is further provided, in accordance with an application of the present invention, a method including:
providing an annuloplasty ring, which includes (a) a flexible sleeve, and (b) a contracting assembly;
during a percutaneous transcatheter procedure, placing the flexible sleeve entirely around an annulus of a mitral valve of a subject in a closed loop;
fastening the sleeve to the annulus by coupling a plurality of tissue anchors to the annulus, with:
a first non-zero longitudinal density of the tissue anchors along a posterior portion of the annulus between left and right fibrous trigones of the annulus, including the trigones, which density is equal to (a) a number of the tissue anchors coupled to the annulus along the posterior portion of the annulus divided by (b) a length of the posterior portion of the annulus, and
a second non-zero longitudinal density of the tissue anchors along an anterior portion of the annulus between left and right fibrous trigones of the annulus, not including the trigones, which density is equal to (a) a number of the tissue anchors coupled to the annulus along the anterior portion of the annulus divided by (b) a length of the anterior portion of the annulus, wherein the first longitudinal density is greater than the second longitudinal density; and
thereafter, contracting a longitudinal portion of the sleeve.

For some applications, the contracting assembly further includes a longitudinal contracting member and a locking mechanism, and the method further includes, after contracting the longitudinal portion of the sleeve, locking the longitudinal contracting member with respect to the contracting assembly using the locking mechanism.

For some applications, contracting the longitudinal portion of the sleeve includes actuating the contracting assembly to contract the longitudinal portion of the sleeve.

For some applications, the first longitudinal density is at least twice the second longitudinal density.

For some applications, providing the annuloplasty ring includes providing the annuloplasty ring in which the sleeve is shaped so as to define an integrally closed loop having no sleeve ends.

For some applications, the sleeve has first and second sleeve ends, and placing the flexible sleeve includes introducing the flexible sleeve into a left atrium while the first and the second sleeve ends are not coupled to each other; and thereafter, in the left atrium, arranging the flexible sleeve entirely around the annulus to form the closed loop.

For some applications, the annuloplasty ring further includes an elongated linking member, which is coupled to and disposed within the sleeve, and placing the flexible sleeve entirely around the annulus includes placing the linking member along the anterior portion of the annulus.

For some applications, the linking member has a length of between 2 and 6 cm.

For some applications, the linking member includes metal.

For some applications, the linking member is substantially longitudinally non-extensible.

For some applications:
the linking member includes a first coupling element,
the annuloplasty ring includes a second coupling element, which is configured to be coupleable to the first coupling element, and which is coupled to the annuloplasty ring within 1.5 cm of one of the first and the second sleeve ends, measured when the sleeve is fully longitudinally extended,
the first and the second coupling elements are configured to provide an adjustable-length connection between the linking member and the one of the first and the second sleeve ends, and
placing the linking member along the anterior portion of the annulus includes setting an effective length of the linking member while coupling the first and the second coupling elements together.

For some applications:
the linking member is disposed within a longitudinal portion of the sleeve,
the annuloplasty ring further includes an elongated radial-force application element, which is disposed within the longitudinal portion of the sleeve, and
placing the linking member includes placing the elongated radial-force application element along the anterior portion of the annulus, such that the elongated radial-force application element applies a force against a wall of the longitudinal portion of the sleeve in at least one radially-outward direction.

For some applications, placing the elongated radial-force application element includes placing the elongated radial-force application element along the anterior portion of the annulus, such that the elongated radial-force application element pushes the longitudinal portion of the sleeve against atrial tissue.

For some applications, the elongated radial-force application element is springy.

For some applications, the elongated radial-force application element includes an inflatable element.

For some applications, the linking member is not configured as a spring.

For some applications, placing the linking member includes placing the linking member such that the linking member does not apply any force to the wall of the longitudinal portion of the sleeve.

For some applications, at least 90% of a length of the linking member is straight when in a resting state.

For some applications, the linking member is substantially longitudinally non-extensible.

For some applications, the elongated radial-force application element has a length of between 2 and 6 cm, measured when the sleeve is fully longitudinally extended.

For some applications:
the longitudinal portion of the sleeve is a first longitudinal portion of the sleeve,
the contracting assembly includes (a) a contracting mechanism, and (b) a longitudinal contracting member, which is arranged along a second longitudinal portion of the sleeve that is entirely longitudinally distinct from the first longitudinal portion of the sleeve, and
the elongated radial-force application element is disposed entirely within the first longitudinal portion of the sleeve.

There is still further provided, in accordance with an application of the present invention, a method including:
providing an annuloplasty ring, which includes (a) a flexible sleeve, and (b) a contracting assembly;
during a percutaneous transcatheter procedure, placing the flexible sleeve at least partially around an annulus of a mitral valve of a subject;
fastening the sleeve to the annulus by coupling a plurality of tissue anchors to the annulus, with:
a first longitudinal density of the tissue anchors along a lateral scallop (P1) of a posterior leaflet of the mitral valve, which density is equal to (a) a number of the tissue anchors coupled to the annulus along the lateral scallop (P1) divided by (b) a length of the lateral scallop (P1) along the annulus,
a second longitudinal density of the tissue anchors along a middle scallop (P2) of the posterior leaflet, which density is equal to (a) a number of the tissue anchors coupled to the annulus along the middle scallop (P2) divided by (b) a length of the middle scallop (P2) along the annulus, and
a third longitudinal density of the tissue anchors along a medial scallop (P3) of the posterior leaflet, which density is equal to (a) a number of the tissue anchors coupled to the annulus along the medial scallop (P3) divided by (b) a length of the medial scallop (P3) along the annulus, wherein the longitudinal densities are characterized by at least one of the following: (a) the second longitudinal density is at least twice the first longitudinal density, and (b) the second longitudinal density is at least twice the third longitudinal density; and
thereafter, contracting a longitudinal portion of the sleeve.

For some applications, the contracting assembly further includes a longitudinal contracting member and a locking mechanism, and the method further includes, after contracting the longitudinal portion of the sleeve, locking the longitudinal contracting member with respect to the contracting assembly using the locking mechanism.

For some applications, contracting the longitudinal portion of the sleeve includes actuating the contracting assembly to contract the longitudinal portion of the sleeve.

For some applications, both (a) the second longitudinal density is at least twice the first longitudinal density, and (b) the second longitudinal density is at least twice the third longitudinal density.

For some applications, the second longitudinal density is at least twice the first longitudinal density.

For some applications, the second longitudinal density is at least twice the third longitudinal density.

For some applications, coupling the plurality of tissue anchors to the annulus includes coupling at least 3 tissue anchors to the annulus along the middle scallop (P2).

For some applications, the tissue anchors have respective anchor heads, and coupling the plurality of tissue anchors to the annulus includes coupling the plurality of tissue anchors to the annulus such that, after contracting the longitudinal portion of the sleeve, each of the anchor heads of at least two of the tissue anchors coupled along the middle scallop (P2) touches at least one longitudinally-adjacent anchor head.

For some applications, coupling the plurality of tissue anchors to the annulus includes coupling the plurality of tissue anchors to the annulus such that, before contracting the longitudinal portion of the sleeve, the anchor heads of the at least two of the tissue anchors do not touch the at least one longitudinally-adjacent anchor head.

For some applications, coupling the plurality of tissue anchors to the annulus includes coupling the plurality of tissue anchors to the annulus such that, after contracting the longitudinal portion of the sleeve, each of the anchor heads of at least three of the tissue anchors coupled along the middle scallop (P2) touches at least one longitudinally-adjacent anchor head.

For some applications, coupling the plurality of tissue anchors to the annulus includes coupling the plurality of tissue anchors to the annulus such that, after contracting the longitudinal portion of the sleeve, none of the anchor heads of the tissue anchors coupled along the lateral scallop (P1) touches any of the other anchor heads of the tissue anchors.

For some applications, coupling the plurality of tissue anchors to the annulus includes coupling the plurality of tissue anchors to the annulus such that, after contracting the longitudinal portion of the sleeve, none of the anchor heads of the tissue anchors coupled along the medial scallop (P3) touches any of the other anchor heads of the tissue anchors.

For some applications, coupling the plurality of tissue anchors to the annulus includes coupling the plurality of tissue anchors to the annulus such that, after contracting the longitudinal portion of the sleeve, (a) none of the anchor heads of the tissue anchors coupled along the lateral scallop (P1) touches any of the other anchor heads of the tissue anchors, and (b) none of the anchor heads of the tissue anchors coupled along the medial scallop (P3) touches any of the other anchor heads of the tissue anchors.

For some applications, coupling the plurality of tissue anchors to the annulus includes coupling the plurality of tissue anchors to the annulus such that, after contracting the longitudinal portion of the sleeve, (a) a first number of the anchor heads of the tissue anchors coupled along the lateral scallop (P1) touch at least one longitudinally-adjacent anchor head, and (b) a second number of the anchors heads of the tissue anchors coupled along the middle scallop (P2) touch at least one longitudinally-adjacent anchor head, the second number greater than the first number.

For some applications, coupling the plurality of tissue anchors to the annulus includes coupling the plurality of tissue anchors to the annulus such that, after contracting the longitudinal portion of the sleeve, (a) a second number of the anchor heads of the tissue anchors coupled along the middle scallop (P2) touch at least one longitudinally-adjacent anchor head, and (b) a third number of the anchors heads of the tissue anchors coupled along the medial scallop (P3) touch at least one longitudinally-adjacent anchor head, the second number greater than the third number.

For some applications, coupling the plurality of tissue anchors to the annulus includes coupling the plurality of tissue anchors to the annulus such that, after contracting the longitudinal portion of the sleeve:
- a first number of the anchor heads of the tissue anchors coupled along the lateral scallop (P1) touch at least one longitudinally-adjacent anchor head,
- a second number of the anchors heads of the tissue anchors coupled along the middle scallop (P2) touch at least one longitudinally-adjacent anchor head, and
- a third number of the anchors heads of the tissue anchors coupled along the medial scallop (P3) touch at least one longitudinally-adjacent anchor head, the second number greater than the first number, and the second number greater than the third number.

For some applications, the sleeve has first and second sleeve ends, and placing the sleeve includes introducing the flexible sleeve into a left atrium while the first and the second sleeve ends are not coupled to each other.

For some applications, placing the sleeve includes arranging the sleeve entirely around the annulus to form a closed loop, after introducing the flexible sleeve into the left atrium while the first and the second sleeve ends are not coupled to each other.

For some applications, providing the annuloplasty ring includes providing the annuloplasty ring in which the sleeve is shaped so as to define an integrally closed loop having no sleeve ends.

There is additionally provided, in accordance with an application of the present invention, a method including:
providing an annuloplasty ring, which includes (a) a flexible sleeve and (b) a contracting assembly, which includes a longitudinal contracting member;
during a percutaneous transcatheter procedure, placing the flexible sleeve at least partially around an annulus of a mitral valve of a subject;
fastening the sleeve to the annulus by coupling a plurality of tissue anchors to the annulus, such that:
a first set of exactly three of the tissue anchors is disposed in succession along the longitudinal contracting member with a first distance between longitudinal-end tissue anchors of the first set, measured along the annulus, and
a second set of exactly three of the tissue anchors is disposed in succession along the longitudinal contracting member with a second distance between longitudinal-end tissue anchors of the second set, measured along the annulus, wherein the first distance equals at least twice the second distance, and wherein the first and the second sets do not share any common tissue anchors; and thereafter, contracting a longitudinal portion of the sleeve by causing the longitudinal contracting member to apply a contracting force to the longitudinal portion of the sleeve.

For some applications, the contracting assembly further includes a locking mechanism, and the method further includes, after contracting the longitudinal portion of the sleeve, locking the longitudinal contracting member with respect to the contracting assembly using the locking mechanism.

For some applications, contracting the longitudinal portion of the sleeve includes actuating the contracting assembly to contract the longitudinal portion of the sleeve by causing the longitudinal contracting member to apply the contracting force to the longitudinal portion of the sleeve.

There is yet additionally provided, in accordance with an application of the present invention, apparatus including an annuloplasty ring, which includes:
a flexible sleeve, having first and second sleeve ends;
a contracting assembly;
a first coupling element, which is coupled to the annuloplasty ring within 1.5 cm of the first sleeve end, measured when the sleeve is fully longitudinally extended;
a second coupling element, which is configured to be coupleable to the first coupling element, and which is coupled to the annuloplasty ring within 1.5 cm of the second sleeve end, measured when the sleeve is fully longitudinally extended; and
an elongated springy element, which is disposed entirely within a longitudinal portion of the sleeve, wherein the springy element has (a) a first springy-element longitudinal end that is between 2 and 6 cm from the first sleeve end, measured when the sleeve is fully longitudinally extended, and (b) a second springy-element longitudinal end that is within 1.5 cm of the first sleeve end, measured when the sleeve is fully longitudinally extended,
wherein the springy element is configured to press the longitudinal portion of the sleeve against tissue.

For some applications, the contracting assembly further includes a longitudinal contracting member and a locking mechanism, which is configured to lock the longitudinal contracting member with respect to the contracting assembly.

For some applications, the longitudinal portion of the sleeve is a first longitudinal portion of the sleeve, and the contracting assembly is configured to contract at least a portion of a second longitudinal portion of the sleeve, which second longitudinal portion is entirely longitudinally distinct from the first longitudinal portion.

For some applications, a first end of the elongated springy element includes the first coupling element.

There is also provided, in accordance with an application of the present invention, a method including:
providing an annuloplasty ring, which includes (a) a flexible sleeve, having first and second sleeve ends, (b) a contracting assembly, (c) a first coupling element, which is coupled to the annuloplasty ring within 1.5 cm of the first sleeve end, measured when the sleeve is fully longitudinally extended, (d) a second coupling element, which is configured to be coupleable to the first coupling element, and which is coupled to the annuloplasty ring within 1.5 cm of the second sleeve end, measured when the sleeve is fully longitudinally extended, and (e) an elongated springy element, which is disposed entirely within a first longitudinal portion of the sleeve, wherein the springy element has (a) a first springy-element longitudinal end that is between 2 and 6 cm from the first sleeve end, measured when the sleeve is fully longitudinally extended, and (b) a second springy-element longitudinal end that is within 1.5 cm of the first sleeve end, measured when the sleeve is fully longitudinally extended;

during a percutaneous transcatheter procedure, placing the flexible sleeve around a portion of an annulus of an atrioventricular valve of a subject, which portion includes a posterior portion of the annulus;

placing the first longitudinal portion of the sleeve along an anterior portion of the annulus between fibrous trigones of the valve;

fastening the flexible sleeve to the portion of the annulus, such that the springy element presses the first longitudinal portion of the sleeve against tissue;

coupling the first and the second coupling elements together; and contracting at least a portion of a second longitudinal portion of the sleeve, which second longitudinal portion is entirely longitudinally distinct from the first longitudinal portion.

For some applications, the contracting assembly further includes a locking mechanism, and the method further includes, after contracting the at least a portion of the second longitudinal portion of the sleeve, locking the longitudinal contracting member with respect to the contracting assembly using the locking mechanism.

For some applications, contracting the at least a portion of the second longitudinal portion of the sleeve includes actuating the contracting assembly to contract the at least a portion of the second longitudinal portion of the sleeve.

For some applications, a first end of the elongated springy element includes the first coupling element.

There is further provided, in accordance with an application of the present invention, apparatus including an annuloplasty ring, which includes:

a flexible sleeve; and an elongated radial-force application element, which (a) is disposed entirely within a longitudinal portion of the sleeve, (b) which has a length of no more than 6 cm, measured when the sleeve is fully longitudinally extended, and (c) is configured to apply a force against a wall of the longitudinal portion of the sleeve in at least one radially-outward direction.

For some applications, the elongated radial-force application element is rotationally asymmetric and not helically symmetric.

For some applications, the elongated radial-force application element is configured to apply the force against the wall around less than 100% of a perimeter of the wall.

For some applications, the elongated radial-force application element is configured to apply the force against the wall around less than 50% of the perimeter of the wall.

For some applications, the elongated radial-force application element is configured to apply the force with a variation of less than 20% along a length of the elongated radial-force application element.

For some applications, the sleeve has first and second sleeve ends.

For some applications, the annuloplasty ring further includes:

a first coupling element, which is coupled to the annuloplasty ring within 1.5 cm of the first sleeve end, measured when the sleeve is fully longitudinally extended; and a second coupling element, which is configured to be coupleable to the first coupling element, and which is coupled to the annuloplasty ring within 1.5 cm of the second sleeve end, measured when the sleeve is fully longitudinally extended.

For some applications, the elongated radial-force application element has (a) a first radial-force-application-element longitudinal end that is between 2 and 6 cm from the first sleeve end, measured when the sleeve is fully longitudinally extended, and (b) a second radial-force-application-element longitudinal end that is within 1.5 cm of the first sleeve end, measured when the sleeve is fully longitudinally extended.

For some applications, the sleeve is shaped so as to define an integrally closed loop having no sleeve ends.

For some applications:

the annuloplasty ring further includes a contracting assembly, which includes a housing that is fixed to the sleeve, and the elongated radial-force application element has (a) a first radial-force-application-element longitudinal end that is between 2 and 6 cm from the housing, measured when the sleeve is fully longitudinally extended, and (b) a second radial-force-application-element longitudinal end that is within 1.5 cm of the housing, measured when the sleeve is fully longitudinally extended.

For some applications, the elongated radial-force application element is configured to push the longitudinal portion of the sleeve against atrial tissue.

For some applications, the annuloplasty ring further includes a substantially longitudinally non-extensible linking member, which has first and second linking-member ends and is at least partially disposed within the longitudinal portion of the sleeve, and the second linking-member end includes the first coupling element.

For some applications, the linking member has a length of between 2 and 6 cm.

For some applications, at least the longitudinal portion of the sleeve is substantially longitudinally non-extensible, and the first coupling element is fixed to the wall of the sleeve within 1.5 cm of the first sleeve end, measured when the sleeve is fully longitudinally extended.

For some applications, the elongated radial-force application element includes a springy element.

For some applications, where at least a portion of the springy element is curved at least partially about an inner surface of the wall of the sleeve.

For some applications, at least a portion of the springy element is serpentine.

For some applications, the at least a portion of the springy element is curved at least partially about the inner surface of the wall in a single circumferential direction.

For some applications, at least a first portion of the springy element is curved at least partially about the inner surface of the wall in a first circumferential direction, and at least a second portion of the springy element is curved at least partially about the inner surface of the wall in a second circumferential direction circumferentially opposite the first circumferential direction.

For some applications, at least a portion of the springy element is serpentine.

For some applications, springy element includes a coiled spring.

For some applications, the elongated radial-force application element includes an inflatable element.

For some applications,
the longitudinal portion of the sleeve is a first longitudinal portion of the sleeve, and
the annuloplasty ring further includes a longitudinal contracting member, which is arranged only along a second longitudinal portion of the sleeve that is entirely longitudinally distinct from the first longitudinal portion of the sleeve.

For some applications, the annuloplasty ring further includes a contracting assembly, which includes the longitudinal contracting member and a contracting mechanism.

For some applications, a first average internal diameter of the first longitudinal portion of the sleeve is greater than a second average internal diameter of the second longitudinal portion of the sleeve, when both the first and the second longitudinal portions are fully radially expanded.

For some applications, the first longitudinal portion of the sleeve is radially elastic, and the second longitudinal portion of the sleeve is substantially radially non-extensible.

For some applications, the first and the second longitudinal portions of the sleeve are substantially longitudinally non-extensible.

For some applications, the first and the second longitudinal portions of the sleeve have a same diameter when the first longitudinal portion is not elastically stretched.

For some applications, the first and the second longitudinal portions of the sleeve are woven, and the first longitudinal portion of the sleeve is more loosely woven than the second longitudinal portion of the sleeve.

For some applications, the first longitudinal portion of the sleeve is radially stretchable, and the second longitudinal portion of the sleeve is substantially radially non-extensible.

For some applications, the annuloplasty ring further includes a plurality of tissue anchors, at least two of which are coupled to the sleeve at respective, different longitudinal sites alongside the elongated radial-force application member.

For some applications, the annuloplasty ring further includes a contracting assembly, which includes a contracting mechanism and a longitudinal contracting member, and the contracting mechanism is fixed to the sleeve within 1.5 cm of the second sleeve end, measured when the sleeve is fully longitudinally extended.

For some applications, the second coupling element is coupled to the contracting mechanism.

For some applications, the longitudinal contracting member includes at least one wire.

For some applications, the elongated radial-force application member includes metal.

For some applications, the metal includes Nitinol.

For some applications, at least one of the first and second coupling elements includes a hook.

For some applications, at least one of the first and second coupling elements includes a loop.

There is still further provided, in accordance with an application of the present invention, a method including:
providing an annuloplasty ring, which includes (a) a flexible sleeve and (b) an elongated radial-force application element, which is disposed entirely within a longitudinal portion of the sleeve;
during a percutaneous transcatheter procedure, placing the flexible sleeve entirely around an annulus of an atrioventricular valve of a subject, such that the longitudinal portion of the sleeve is disposed along an anterior portion of the annulus between fibrous trigones of the valve; and
fastening the flexible sleeve at least to a posterior portion of the annulus, such that the elongated radial-force application element applies a force against the wall of the longitudinal portion of the sleeve in at least one radially-outward direction.

For some applications, the elongated radial-force application element is rotationally asymmetric and not helically symmetric.

For some applications, the elongated radial-force application element is configured to apply the force against the wall around less than 100% of a perimeter of the wall.

For some applications, the elongated radial-force application element is configured to apply the force against the wall around less than 50% of the perimeter of the wall.

For some applications, the elongated radial-force application element is configured to apply the force with a variation of less than 20% along a length of the elongated radial-force application element.

For some applications, the flexible sleeve has first and second sleeve ends, and placing the flexible sleeve includes introducing the flexible sleeve into a left atrium while the first and the second sleeve ends are not coupled to each other; and thereafter, in the left atrium, arranging the flexible sleeve entirely around the annulus to form the closed loop.

For some applications:
the annuloplasty ring further includes (a) a first coupling element, which is coupled to the annuloplasty ring within 1.5 cm of the first sleeve end, measured when the sleeve is fully longitudinally extended, (b) a second coupling element, which is configured to be coupleable to the first coupling element, and which is coupled to the annuloplasty ring within 1.5 cm of the second sleeve end, measured when the sleeve is fully longitudinally extended, and
coupling the first and the second sleeve ends to each other to form the closed loop includes coupling the first and the second coupling elements together.

For some applications, the elongated radial-force application element has (a) a first radial-force-application-element longitudinal end that is between 2 and 6 cm from the first sleeve end, measured when the sleeve is fully longitudinally extended, and (b) a second radial-force-application-element longitudinal end that is within 1.5 cm of the first sleeve end, measured when the sleeve is fully longitudinally extended, For some applications, providing the annuloplasty ring includes providing the annuloplasty ring in which the sleeve is shaped so as to define an integrally closed loop having no sleeve ends.

For some applications:
the annuloplasty ring further includes a contracting assembly, which includes a housing that is fixed to the sleeve, and
the elongated radial-force application element has (a) a first radial-force-application-element longitudinal end that is between 2 and 6 cm from the housing, measured when the sleeve is fully longitudinally extended, and (b) a second radial-force-application-element longitudinal end that is within 1.5 cm of the housing, measured when the sleeve is fully longitudinally extended.

For some applications, the elongated radial-force application element includes an inflatable element.

For some applications, placing the elongated radial-force application element includes placing the elongated radial-force application element along the anterior portion of the annulus, such that the elongated radial-force application element pushes the longitudinal portion of the sleeve against atrial tissue.

For some applications, the annuloplasty ring further includes a substantially longitudinally non-extensible linking member, which has first and second linking-member ends and is at least partially disposed within the longitudinal portion of the sleeve, and the second linking-member end includes the first coupling element.

For some applications, the linking member has a length of between 2 and 6 cm.

For some applications, at least the longitudinal portion of the sleeve is substantially longitudinally non-extensible, and the first coupling element is fixed to the wall of the sleeve within 1.5 cm of the first sleeve end, measured when the sleeve is fully longitudinally extended.

For some applications, the elongated radial-force application element includes a springy element.

For some applications, placing the longitudinal portion of the sleeve includes twisting the longitudinal portion of the sleeve after fastening the sleeve to the portion of the annulus.

For some applications, placing the longitudinal portion of the sleeve includes twisting the springy element after fastening the sleeve to the portion of the annulus.

For some applications, where at least a portion of the springy element is curved at least partially about an inner surface of the wall of the sleeve.

For some applications, at least a portion of the springy element is serpentine.

For some applications, the at least a portion of the springy element is curved at least partially about the inner surface of the wall in a single circumferential direction.

For some applications, at least a first portion of the springy element is curved at least partially about the inner surface of the wall in a first circumferential direction, and at least a second portion of the springy element is curved at least partially about the inner surface of the wall in a second circumferential direction circumferentially opposite the first circumferential direction.

For some applications, at least a portion of the springy element is serpentine.

For some applications, springy element includes a coiled spring.

For some applications, the longitudinal portion of the sleeve is a first longitudinal portion, and the method further includes, after fastening the flexible sleeve at least to a posterior portion of the annulus, contracting a second longitudinal portion of the sleeve that is entirely longitudinally distinct from the first longitudinal portion of the sleeve.

For some applications, the longitudinal portion of the sleeve is a first longitudinal portion of the sleeve, and the annuloplasty ring further includes a longitudinal contracting member, which is arranged only along a second longitudinal portion of the sleeve that is entirely longitudinally distinct from the first longitudinal portion of the sleeve.

For some applications, the annuloplasty ring further includes a contracting assembly, which includes the longitudinal contracting member and a contracting mechanism.

For some applications, a first average internal diameter of the first longitudinal portion of the sleeve is greater than a second average internal diameter of the second longitudinal portion of the sleeve, when both the first and the second longitudinal portions are fully radially expanded.

For some applications, the first longitudinal portion of the sleeve is radially elastic, and the second longitudinal portion of the sleeve is substantially radially non-extensible.

For some applications, the first and the second longitudinal portions of the sleeve are substantially longitudinally non-extensible.

For some applications, the first and the second longitudinal portions of the sleeve have a same diameter when the first longitudinal portion is not elastically stretched.

For some applications, the first and the second longitudinal portions of the sleeve are woven, and the first longitudinal portion of the sleeve is more loosely woven than the second longitudinal portion of the sleeve.

For some applications, the first longitudinal portion of the sleeve is radially stretchable, and the second longitudinal portion of the sleeve is substantially radially non-extensible.

For some applications, the annuloplasty ring further includes a contracting assembly, which includes a contracting mechanism and a longitudinal contracting member, and the contracting mechanism is fixed to the sleeve within 30 mm of the second sleeve end, measured when the sleeve is fully longitudinally extended.

For some applications, the second coupling element is coupled to the contracting mechanism.

For some applications, the longitudinal contracting member includes at least one wire.

For some applications, the springy member includes metal.

For some applications, the metal includes Nitinol.

For some applications, at least one of the first and second coupling elements includes a hook.

For some applications, at least one of the first and second coupling elements includes a loop.

There is additionally provided, in accordance with an application of the present invention, apparatus including an implantable structure, which includes:
  a flexible sleeve, having first and second sleeve ends;
  a contracting assembly;
  an elongated linking member, having a first and second linking member ends, which second linking member end includes a first coupling element, wherein the linking member is coupled to the sleeve such that (a) at least a portion of the linking member is disposed within the sleeve, and (b) the first linking member end is longitudinally between the second linking member end and the first sleeve end, exclusive; and a second coupling element, which is configured to be coupleable to the first coupling element, and which is coupled to the implantable structure within 1.5 cm of the first sleeve end, measured when the sleeve is fully longitudinally extended.

For some applications, the contracting assembly is configured to longitudinal contract the sleeve.

For some applications, the implantable structure further includes a plurality of tissue anchors, at least two of which are coupled to the sleeve at respective, different longitudinal sites alongside the linking member.

For some applications, the contracting assembly includes a contracting mechanism and a longitudinal contracting member, and the contracting mechanism is coupled to the sleeve within 1.5 cm of the first sleeve end.

For some applications, the second coupling element is coupled to the contracting mechanism.

For some applications, the longitudinal contracting member includes at least one wire.

For some applications, the linking member is configured as a spring.

For some applications, the linking member is curved.

For some applications, the linking member has a length of between 2 and 6 cm.

For some applications, the linking member includes metal.

For some applications, the metal includes Nitinol.

For some applications, the linking member is substantially longitudinally non-extensible.

For some applications, at least 30% of a length of the linking member is disposed within the sleeve.

For some applications, at least 75% of the length of the linking member is disposed within the sleeve.

For some applications, the flexible sleeve is a first flexible sleeve, the implantable structure further includes a second flexible sleeve, and at least 20% of a length of the linking member is disposed within the second flexible sleeve.

For some applications, at least one of the first and second coupling elements includes a hook.

For some applications, at least one of the first and second coupling elements includes a loop.

For some applications, the at least a portion of the linking member is disposed within a longitudinal portion of the sleeve, and the implantable structure further includes an elongated springy element, which is disposed within the longitudinal portion of the sleeve, and which is configured to apply a force against a wall of the longitudinal portion of the sleeve in at least one radially-outward direction.

For some applications, the linking member is not configured as a spring.

For some applications, the linking member is configured not to apply any force to the wall of the longitudinal portion of the sleeve.

For some applications, at least 90% of a length of the linking member is straight when in a resting state.

For some applications, the linking member is substantially longitudinally non-extensible.

For some applications, the springy element has a length of between 2 and 6 cm, measured when the sleeve is fully longitudinally extended.

For some applications:
the longitudinal portion of the sleeve is a first longitudinal portion of the sleeve,
the contracting assembly includes (a) a contracting mechanism, and (b) a longitudinal contracting member, which is arranged only along a second longitudinal portion of the sleeve that is entirely longitudinally distinct from the first longitudinal portion of the sleeve, and
the springy element is disposed entirely within the first longitudinal portion of the sleeve.

For some applications, the first and the second coupling elements are configured to provide an adjustable-length connection between the linking member and the first sleeve end.

There is yet additionally provided, in accordance with an application of the present invention, a method including:
providing an implantable structure, which includes (a) a flexible sleeve, having first and second sleeve ends, (b) a contracting assembly, (c) an elongated linking member, having a first and second linking member ends, which second linking member end includes a first coupling element, wherein the linking member is coupled to the sleeve such that (i) at least a portion of the linking member is disposed within the sleeve, and (ii) the first linking member end is longitudinally between the second linking member end and the first sleeve end, exclusive, and (d) a second coupling element, which is coupled to the implantable structure within 1.5 cm of the first sleeve end, measured when the sleeve is fully longitudinally extended;
during a percutaneous transcatheter procedure, placing the flexible sleeve around a portion of an annulus of an atrioventricular valve of a subject, which portion includes a posterior portion of the annulus;
placing the linking member along an anterior portion of the annulus between fibrous trigones of the valve;
fastening the flexible sleeve to the portion of the annulus;
coupling the first and the second coupling elements together; and
contracting a longitudinal portion of the sleeve.

For some applications, the contracting assembly further includes a locking mechanism, and the method further includes, after contracting the longitudinal portion of the sleeve, locking the longitudinal contracting member with respect to the contracting assembly using the locking mechanism.

For some applications, contracting the second longitudinal portion of the sleeve includes actuating the contracting assembly to contract the longitudinal portion of the sleeve.

For some applications, fastening includes fastening the sleeve to the annulus using a plurality of tissue anchors, including coupling at least two of the anchors to the sleeve and tissue of the annulus at respective, different longitudinal sites alongside the linking member.

For some applications, the contracting assembly includes a contracting mechanism and a longitudinal contracting member, and the contracting mechanism is coupled to the sleeve within 1.5 cm of the first sleeve end.

For some applications, the second coupling element is coupled to the contracting mechanism.

For some applications, the linking member is configured as a spring.

For some applications, the linking member is curved.

For some applications, the linking member has a length of between 2 and 6 cm.

For some applications, the linking member includes metal.

For some applications, the metal includes Nitinol.

For some applications, the linking member is substantially longitudinally non-extensible.

For some applications, at least 30% of a length of the linking member is disposed within the sleeve.

For some applications, at least 75% of the length of the linking member is disposed within the sleeve.

For some applications, the flexible sleeve is a first flexible sleeve, the implantable structure further includes a second flexible sleeve, and at least 20% of a length of the linking member is disposed within the second flexible sleeve.

For some applications, at least one of the first and second coupling elements includes a hook.

For some applications, at least one of the first and second coupling elements includes a loop.

For some applications:
the at least a portion of the linking member is disposed within a longitudinal portion of the sleeve,
the implantable structure further includes an elongated springy element, which is disposed within the longitudinal portion of the sleeve, and
placing the linking member includes placing the springy element along the anterior portion of the annulus, such that the springy element applies a force against a wall of the longitudinal portion of the sleeve in at least one radially-outward direction.

For some applications, the linking member is not configured as a spring.

For some applications, placing the linking member includes placing the linking member such that the linking member does not apply any force to the wall of the longitudinal portion of the sleeve.

For some applications, at least 90% of a length of the linking member is straight when in a resting state.

For some applications, the linking member is substantially longitudinally non-extensible.

For some applications, the springy element has a length of between 2 and 6 cm, measured when the sleeve is fully longitudinally extended.

For some applications:
the longitudinal portion of the sleeve is a first longitudinal portion of the sleeve,
the contracting assembly includes (a) a contracting mechanism, and (b) a longitudinal contracting member, which is arranged only along a second longitudinal portion of the sleeve that is entirely longitudinally distinct from the first longitudinal portion of the sleeve, and
the springy element is disposed entirely within the first longitudinal portion of the sleeve.

For some applications, the first and the second coupling elements are configured to provide an adjustable-length connection between the linking member and the first sleeve end, and placing the linking member along the anterior portion of the annulus includes setting an effective length of the linking member while coupling the first and the second coupling elements together.

There is also provided, in accordance with an application of the present invention, apparatus including an annuloplasty system, which includes:
an implantable structure, which includes a flexible sleeve, having first and second sleeve ends;
a linking bridge element, which includes first and second bridge coupling interfaces, which are configured to be coupled to the sleeve in order to link the first and the second sleeve ends via the linking bridge element; and
first and second flexible longitudinal guide members, which (a) are removably coupled to the sleeve within 1.5 cm of the first and the second sleeve ends, respectively, measured when the sleeve is fully longitudinally extended, and (b) extend from the first and the second sleeve ends, respectively, away from the sleeve, and (c) removably pass through respective openings defined by the linking bridge member, so as to guide the first and the second bridge coupling interfaces to corresponding locations on the sleeve.

For some applications, the respective openings defined by the linking bridge member are defined by the first and the second bridge coupling interfaces, respectively.

For some applications, the sleeve includes first and second sleeve coupling interfaces, to which the first and the second bridge coupling interfaces are configured to be coupled, respectively.

For some applications, the first and the second sleeve coupling interfaces are disposed within 1.5 cm of the first and the second sleeve ends, respectively, measured when the sleeve is fully longitudinally extended.

For some applications, the linking bridge element has a length of between 1 and 5 cm.

For some applications, the implantable structure includes a longitudinal contracting member, which is configured to longitudinally contract a longitudinal portion of the sleeve, and the first and the second flexible longitudinal guide members are separate and distinct from the longitudinal contracting member.

For some applications, wherein, when the first and the second flexible longitudinal guide members are removably coupled to the sleeve, the first and the second flexible longitudinal guide members do not longitudinally overlap the longitudinal contracting member.

For some applications, wherein, when the first and the second flexible longitudinal guide members are removably coupled to the sleeve, no portion of either the first flexible longitudinal guide member or the second flexible longitudinal guide member is disposed more than 1.5 cm from the first and the second sleeve ends, respectively, measured when the sleeve is fully longitudinally extended.

For some applications, wherein, when the first and the second flexible longitudinal guide members are removably coupled to the sleeve, the first and the second flexible longitudinal guide members are collectively disposed along less than 30% of a length of the sleeve, measured when the sleeve is fully longitudinally extended.

There is further provided, in accordance with an application of the present invention, a method including:
during a percutaneous transcatheter procedure, placing a flexible sleeve of an implantable structure partially around an annulus of a mitral valve of a subject, such that first and second flexible longitudinal guide members, which are removably coupled to the sleeve, extend from first and second sleeve ends of the sleeve, respectively, away from the sleeve, wherein the longitudinal guide members are removably coupled to the sleeve within 1.5 cm of the first and the second sleeve ends of the sleeve, respectively, measured when the sleeve is fully longitudinally extended;
advancing a linking bridge element into a left atrium of the subject, while the longitudinal guide members removably pass through respective openings defined by the linking bridge member;
using the first and the second longitudinal guide members to guide first and second bridge coupling interfaces of the linking bridge member to corresponding locations on the sleeve; and coupling the linking bridge member to the sleeve by coupling the first and the second bridge coupling interfaces to the sleeve, in order to link the first and the second sleeve ends via the linking bridge element.

For some applications, the respective openings defined by the linking bridge member are defined by the first and the second bridge coupling interfaces, respectively.

For some applications, the sleeve includes first and second sleeve coupling interfaces, and coupling the first and the second bridge coupling interfaces to the sleeve includes coupling the first and the second bridge coupling interfaces to the sleeve to the first and the second sleeve coupling interfaces, respectively.

For some applications, the first and the second sleeve coupling interfaces are disposed within 1.5 cm of the first and the second sleeve ends, respectively, measured when the sleeve is fully longitudinally extended.

For some applications, the linking bridge element has a length of between 1 and 5 cm.

For some applications:
the implantable structure includes a longitudinal contracting member,
the first and the second flexible longitudinal guide members are separate and distinct from the longitudinal contracting member, and
the method further includes, after coupling the linking bridge member to the sleeve, contracting a longitudinal portion of the sleeve by causing the longitudinal contracting member to apply a contracting force to the longitudinal portion of the sleeve.

For some applications, wherein, when the first and the second flexible longitudinal guide members are removably coupled to the sleeve, the first and the second flexible longitudinal guide members do not longitudinally overlap the longitudinal contracting member.

For some applications, wherein, when the first and the second flexible longitudinal guide members are removably coupled to the sleeve, no portion of either the first flexible longitudinal guide member or the second flexible longitudinal guide member is disposed more than 1.5 cm from the first and the second sleeve ends, respectively, measured when the sleeve is fully longitudinally extended.

For some applications, wherein, when the first and the second flexible longitudinal guide members are removably coupled to the sleeve, the first and the second flexible longitudinal guide members are collectively disposed along less than 30% of a length of the sleeve, measured when the sleeve is fully longitudinally extended.

There is still further provided, in accordance with an application of the present invention, apparatus including an annuloplasty system, which includes:

an implantable structure, which includes a flexible sleeve, having first and second sleeve ends; and first and second flexible longitudinal guide members, which (a) are removably coupled to the sleeve within 1.5 cm of the first and the second sleeve ends, respectively, measured when the sleeve is fully longitudinally extended, and (b) extend from the first and the second sleeve ends, respectively, away from the sleeve.

For some applications, the implantable structure includes a longitudinal contracting member, which is configured to longitudinally contract a longitudinal portion of the sleeve, and the first and the second flexible longitudinal guide members are separate and distinct from the longitudinal contracting member.

For some applications, wherein, when the first and the second flexible longitudinal guide members are removably coupled to the sleeve, the first and the second flexible longitudinal guide members do not longitudinally overlap the longitudinal contracting member.

For some applications, wherein, when the first and the second flexible longitudinal guide members are removably coupled to the sleeve, no portion of either the first flexible longitudinal guide member or the second flexible longitudinal guide member is disposed more than 1.5 cm from the first and the second sleeve ends, respectively, measured when the sleeve is fully longitudinally extended.

For some applications, wherein, when the first and the second flexible longitudinal guide members are removably coupled to the sleeve, the first and the second flexible longitudinal guide members are collectively disposed along less than 30% of a length of the sleeve, measured when the sleeve is fully longitudinally extended.

The present invention will be more fully understood from the following detailed description of applications thereof, taken together with the drawings, in which:

BRIEF DESCRIPTION OF THE DRAWINGS

FIGS. 2A-I are schematic illustrations of a procedure for implanting the implantable structure of FIG. 1 to repair a mitral valve, in accordance with an application of the present invention;

FIGS. 8A-D are schematic illustrations of coupling elements, in accordance with respective applications of the present invention;

FIG. 9 is a schematic illustration of another configuration of the implantable structure of FIG. 1, prior to implantation, further comprising an elongated radial-force application element, in accordance with an application of the present invention;

FIG. 15 is a schematic illustration of another configuration of the implantable structure of FIGS. 9 and 10, in accordance with an application of the present invention;

FIGS. 16A-B are schematic illustrations of another configuration of the implantable structure of FIGS. 9 and 10, in which the sleeve is shaped so as to define an integrally closed loop having no sleeve ends, in accordance with an application of the present invention;

FIG. 17 is a schematic illustration of another configuration of the implantable structure of FIG. 9 implanted around the mitral valve, in accordance with an application of the present invention FIGS. 18A and 18B are schematic illustrations of yet another configuration of the implantable structure of FIG. 1, prior to implantation and upon implantation around the mitral valve, respectively, in accordance with an application of the present invention;

DETAILED DESCRIPTION OF EMBODIMENTS

Figure 1:
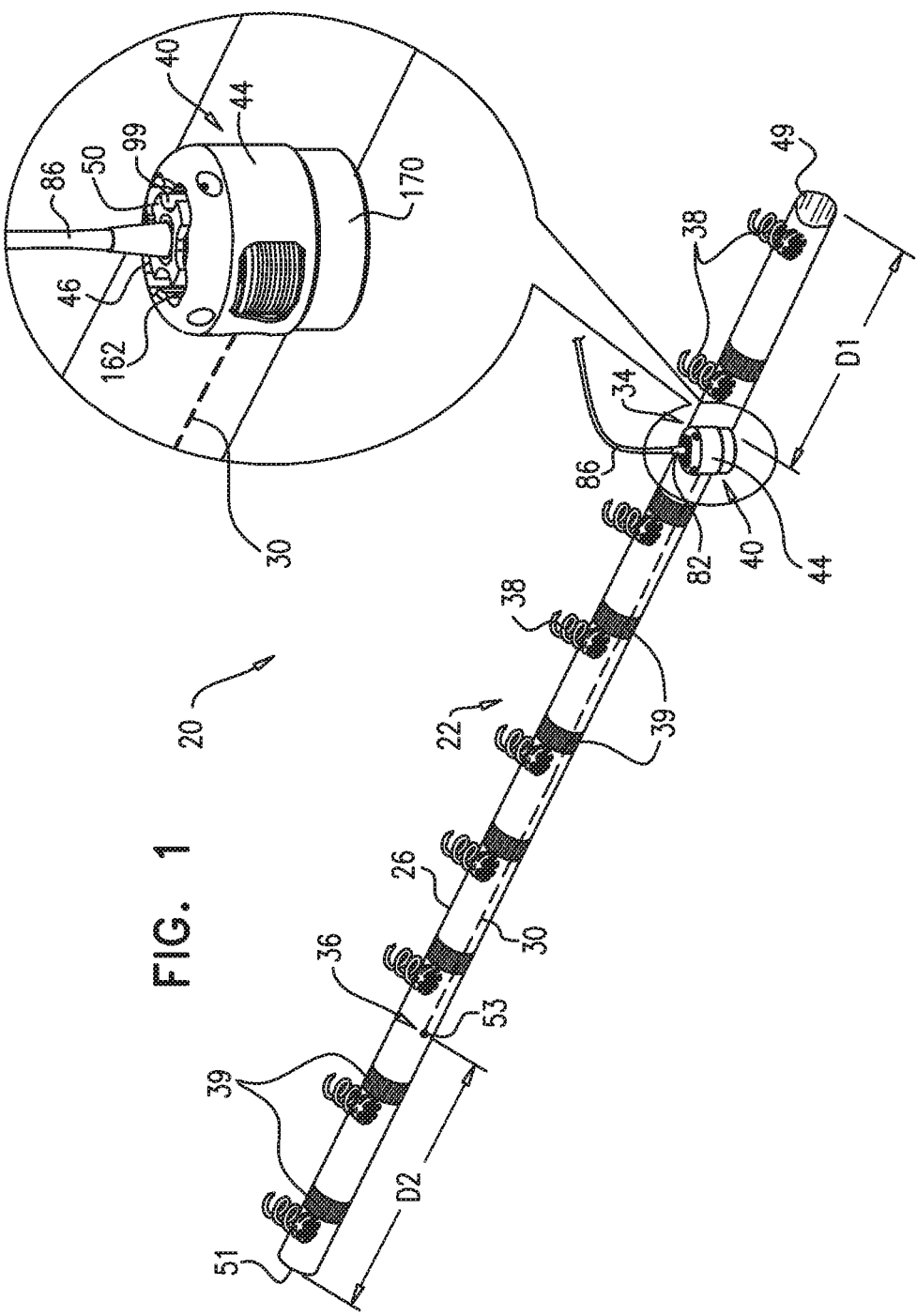
FIG. 1 is a schematic illustration of a system for repairing a dilated atrioventricular valve, such as a mitral valve, in accordance with an application of the present invention.

FIG. 1 is a schematic illustration of a system 20 for repairing a dilated atrioventricular valve, such as a mitral valve or a tricuspid valve, in accordance with an application of the present invention. System 20 comprises an adjustable implantable structure 22, shown in FIG. 1 in a straight, relaxed, non-contracted state, and an anchor deployment manipulator 24 (shown in FIGS. 2G-H). For some applications, implantable structure 22 is configured to be deployed as an annuloplasty ring, while for other applications, implantable structure 22 is configured to be deployed as a base ring to which a prosthetic valve is coupled, such as described hereinbelow with reference to FIG. 25A-B or 26. Implantable structure 22 comprises a flexible sleeve 26. Anchor deployment manipulator 24 is advanced into sleeve 26, as shown in FIGS. 2G-H, and, from within the sleeve, deploys tissue anchors through a wall of the sleeve into cardiac tissue, thereby anchoring the ring around at least a portion of the valve annulus. For some applications, anchor deployment manipulator is implemented using techniques described in US Patent Application Publication 2010/0280604, which is incorporated herein by reference, with reference to FIGS. 2, 3, 4, 5A, 5B, 6A, 6B, 7, 8, 13, and/or 20A-E thereof.

For some applications, implantable structure 22 comprises a partial annuloplasty ring. In these applications, sleeve 26 is configured to be placed only partially around the valve annulus (i.e., to assume a C-shape), and, once anchored in place, to be contracted so as to circumferentially tighten the valve annulus. For other applications, sleeve 26 is configured to be implanted entirely around the valve annulus in a closed loop, such as described hereinbelow with reference to FIG. 4, 5, 7A-B, 10, 16A-B, 17 or 18B.

Implantable structure 22 further comprises a contracting assembly 40, which facilitates contracting of the implantable structure. Contracting assembly 40 typically comprises a contracting mechanism 28, and a longitudinal contracting member 30, which is coupled to contracting mechanism 28, extends along a portion of the sleeve, and is typically flexible. For example, contracting member 30 may comprise at least one wire. Contracting assembly 40 is configured to contract a longitudinal portion of sleeve 26, and is described in more detail hereinbelow. In addition, the implantable structure typically comprises a plurality of tissue anchors 38, typically between about 5 and about 20 anchors, such as about 10 or about 16 anchors. In FIG. 1, anchors 38 are shown coupled to implantable structure 22, deployed through the wall of sleeve 26. For some applications, anchors 38 are configured as described with reference to FIGS. 5A-C, 5D, 5E, 5F, 5G, 5H, and/or 5I in US Patent Application Publication 2012/0330411, which is incorporated herein by reference, while for other applications, anchors 38 comprise tissue anchors known in the art.

Flexible sleeve 26 may comprise a braided, knitted, or woven mesh or a tubular structure comprising ePTFE. For some applications, the braid comprises metal and fabric fibers. The metal fibers, which may comprise Nitinol for example, may help define the shape of the sleeve, e.g., hold the sleeve open to provide space for passage and manipulation of deployment manipulator 24 within the sleeve. The fabric fibers may promote tissue growth into the braid. Typically, sleeve 26 is substantially longitudinally non-extensible, i.e., a length thereof is substantially constant, i.e., cannot be longitudinally stretched, under normal usage conditions. Alternatively, the sleeve is somewhat elastic, which gives the sleeve a tendency to longitudinally contract, thereby helping tighten the sleeve. For example, the sleeve may be bellows- or accordion-shaped.

For some applications, the sleeve is configured to have a tendency to assume a straight shape when in its relaxed, non-contracted state. This straightness may help the surgeon locate the next site for each subsequent anchor during the implantation procedure. For example, because the sleeve assumes a generally straight shape, the sleeve may help provide an indication of distance between adjacent anchoring sites. For some applications, the sleeve is configured to have a controllably variable stiffness. For example, a somewhat stiff wire may be placed in the sleeve to provide the stiffness, and subsequently be removed at the conclusion of the implantation procedure when the stiffness is no longer useful.

For some applications, sleeve 26 comprises a plurality of radiopaque markers 39, which are positioned along the sleeve at respective longitudinal sites. The markers may provide an indication in a radiographic image (such as a fluoroscopy image) of how much of the sleeve has been deployed at any given point during an implantation procedure, in order to enable setting a desired distance between anchors 38 along the sleeve. For some applications, the markers comprise a radiopaque ink.

Typically, at least a portion (e.g., at least three, such as all) of the longitudinal sites are longitudinally spaced at a constant interval. Typically, the longitudinal distance between the distal edges of adjacent markers, and/or the distance between the proximal edges of adjacent markers, is set equal to the desired distance between adjacent anchors. For example, the markers may comprise first, second, and third markers, which first and second markers are adjacent, and which second and third markers are adjacent, and the distance between the proximal and/or distal edges of the first and second markers equal the corresponding distance between the proximal and/or distal edges of the second and third markers. For example, the distance may be between 3 and 15 mm, such as 6 mm, and the longitudinal length of each marker may be between 0.1 and 14 mm, such as 2 mm.

(If, for example, the distance were 6 mm and the length were 2 mm, the longitudinal gaps between adjacent markers would have lengths of 4 mm.)

Longitudinal contracting member 30 comprises a wire, a ribbon, a rope, or a band, which typically comprises a flexible and/or superelastic material, e.g., nitinol, polyester, HDPE, stainless steel, or cobalt chrome. For some applications, the wire comprises a radiopaque material. For some applications, longitudinal contracting member 30 comprises a braided polyester suture (e.g., Ticron). For some applications, longitudinal contracting member 30 is coated with polytetrafluoroethylene (PTFE). For some applications, contracting member 30 comprises a plurality of wires that are intertwined to form a rope structure. For some applications, implantable structure 22 comprises a plurality of contracting members 30, which may extend along generally the same longitudinal portion of sleeve 26, or along respective, different portions of sleeve 26 (e.g., as described with reference to FIG. 13 in above-mentioned US Patent Application Publication 2012/0330411).

For some applications, contracting member 30 is positioned at least partially within a lumen of the sleeve 26, such as entirely within the lumen (as shown in FIGS. 1, 2H-I, 3, 4, 6, and 7A-B). For some applications in which the contracting member is positioned partially within the lumen, the contracting member is sewn into the wall of the sleeve, such that the contracting member is alternatingly inside and outside of the sleeve along the length of the sleeve (configuration not shown). Optionally, sleeve 26 defines an internal channel within which member 30 is positioned (configuration not shown). Alternatively, the contracting member is disposed outside the lumen of the sleeve, such as alongside an outer wall of the sleeve. For example, sleeve 26 may define an external channel within which contracting member 30 is positioned, or the sleeve may comprise or be shaped so as to define external coupling elements, such as loops or rings (configuration not shown). For some applications, contracting member 30 is positioned approximately opposite the anchors.

For some applications of the present invention, contracting mechanism 28 comprises a rotatable structure, such as a spool 46. The rotatable structure is arranged such that rotation thereof applies a longitudinal contracting force, thereby contracting at least a longitudinal portion of implantable structure 22. Typically, in these applications, contracting mechanism 28 further comprises a housing 44 in which the rotatable structure, e.g., the spool, is positioned. Contracting member 30 has first and second member ends, and a first member end portion, which extends from the first member end toward the second member end along only a longitudinal portion of the contracting member. For some applications, the first member end portion, e.g., the first member end of contracting member 30, is coupled to contracting mechanism 28, such as the rotatable structure, e.g., the spool (alternatively, although the first member end portion is coupled to the contracting mechanism, the first member end protrudes beyond the contracting mechanism). For example, spool 46 may be shaped to provide a hole 42 or other coupling mechanism for coupling the first end of contracting member 30 to the spool, and thereby to contracting mechanism 28. Contracting assembly 40 is arranged such that rotation of the spool winds a portion of the contracting member around the spool. Alternatively, contracting member 30 may comprise at least one wire (e.g., exactly one wire) that passes through a coupling mechanism of spool 46, in order to couple the wire to the spool. The ends of the wire are brought together, and together serve as a second end 53 of contracting member 30. In this configuration, approximately the longitudinal center of the wire serves as the first end of the contracting member.

Alternatively, contracting mechanism 28 may comprise a ratchet contracting mechanism, which typically comprises a ratchet-coupling housing. Contracting member 30 is shaped so as to define engaging structures, such as grooves or teeth. Techniques may be used that are described in International Application PCT/IL2009/000593, filed Jun. 15, 2009, which published as PCT Publication WO 10/004546, and in U.S. application Ser. No. 12/996,954, which published as US Patent Application Publication 2011/0166649, in the national stage thereof, all of which applications and publications are incorporated herein by reference.

Further alternatively, contracting mechanism 28 may comprise a housing or other structure (e.g., a ring or an eyelet) which is shaped so as to define an opening therethrough. Contracting member 30 is drawn through the opening (such that the first member end protrudes beyond the opening), and, once a desired length has been achieved, is locked, such as using a locking bead, or by crimping or knotting.

Contracting member 30 extends along less than the entire length of sleeve 26. Contracting mechanism 28 (e.g., housing 44 thereof) is disposed at a first site 34 of sleeve 26 that is a first longitudinal distance D1 from a first end of the sleeve, either a proximal end 49 of sleeve 26, as shown in FIG. 1, or a distal end 51 of sleeve 26, as shown in FIGS. 2G-I. (Longitudinal distance D1 is measured between the first end of the sleeve and the portion of contracting mechanism 28 that is closest to the first end.) For some applications, second end 53 of contracting member 30 is coupled to the sleeve at a second site 36 that is a second longitudinal distance D2 from a second end of the sleeve, which second end is longitudinally opposite the first end of the sleeve. For applications in which contracting mechanism 28 comprises a rotatable structure, rotation of the rotatable structure, such as spool 46, longitudinally contracts at least a portion of the sleeve, such as by winding a portion of the contracting member around the spool, thereby pulling the far end of the implantable structure toward the spool and shortening and tightening the implantable structure. Such rotation of the rotatable structure, or other actuation of contracting assembly 40, typically applies a longitudinal contracting force only between first and second sites 34 and 36, which longitudinally contracts at least a portion, e.g. all, of the sleeve only between first and second sites 34 and 36. (For example, the longitudinal force may longitudinally contract less than the entire sleeve between first and second sites 34 and 36 in applications in which system 20 comprises coiled element 240, which provides a contraction-restricting portion of the sleeve, as described hereinbelow with reference to FIGS. 10A-E and/or 11A-E in above-mentioned US Patent Application Publication 2012/0330411.) Therefore, the portions of the sleeve beyond first and second sites 34 and 36 (towards the ends of the sleeve) are not contracted by contracting assembly 40.

Typically, contracting member 30 extends along (i.e., a distance along the sleeve between first and second sites 34 and 36 equals) no more than 80% of the length of the sleeve, e.g., no more than 60% or no more than 50% of the length. Typically, contracting member 30 extends along no more than 80% of a circumference of the loop when the sleeve is placed around the annulus (i.e., the total length of the loop less the length of any overlapping portion). Typically, contracting member 30 extends along (i.e., a distance along the sleeve between first and second sites 34 and 36 equals) at least 20% of the length of the sleeve, e.g., at least than 40% or at least than 50% of the length. Typically, contracting member 30 extends along at least 20% of the circumference of the loop when the sleeve is placed around the annulus, e.g., at least 30% or at least 50%.

For some applications, first longitudinal distance D1, measured when sleeve 26 is in a straight, relaxed, non-contracted state, is at least 3 mm, e.g., at least 5 mm, such as at least 9 mm, e.g., at least 14 mm; no greater than 20 mm, such as no greater than 15 mm; and/or between 5 and 20 mm, such as between 9 and 15 mm. Alternatively or additionally, for some applications, second longitudinal distance D2, measured when sleeve 26 is in a straight, relaxed, non-contracted state, is at least 3 mm, e.g., at least 5 mm, such as at least 9 mm, e.g., at least 14 mm; no greater than 20 mm, such as no greater than 15 mm; and/or between 5 and 20 mm, such as between 9 and 15 mm. Further alternatively or additionally, first longitudinal distance D1, measured when sleeve 26 is in a straight, relaxed, non-contracted state, is no greater than 20%, such as no greater than 10% of a total length of the sleeve, measured when sleeve 26 is in a straight, relaxed, non-contracted state. Further alternatively or additionally, second longitudinal distance D2, measured when sleeve 26 is in a straight, relaxed, non-contracted state, is no greater than 30%, such as no greater than 20%, e.g., no greater than 10% of the total length of the sleeve measured, when sleeve 26 is in a straight, relaxed, non-contracted state. For some applications, the total length of the sleeve, measured when the sleeve is in a straight, relaxed, non-contracted state is at least 5 cm, no more than 25 cm, and/or between 5 and 25 cm. For some applications in which the sleeve is implanted in a closed loop, the total length of the sleeve is selected to be between 1.3 and 1.4 times a circumference of the annulus, in order to provide overlapping portion 114, described hereinbelow with reference to FIGS. 3 and 4.

For some applications, at least one of tissue anchors 38 (e.g., exactly one, at least two, exactly two, at least three, exactly three, or at least four, or no more than four) is coupled to sleeve 26 longitudinally between contracting mechanism 28 (e.g., housing 44 thereof) and the first sleeve end (i.e., the end of the sleeve to which contracting mechanism 28 is closest), exclusive, and at least 3, such as at least 6, of tissue anchors 38 are coupled to the sleeve alongside contracting member 30, longitudinally between first site 34 and second site 36 (second member end 53), exclusive. (As used in the present application, including in the claims, "exclusive," when used with respect to a range of locations, means excluding the endpoints of the range.)

Alternatively or additionally, for some applications, at least one of tissue anchors 38 (e.g., exactly one, at least two, exactly two, at least three, exactly three, or at least four, or no more than four) is coupled to sleeve 26 longitudinally between second site 36 (second member end 53) and the second sleeve end (i.e., the end of the sleeve to which second member end 53 is closest), exclusive, and at least 3, such as at least 6, of tissue anchors 38 are coupled to the sleeve alongside contracting member 30, longitudinally between first site 34 and second site 36 (second member end 53), exclusive.

In the exemplary configuration shown in FIG. 1, exactly two tissue anchors 38 are coupled to the sleeve longitudinally between the contracting mechanism (e.g., the housing) (first site 34) and the first sleeve end, exclusive, exactly two tissue anchors are coupled to the sleeve longitudinally between first site 34 and second site 36 (second member end 53), exclusive, and exactly six tissue anchors 38 are coupled to the sleeve alongside the contracting member, longitudinally between first site 34 and second site 36 (second member end 53), exclusive.

Providing the one or more anchors beyond first and second sites 34 and 36 (i.e., beyond the contracting portion of contracting member 30) generally distributes force applied by contraction of contracting assembly 40 over these anchors. In contrast, in some configurations of implantable structure 22 in which anchors are not provided beyond first and second sites 34 and 36, the force applied by the contracting assembly is applied predominantly to the single anchor nearest the first end of the contracting member, and the single anchor nearest to second end of the contracting member.

For some applications, anchors 38 are positioned along sleeve 26 with a longitudinal distance of between 4.5 and 9 mm, such as 6 mm, between each pair of longitudinally-adjacent anchors.

It is noted that the anchors may be positioned as described above by a surgeon during an implantation procedure, such as described hereinbelow with reference to FIGS. 2A-I, or the anchors may be prepositioned in the sleeve.

Reference is now made to FIGS. 2A-I, which are schematic illustrations of a procedure for implanting implantable structure 22 to repair a mitral valve 130, in accordance with an application of the present invention. The procedure is typically performed with the aid of imaging, such as fluoroscopy, transesophageal echo, and/or echocardiography.

Figure 2A:
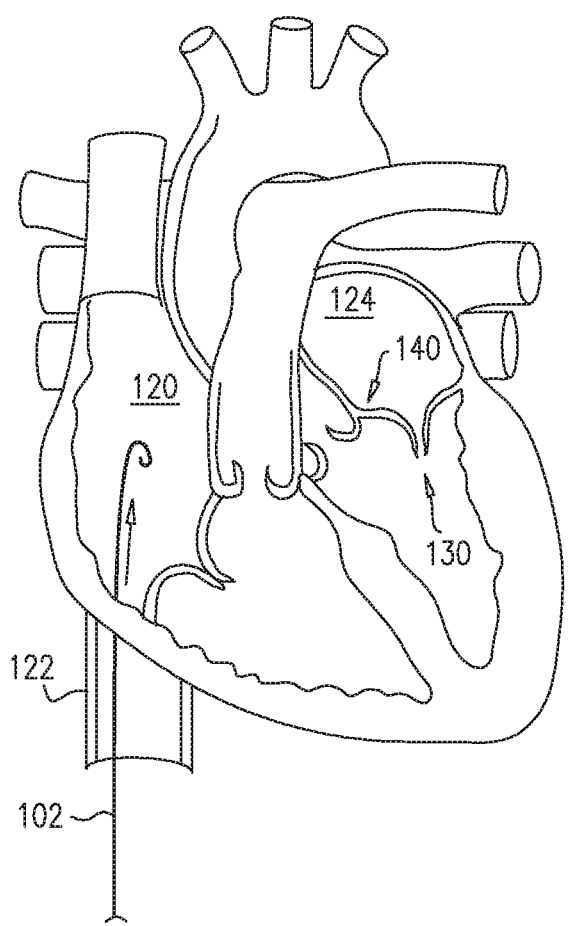

The procedure typically begins by advancing a semi-rigid guidewire 102 into a right atrium 120 of the patient, as shown in FIG. 2A.

Figure 2B:
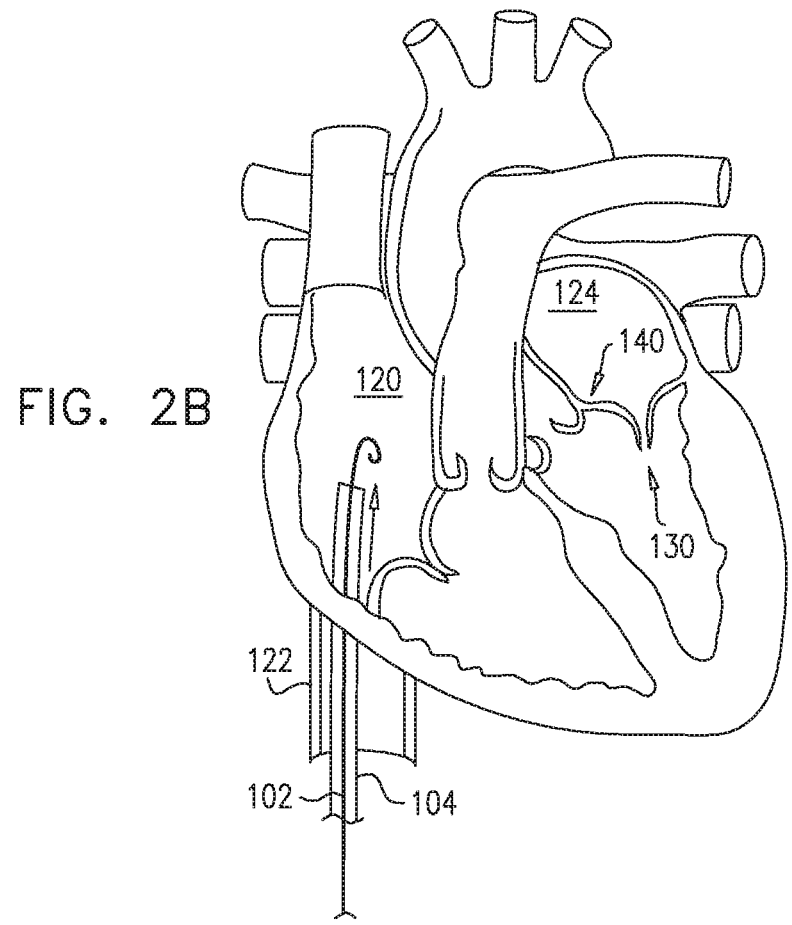
Figure 2C:
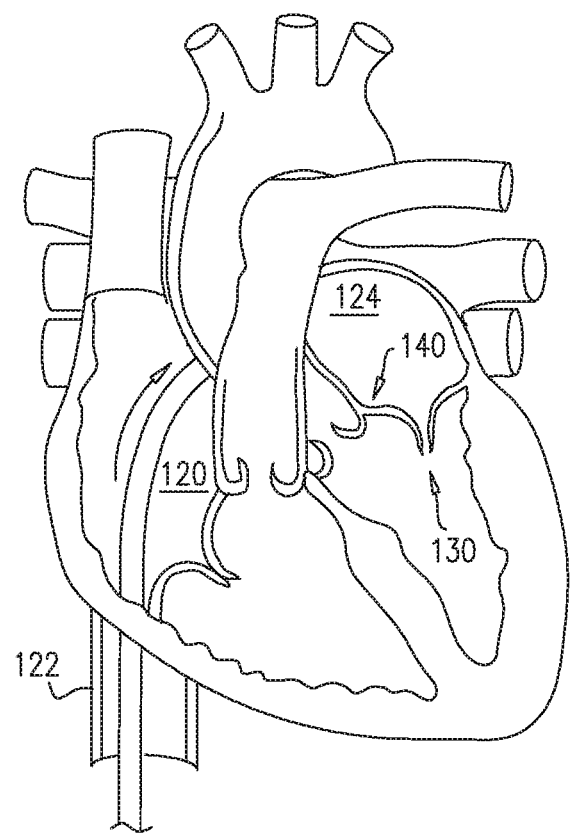

As shown in FIG. 2B, guidewire 102 provides a guide for the subsequent advancement of a sheath 104 therealong and into the right atrium. Once sheath 104 has entered the right atrium, guidewire 102 is retracted from the patient's body. Sheath 104 typically comprises a 14-20 F sheath, although the size may be selected as appropriate for a given patient. Sheath 104 is advanced through vasculature into the right atrium using a suitable point of origin typically determined for a given patient. For example:

sheath 104 may be introduced into the femoral vein of the patient, through an inferior vena cava 122, into right atrium 120, and into a left atrium 124 transseptally, typically through the fossa ovalis;

sheath 104 may be introduced into the basilic vein, through the subclavian vein to the superior vena cava, into right atrium 120, and into left atrium 124 transseptally, typically through the fossa ovalis; or sheath 104 may be introduced into the external jugular vein, through the subclavian vein to the superior vena cava, into right atrium 120, and into left atrium 124 transseptally, typically through the fossa ovalis.

For some applications, sheath 104 is advanced through an inferior vena cava 122 of the patient (as shown) and into right atrium 120 using a suitable point of origin typically determined for a given patient.

Sheath 104 is advanced distally until the sheath reaches the interatrial septum.

Figure 2D:
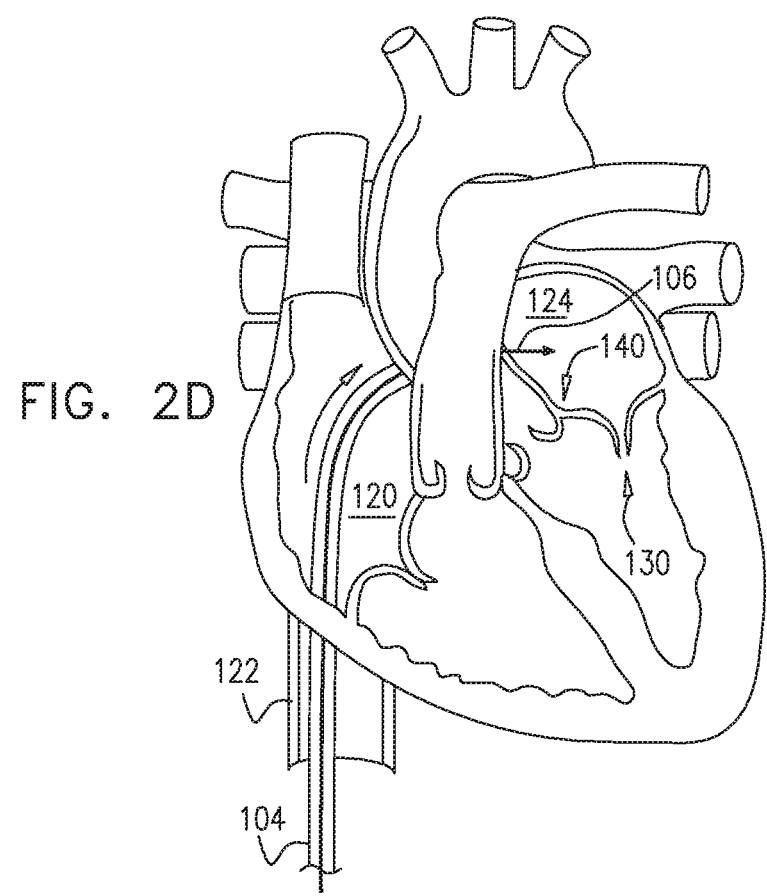

As shown in FIG. 2D, a resilient needle 106 and a dilator (not shown) are advanced through sheath 104 and into the heart. In order to advance sheath 104 transseptally into left atrium 124, the dilator is advanced to the septum, and needle 106 is pushed from within the dilator and is allowed to puncture the septum to create an opening that facilitates passage of the dilator and subsequently sheath 104 therethrough and into left atrium 124. The dilator is passed through the hole in the septum created by the needle.

Typically, the dilator is shaped to define a hollow shaft for passage along needle 106, and the hollow shaft is shaped to define a tapered distal end. This tapered distal end is first advanced through the hole created by needle 106. The hole is enlarged when the gradually increasing diameter of the distal end of the dilator is pushed through the hole in the septum.

Figure 2E:
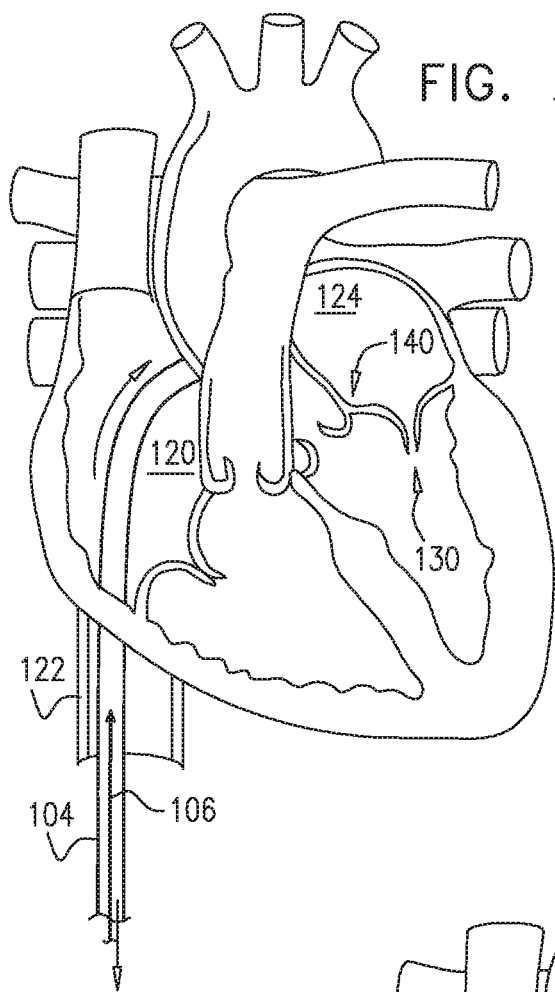

The advancement of sheath 104 through the septum and into the left atrium is followed by the extraction of the dilator and needle 106 from within sheath 104, as shown in FIG. 2E.

Figure 2F:
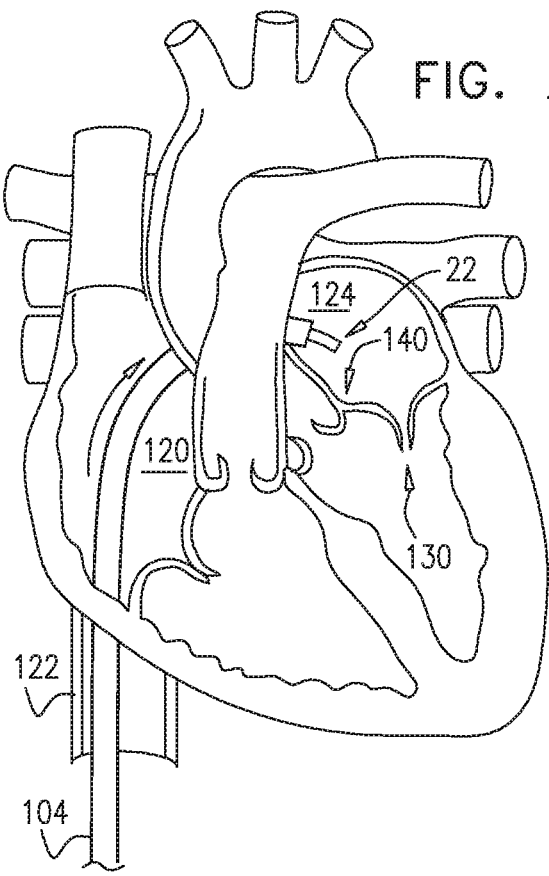
Figure 2G:
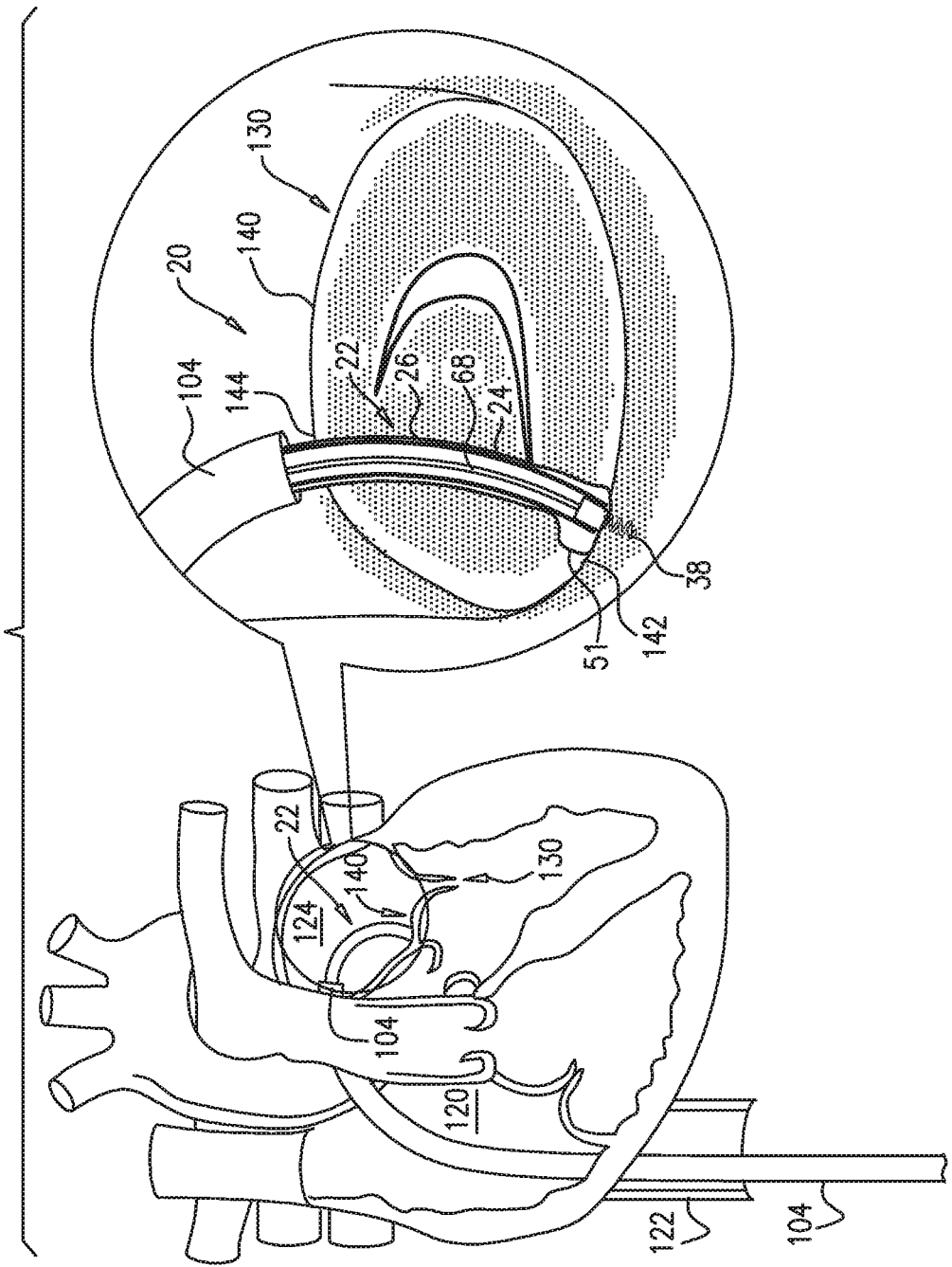
Figure 2H:
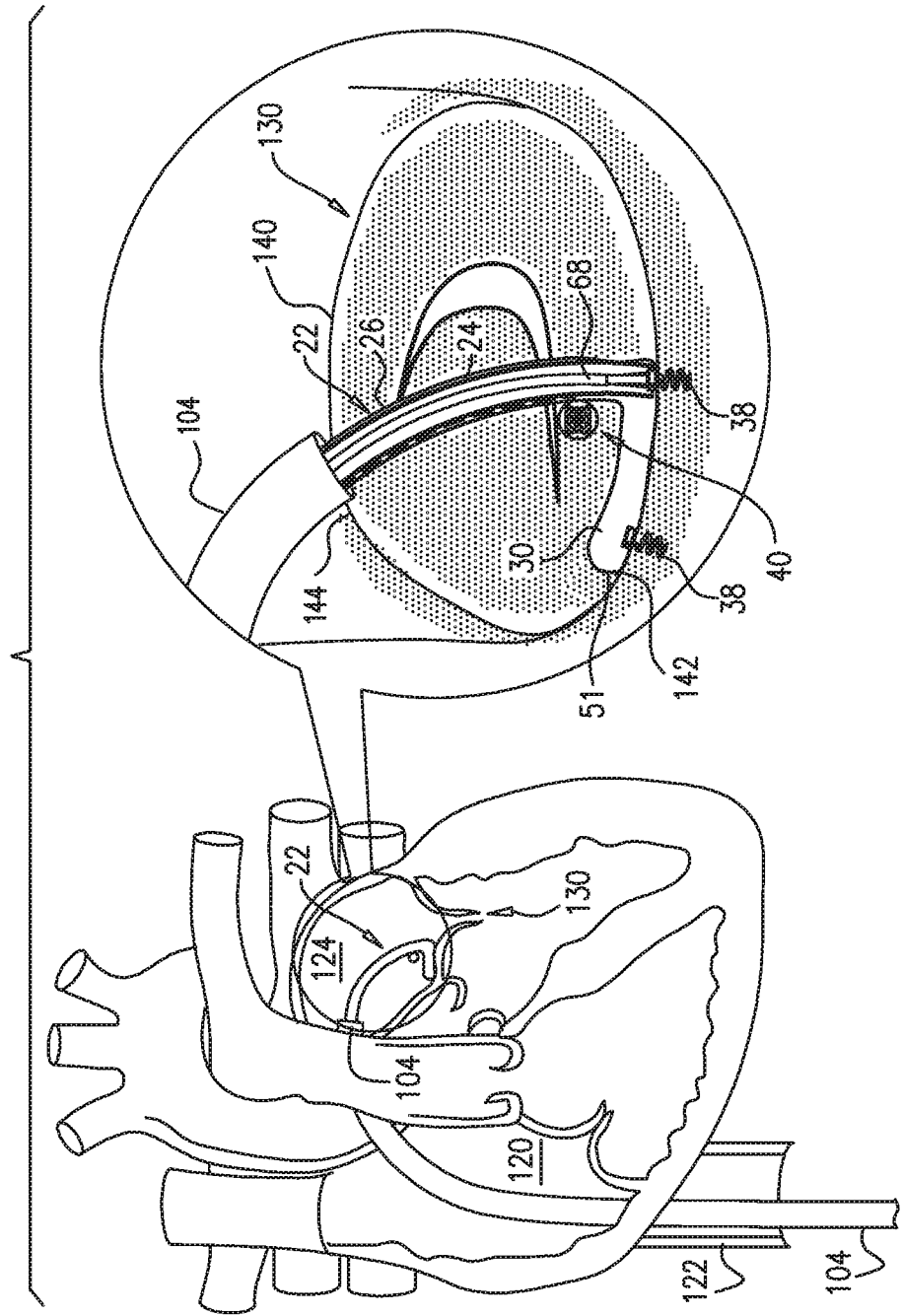

As shown in FIG. 2F, implantable structure 22 (with anchor deployment manipulator 24 therein) is advanced through sheath 104 into left atrium 124.

As shown in FIG. 2G, distal end 51 of sleeve 26 is positioned in a vicinity of a left fibrous trigone 142 of an annulus 140 of mitral valve 130. (It is noted that for clarity of illustration, distal end 51 of sleeve 26 is shown schematically in the cross-sectional view of the heart, although left fibrous trigone 142 is in reality not located in the shown cross-sectional plane, but rather out of the page closer to the viewer.) Alternatively, the distal end is positioned in a vicinity of a right fibrous trigone 144 of the mitral valve (configuration not shown). Further alternatively, the distal end of the sleeve is not positioned in the vicinity of either of the trigones, but is instead positioned elsewhere in a vicinity of the mitral valve, such as in a vicinity of the anterior or posterior commissure. Still further alternatively, for some applications, the distal end is positioned along an anterior portion of the annulus, such as described hereinbelow with reference to FIG. 4. For some applications, outer tube 66 of anchor deployment manipulator 24 is steerable, as is known in the catheter art, while for other applications, a separate steerable tube is provided, such as described in the above-mentioned '604 publication, with reference to FIG. 15 and FIG. 16 thereof. In either case, the steering functionality typically allows the area near the distal end of the deployment manipulator to be positioned with six degrees of freedom. Once positioned at the desired site near the selected trigone, deployment manipulator 24 deploys a first anchor 38 through the wall of sleeve 26 into cardiac tissue near the trigone.

As shown in FIG. 2H, deployment manipulator 24 is repositioned along annulus 140 to another site selected for deployment of a second anchor 38. Typically, the first anchor is deployed most distally in the sleeve (generally at or within a few millimeters of the distal end of the sleeve), and each subsequent anchor is deployed more proximally, such that the sleeve is gradually pulled off (i.e., withdrawn from) the deployment manipulator in a distal direction during the anchoring procedure. The already-deployed first anchor 38 holds the anchored end of sleeve 26 in place, so that the sleeve is drawn from the site of the first anchor towards the site of the second anchor. Typically, as the sleeve is pulled off (i.e., withdrawn from) the deployment manipulator, the deployment manipulator is moved generally laterally along the cardiac tissue, as shown in FIG. 2H. Deployment manipulator 24 deploys the second anchor through the wall of the sleeve into cardiac tissue at the second site. Depending on the tension applied between the first and second anchor sites, the portion of sleeve 26 therebetween may remain tubular in shape, or may become flattened, which may help reduce any interference of the implantable structure with blood flow.

For some applications, in order to provide the second and subsequent anchors, anchor driver 68 is withdrawn from the subject's body via sheath 104 (typically while leaving outer tube 66 of the deployment manipulator in place in the sleeve), provided with an additional anchor, and then reintroduced into the subject's body and into the outer tube. Alternatively, the entire deployment manipulator, including the anchor driver, is removed from the body and subsequently reintroduced upon being provided with another anchor. Further alternatively, deployment manipulator 24 is configured to simultaneously hold a plurality of anchors, and to deploy them one at a time at the selected sites.

As shown in FIG. 2I, the deployment manipulator is repositioned along the annulus to additional sites, at which respective anchors are deployed, until the last anchor is deployed in a vicinity of right fibrous trigone 144 (or left fibrous trigone 142 if the anchoring began at the right trigone), thereby fastening sleeve 26 and implantable structure 22 to the annulus. Alternatively, the last anchor is not deployed in the vicinity of a trigone, but is instead deployed elsewhere in a vicinity of the mitral valve, such as in a vicinity of the anterior or posterior commissure.

For applications in which contracting mechanism 28 comprises spool 46, a rotation tool is typically used to rotate spool 46 of contracting mechanism 28, in order to tighten implantable structure 22. For some applications, the rotation tool is used that is described and shown in the above-mentioned '604 publication, with reference to FIGS. 6A-B, 7, and 8 thereof. As described therein, contracting mechanism 28 comprises longitudinal member 86 that is attached to the contracting mechanism and passes out of the body of the subject, typically via sheath 104. In order to readily bring the rotation tool to a driving interface of contracting mechanism 28, the rotation tool is guided over longitudinal member 86. For some applications, spool 46 is configured as described in the '604 publication with reference to FIGS. 1-4, 6A-B, 7, and/or 8 thereof.

Contracting assembly 40 typically comprises a locking mechanism that locks contracting member 30 with respect to contracting assembly 40, thereby preventing loosening (and typically tightening) of contracting member 30. For some applications, spool 46 comprises the locking mechanism that prevents rotation of the spool after contracting member 30 has been tightened. For example, locking techniques may be used that are described and shown in US Application Publication 2010/0161047, which is incorporated herein by reference, with reference to FIG. 4 thereof, and/or with reference to FIGS. 6B, 7, and 8 of the above-mentioned '604 publication. Alternatively, for some applications, contracting mechanism 28 is configured to tighten contracting member 30, crimp the contracting member to hold the contracting member taut, and subsequently cut the excess length of the contracting member.

For some applications, a rotation handle is used to tighten the implantable structure, such as described and shown in the above-mentioned '604 publication, with reference to FIGS. 9A-C and 10A-D thereof. As mentioned above, deploying the one or more anchors beyond the contracting portion of contracting member 30 generally distributes force applied by contraction of contracting assembly 40 over these anchors.

For some applications, sleeve 26 is filled with a material (e.g., polyester, polytetrafluoroethylene (PTFE), polyethylene terephthalate (PET), or expanded polytetrafluoroethylene (ePTFE)) after being implanted. The material is packed within at least a portion, e.g., 50%, 75%, or 100%, of the lumen of sleeve 26. The filler material functions to prevent (1) formation within the lumen of sleeve 26 of clots or (2) introduction of foreign material into the lumen which could obstruct the sliding movement of contracting member 30.

For some applications, proximal end 49 of sleeve 26 is closed upon completion of the implantation procedure. Alternatively, the proximal end of the sleeve may have a natural tendency to close when not held open by deployment manipulator 24.

For some applications, following initial contraction of implantable structure 22 during the implantation procedure, the structure may be further contracted or relaxed at a later time after the initial implantation, such as between several weeks and several months after the initial implantation. Using real-time monitoring and tactile feedback, optionally in combination with fluoroscopic imaging, a rotation tool or anchor driver of a deployment manipulator may be reintroduced into the heart and used to contract or relax implantable structure 22.

Figure 3:
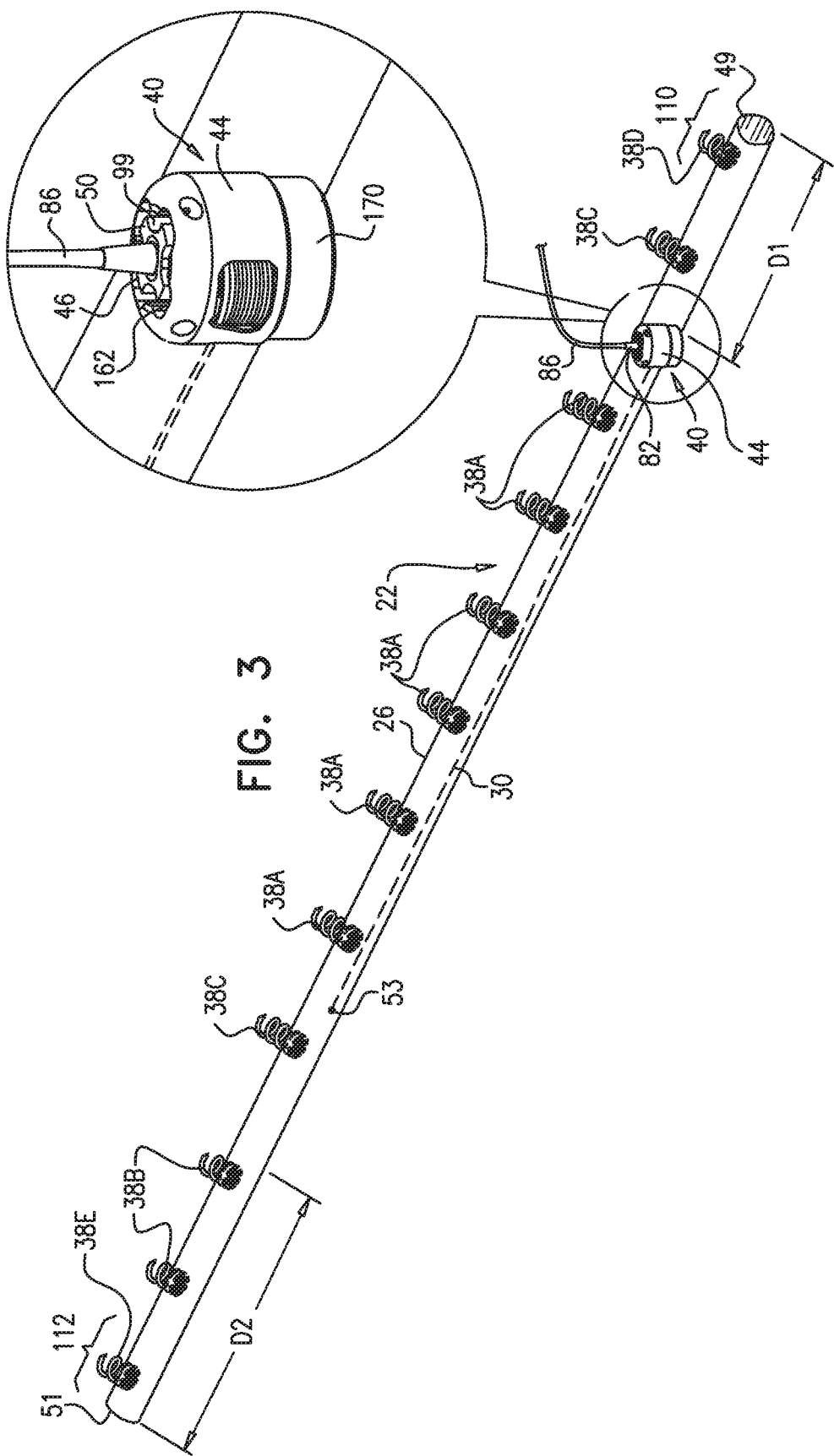
FIG. 3 is a schematic illustration of another configuration of the implantable structure of FIG. 1, prior to implantation, in accordance with an application of the present invention.
Figure 4:
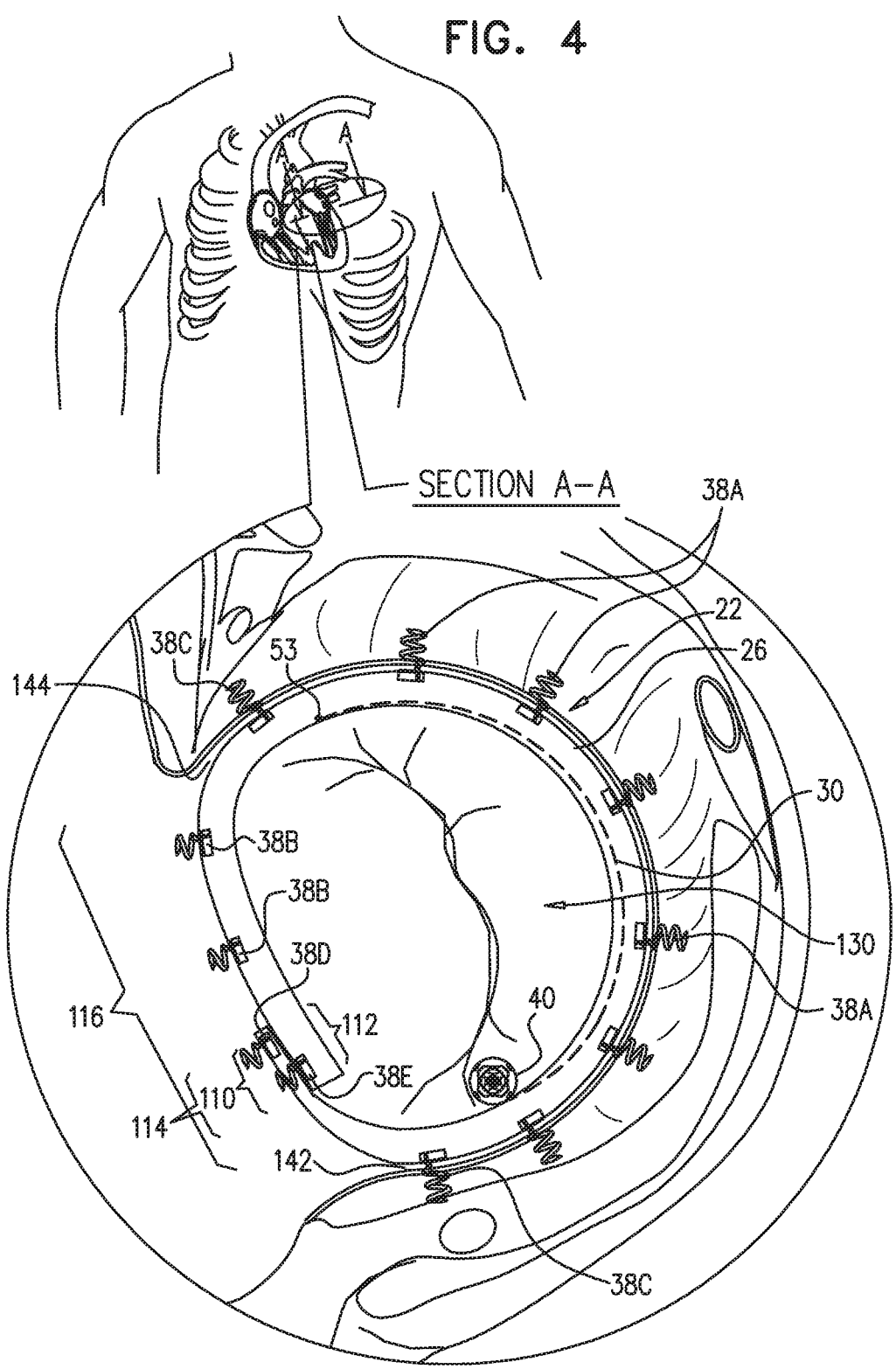
FIG. 4 is a schematic illustration of the implantable structure of FIG. 3 after implantation around the annulus of a mitral valve, in accordance with an application of the present invention.

Reference is now made to FIGS. 3 and 4, which are schematic illustrations of another configuration of implantable structure 22, in accordance with an application of the present invention. FIG. 3 shows implantable structure 22 in a straight, relaxed, non-contracted state, prior to implantation. FIG. 4 shows the implantable structure after implantation around the annulus of mitral valve 130, in accordance with an application of the present invention.

In this configuration, sleeve 26 is implanted in a closed loop. More particularly, a first portion 110 of sleeve 26 longitudinally extends from the first sleeve end (i.e., the end of the sleeve to which contracting mechanism 28, e.g., housing 44 thereof, is closest) toward contracting mechanism 28, e.g., housing 44 thereof (but typically does not extend all of the way to the contracting mechanism), and a second portion 112 of the sleeve longitudinally extends from the second sleeve end (i.e., the end of the sleeve to which second member end 53 is closest) toward second member end 53 (but typically does not extend all of the way to the second member end). As shown in FIG. 4, once implanted, sleeve 26 is arranged in a closed loop, such that first and second portions 110 and 112 of the sleeve together define a longitudinally overlapping portion 114 of the sleeve. The overlapping portion typically has a length of at least 2 mm (e.g., at least 5 mm), no more than 60 mm (e.g., no more than 50 mm), and/or between 2 mm (e.g., 5 mm) and 60 mm (e.g., 50 mm), and/or a length that is at least 1% of a total length of the sleeve, no more than 40% of the total length (e.g., no more than 30%), and/or between 1% and 40% (e.g., 30%) of the total length of the sleeve, measured when the sleeve is in a straight, relaxed, non-contracted state.

For some applications, at least one of tissue anchors 38 (labeled as 38E in FIGS. 3 and 4) penetrates both first and second portions 110 and 112 of the sleeve at overlapping portion 114. Such a mutual anchor helps ensure that the first and second portions remain tightly coupled together and to the tissue, so that the sleeve retains its closed loop shape. For some applications in which tissue anchor 38E comprises a coupling head and a tissue coupling element, such as described hereinbelow with reference to FIG. 5D, 5E, 5F, 5G, or 51 in above-mentioned US Patent Application Publication 2012/0330411, the tissue coupling element penetrates both first and second portions 110 and 112 of the sleeve at overlapping portion 114, and the coupling head is positioned within one of first and second portions 110 and 112 of the sleeve at the overlapping portion. For example, in the deployment configuration shown in FIG. 4, the coupling head of anchor 38E is positioned within second portion 112.

This configuration of implantable structure 22 may be implanted using the procedure described hereinabove with reference to FIGS. 2A-I, with the following differences. Unlike in the deployment shown in FIGS. 2G-I, in this configuration sleeve 26 is deployed as a closed band around the entire annulus of the native valve, including an anterior portion 116 of the annulus (on the aortic side of the valve) between fibrous trigones 142 and 144. Typically, both first and second portions 110 and 112 of sleeve 26 (and thus overlapping portion 114) are positioned along anterior portion 116 of the annulus.

For some applications, during the implantation procedure, the first sleeve end (i.e., the end of the sleeve to which contracting mechanism 28, e.g., housing 44 thereof, is closest) is placed along at least a portion of anterior portion 116 and first portion 110 is extended along this portion. At least one anchor 38D is deployed through the wall of first portion 110 of sleeve 26 into cardiac tissue at the anterior portion of the annulus. Additional anchors 38A and/or 38C are deployed through the wall of the sleeve around the non-anterior remainder of the annulus, including the posterior portion thereof, as described hereinabove with reference to FIG. 2H. (Anchors 38C, if provided, are deployed beyond the ends of the contracting portion of contracting member 30, while anchors 38A are deployed along the portion of the sleeve including the contracting portion of the contracting member.)

A portion of the sleeve is placed on at least a portion of anterior portion 116 of the annulus, and, typically, one or more anchors 38B are deployed through the wall of the sleeve into tissue at the anterior portion of the annulus.

The sleeve is further extended around the annulus until second portion 112 overlaps with previously-deployed first portion 110 at overlapping portion 114, forming a complete ring. At least one anchor 38E is deployed from within second portion 112 through the wall of the sleeve and into the cardiac tissue, typically at anterior portion 116 of the annulus, or at a portion of the annulus near anterior portion 116. Typically, anchor 38E is deployed such that it additionally passes through previously-deployed first portion 110 (passing through the wall of first portion 110 twice). (Optionally, anchors 38B and/or 38E are of a different configuration than anchors 38A, 38C, and/or 38D, such as described with reference to FIGS. 5A-I in above-mentioned US Patent Application Publication 2012/0330411; anchors 38B and 38E may be of the same configuration as one another, or of different configurations.)

Alternatively, the second sleeve end (i.e., the end of the sleeve to which second member end 53 is closest) is first placed at least partially along anterior portion 116, in which case second portion 112 is deployed before first portion 110, and anchor 38E is deployed from within first portion 110.

The sleeve may be deployed in either a clockwise direction or a counterclockwise direction, as viewed from the atrium.

Contracting assembly 40 is actuated, e.g., the rotatable structure of contracting mechanism 28 is rotated, in order to tighten implantable structure 22, as described hereinabove with reference to FIG. 2I. Typically, contracting member 30 does not extend along the portion of sleeve 26 deployed along anterior portion 116 of the annulus, and thus does not extend along first portion 110, second portion 112, or overlapping portion 114 of sleeve 26. The portion of the sleeve deployed along anterior portion 116 of the annulus (between the trigones) is thus non-contractible. For some applications, contracting member 30 is positioned along a non-anterior portion of the annulus, which non-anterior portion does not reach either of the fibrous trigones, e.g., does not reach within 5 mm of either of the trigones. Tightening of implantable structure 22 therefore tightens at least a portion of the posterior portion of the annulus, while preserving the length of anterior portion 116 of the annulus. (The anterior portion of the annulus should generally not be contracted because its tissue is part of the skeleton of the heart.) However, the portion of the sleeve deployed along the anterior portion of the annulus prevents dilation of the anterior annulus, because the sleeve is anchored at both ends of the anterior annulus, and, as mentioned above, the sleeve typically comprises a longitudinally non-extensible material. This deployment configuration may help prevent long-term resizing of the anterior annulus, which sometimes occurs after implantation of partial annuloplasty rings, such as C-bands.

For some applications, the non-contractible portion of sleeve 26 (the portion without contracting member 30) extends somewhat beyond one or both of trigones 142 or 144 (in the posterior direction, away from anterior portion 116 of the annulus), such as up to 20 mm, such as up to 10 mm. In general, since the non-contractible portions of the sleeve are preset, the surgeon is able to decide during the implantation procedure the lengths of the anterior non-contractible area and the posterior contractible area, by selecting the length of overlapping portion 114. The greater the length of overlapping portion 114, the greater the relative length of the posterior contractible portion, and the lesser the relative length of the non-contractible portion.

For some applications, at least one anchor 38C is coupled to cardiac tissue on the posterior side of right fibrous trigone 144, between the trigone and the end of contracting member 30. Similarly, at least one anchor 38C may be coupled to cardiac tissue on the posterior side of left fibrous trigone 142, between the trigone and the other end of contracting member 30 (which, for some applications, is coupled to contracting mechanism 28, as shown in FIG. 4).

For some applications, at least one (either one or both) of first and second longitudinal distances D1 and D2 (described hereinabove with reference to FIG. 1), taken separately, is greater than 40 mm, such as greater than 60 mm. This sleeve portion(s) beyond the contracting portion of contracting member 30 provide the non-contractible portion of the sleeve positioned along anterior portion 116 of the annulus, and, optionally, the non-contractible portion(s) that extend beyond the anterior portion.

Reference is still made to FIGS. 3 and 4. For some applications, anchors 38 deployed along anterior portion 116 of the annulus (between the trigones) are of a different configuration from anchors 38 deployed along the remainder of the annulus (including the posterior portion of the annulus). Unlike the remainder of the annulus, anterior portion 116 does not comprise muscular or fibrous tissue, but rather thinner aortic tissue (typically the anchors positioned along anterior portion 116 enter the aorta below the aortic leaflets). The anchors that are deployed along the remainder of the annulus are configured for strong coupling to the thicker and stronger fibrous tissue of these portions of the annulus. Such anchors may be inappropriate for coupling to anterior portion 116. Anchors 38 are thus provided that are particularly configured for coupling to anterior portion 116. For example, different configurations of anchors 38 are described with reference to FIGS. 5A-I in above-mentioned US Patent Application Publication 2012/0330411.

For these applications, anchors 38 include a plurality of first tissue anchors of a first configuration, and a plurality of second tissue anchors of a second configuration different from the first configuration. (The first tissue anchors are labeled 38A and 38C in FIG. 4, and for the sake of brevity, are referenced as 38A hereinbelow. The second tissue anchors are labeled 38B, 38D, and 38E in FIG. 4, and for the save of brevity, are referenced as 38B hereinbelow.) For some applications, implantable structure 22 comprises more first tissue anchors 38A than second tissue anchors 38B, e.g., at least twice as many first tissue anchors as second tissue anchors.

For these applications, sleeve 26 is typically arranged as a loop. For example, as described hereinabove with reference to FIG. 4, the sleeve may be shaped so as to define first and second sleeve ends, which are coupled to each other (optionally, with overlapping portion 114) to form the loop. Alternatively, as described hereinbelow with reference to FIG. 6, the sleeve may be shaped so as to define an integrally closed loop having no sleeve ends. First tissue anchors 38A are coupled to sleeve 26 at intervals along a first longitudinally-contiguous portion of the loop, and second tissue anchors 38B are coupled to sleeve 26 at intervals along a second longitudinally-contiguous portion of the loop different from the first longitudinally-contiguous portion. The second portion of the loop is deployed along anterior portion 116 of the annulus, and the first portion of the loop is deployed along at least a portion of the remainder of the annulus (including the posterior portion of the annulus).

Figure 5:
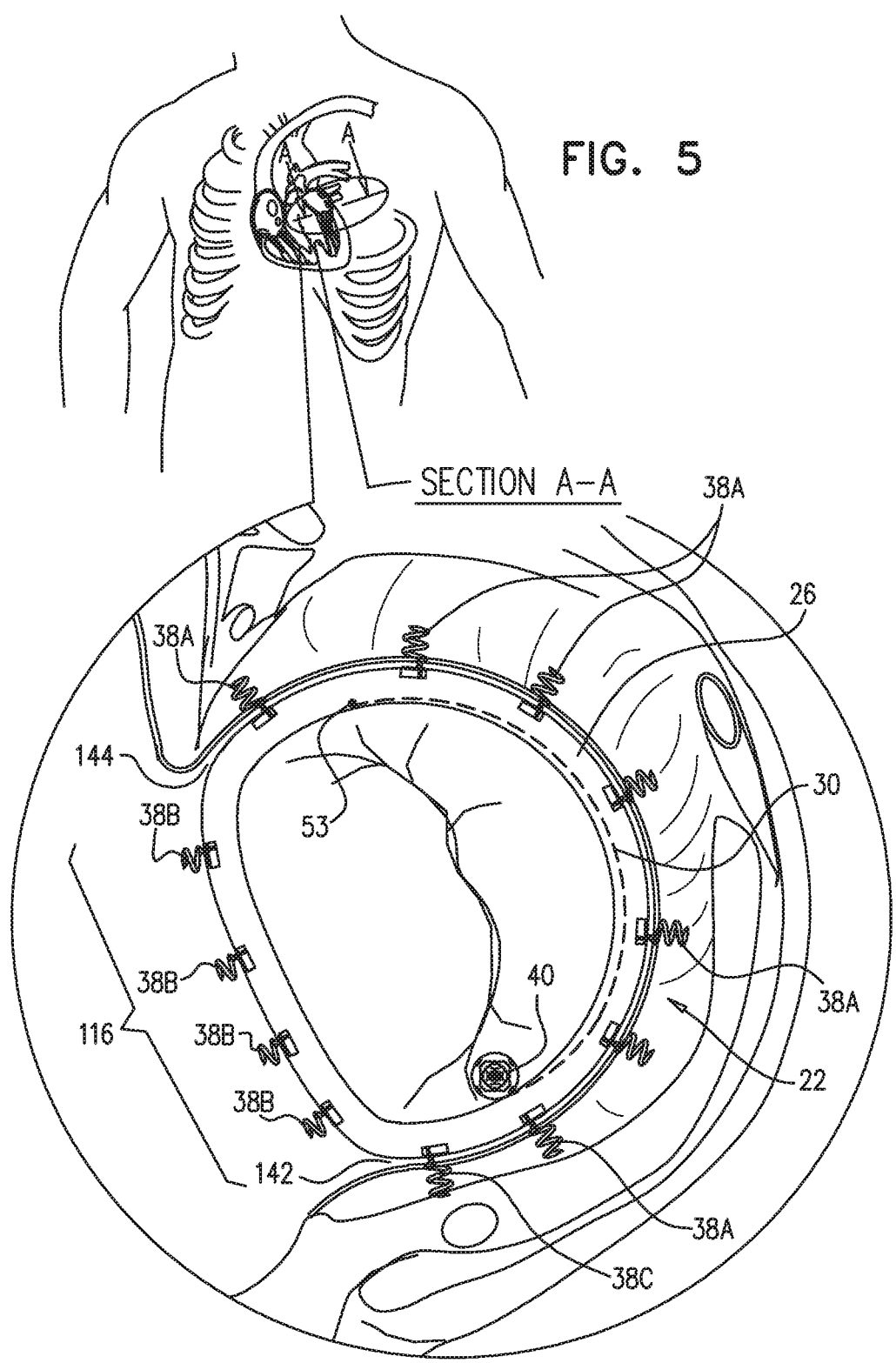
FIG. 5 is a schematic illustration of a closed-loop configuration of the implantable structure of FIG. 1, in accordance with an application of the present invention.

Reference is made to FIG. 5, which is a schematic illustration of an alternative closed-loop configuration of implantable structure 22, in accordance with an application of the present invention. In this configuration, flexible sleeve 26 is shaped so as to define an integrally closed loop having no sleeve ends. For some applications, anchors 38 deployed along anterior portion 116 of the annulus are of a different configuration from anchors 38 deployed along the remainder of the annulus, as described hereinabove with reference to FIGS. 3-4. The anchors may be configured as described with reference to FIGS. 5A-I in above-mentioned US Patent Application Publication 2012/0330411.

Typically, contracting member 30 does not extend along the portion of sleeve 26 deployed along anterior portion 116 of the annulus. The portion of the sleeve deployed along anterior portion 116 of the annulus (between the trigones) is thus non-contractible. Tightening of implantable structure 22 therefore tightens at least a portion of the posterior portion of the annulus, while preserving the length of anterior portion 116 of the annulus. (The anterior portion of the annulus should generally not be contracted because its tissue is part of the skeleton of the heart.) However, the portion of the sleeve deployed along the anterior portion of the annulus prevents dilation of the anterior annulus, because the sleeve is anchored at both ends of the anterior annulus, and, as mentioned above, the sleeve typically comprises a longitudinally non-extensible material. This deployment configuration may help prevent long-term resizing of the anterior annulus, which sometimes occurs after implantation of partial annuloplasty rings, such as C-bands.

For some applications, the non-contractible portion of sleeve 26 (the portion without contracting member 30) extends somewhat beyond one or both of trigones 142 or 144 (in the posterior direction, away from anterior portion 116 of the annulus), such as up to 20 mm, such as up to 10 mm.

For some applications, at least one anchor 38 is coupled to cardiac tissue on the posterior side of right fibrous trigone 144, between the trigone and the end of contracting member 30. Similarly, at least one anchor 38 may be coupled to cardiac tissue on the posterior side of left fibrous trigone 142, between the trigone and the other end of contracting member 30 (which, for some applications, is coupled to contracting mechanism 28, as shown in FIG. 5).

Figure 6:
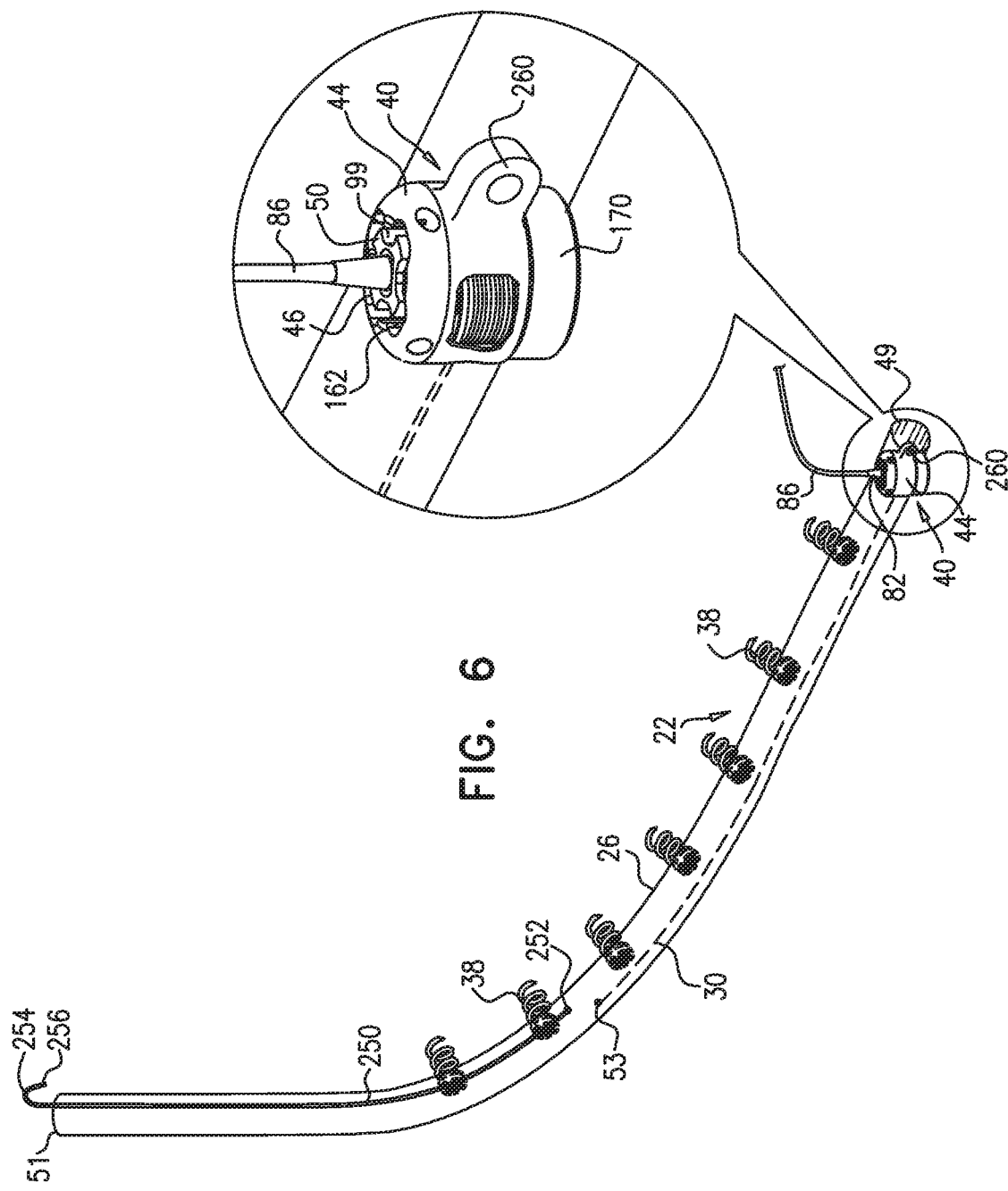
FIG. 6 is a schematic illustration of yet another configuration of the implantable structure of FIG. 1, prior to implantation, in accordance with an application of the present invention.
Figure 7A:
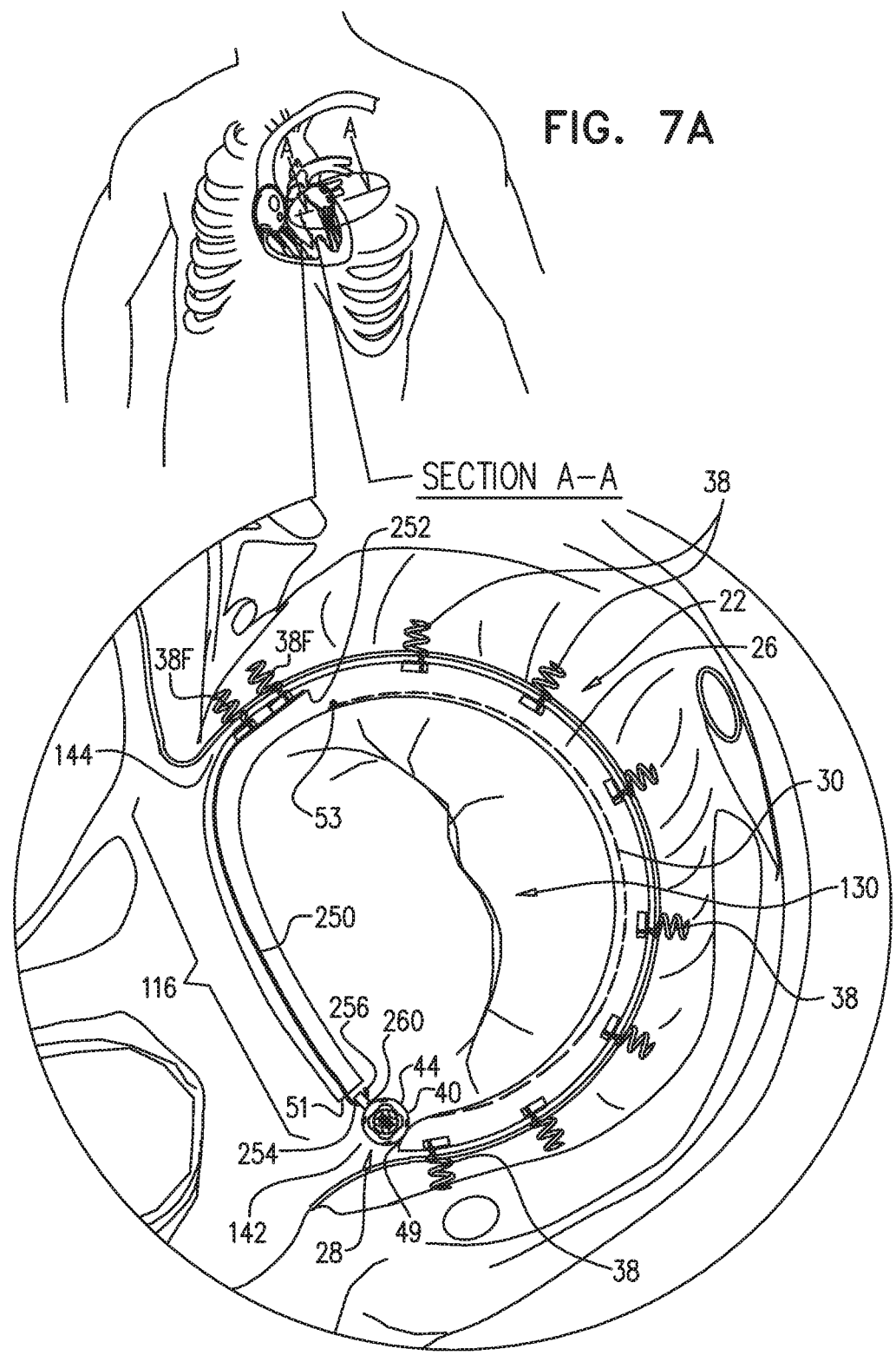
FIGS. 7A-B are schematic illustrations of the implantable structure of FIG. 6 after implantation around the annulus of a mitral valve, in accordance with respective applications of the present invention.
Figure 7B:
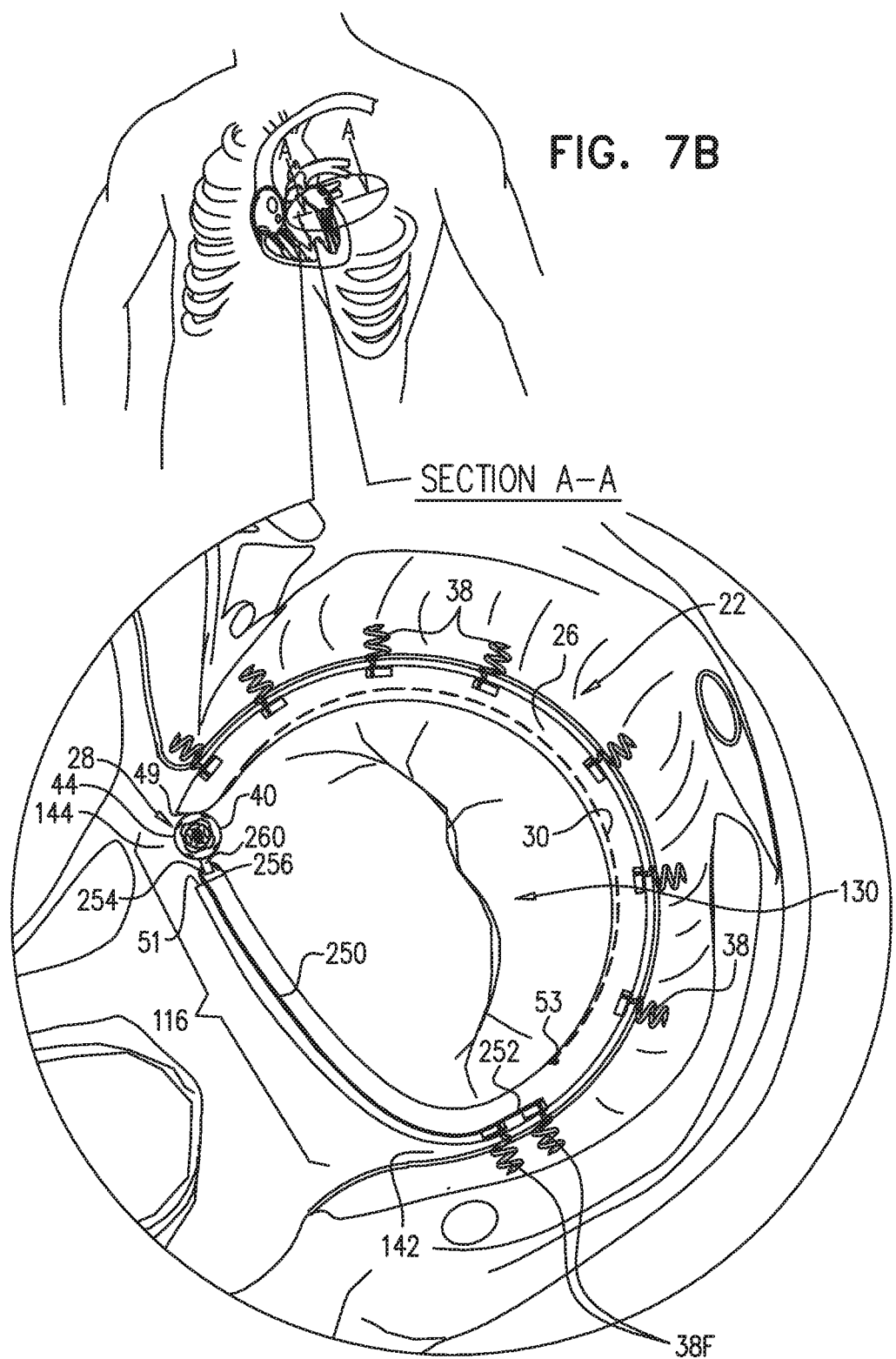

Reference is now made to FIGS. 6 and 7A-B, which are schematic illustrations of another configuration of implantable structure 22, in accordance with an application of the present invention. FIG. 6 shows implantable structure 22 in a relaxed, non-contracted state, and FIGS. 7A-B shows the implantable structure implanted around mitral valve 130. This configuration of implantable structure 22 is generally similar to the configuration described hereinabove with reference to FIG. 1, except as follows. In this configuration, implantable structure 22 further comprises an elongated linking member 250, which is positioned at least partially along anterior portion 116 of the annulus, so as to join the ends of implantable structure 22 in a complete loop. Over time after implantation, linking member 250 becomes fixed to anterior portion 116 of the annulus, thereby helping prevent long-term dilation of the anterior annulus. Typically, at least a portion (e.g., at least 30%, such as at least 75% or at least 90%) of a length of linking member 250 is disposed within and covered by sleeve 26, into and/or over which fibrous tissue grows over time, helping anchor the linking member to tissue of the anterior annulus. Alternatively or additionally, a separate flexible sleeve or a coating (e.g., a polymeric coating) may be provided that covers at least 20%, e.g., between 20% and 80%, of the linking member. Typically, in the configuration of implantable structure 22 shown in FIGS. 6 and 7A-B, none of anchors 38 is coupled to anterior portion 116 of the annulus. For some applications, as shown in FIG. 7A, implantable structure 22 is implanted with contracting mechanism 28 disposed near left fibrous trigone 142, while for other applications, as shown in FIG. 7B, implantable structure 22 is implanted with contracting mechanism 28 disposed near right fibrous trigone 144. This latter arrangement may facilitate placement of the first-deployed, distal-most anchor 38 near right fibrous trigone 144, which is above the fossa ovalis, and the linking of first and second coupling elements 256 and 260 later in the implantation procedure.

Linking member 250 has first and second linking member ends 252 and 254. Second linking member end 254 comprises (e.g., is shaped so as to define, or is fixed to) a first coupling element 256. First linking member end 252 is disposed longitudinally between second linking member end 254 and a first sleeve end (either proximal end 49, as shown, or distal end 51, not shown), exclusive. Second linking member end 254 either protrudes from the second end of the sleeve, or is recessed within the second end of the sleeve (as shown, the second end of the sleeve is distal end 51). A longitudinal portion of linking member 250 in a vicinity of first linking member end 252 is coupled to the sleeve. For example, the portion may be threaded through the fabric of the sleeve, and/or sewn (e.g., sutured) to the fabric of the sleeve to hold the linking member in place during deployment, and the linking member may be held in place after implantation by one or more of anchors 38, such as two or more anchors 38F. Optionally, the linking member is not initially coupled to the sleeve, but is instead held in place by a delivery tool during the implantation procedure, until being coupled to the sleeve by one or more of the anchors, for example. The coupled longitudinal portion may have a length of between 2 and 10 mm, and optionally includes first linking member end 252 of the linking member.

Implantable structure 22 further comprises a second coupling element 260, which is configured to be coupleable to first coupling element 256. Second coupling element 260 typically is coupled to implantable structure 22 within 1.5 cm of the first end of sleeve 26 (opposite the end mentioned above near which first linking member end 252 is fixed), measured when the sleeve is fully longitudinally extended.

As mentioned above, in the configuration shown in FIGS. 6 and 7A-B, this first end is proximal end 49.

For some applications, such as shown in FIGS. 6 and 7A-B, contracting mechanism 28 (e.g., housing 44 thereof) is disposed along sleeve 26 within 30 mm, such as within 15 mm, of the first sleeve end (i.e., the same end of the sleeve near which the second coupling element is coupled), measured when sleeve 26 is fully longitudinally extended. For example, contracting mechanism 28 (e.g., housing 44 thereof) may be fixed at the first sleeve end. Alternatively, for some applications, contracting mechanism 28 (e.g., housing 44 thereof) is fixed at least 5 mm from the first sleeve end, e.g., between 5 and 30 mm, such as between 5 and 15 mm, from the first sleeve end. Second coupling element 260 may be coupled to contracting mechanism 28 (e.g., to housing 44). Alternatively, second coupling element 260 may be otherwise coupled to sleeve 26 (such as directly coupled), in which case contracting mechanism 28, e.g., housing 44 thereof, may be coupled to sleeve 26 at a greater longitudinal distance from the end of the sleeve, and one or more of anchors 38 may be coupled to the sleeve longitudinally between the contracting mechanism and the sleeve end, such as described hereinabove with reference to FIGS. 1, 2A-I, 3, and 4.

Typically, linking member 250 is substantially longitudinally non-extensible, i.e., its length is fixed. Typically, linking member 250 comprises metal, such as Nitinol or stainless steel. For some applications, the linking member has a length of at least 2 cm, no more than 6 cm, and/or between 2 and 6 cm.

For some applications, the linking member is configured as a spring, which is typically curved, so as to be elastic in a radial direction, i.e., to be compressible like a bow or deflected beam. In these applications, the linking member is oriented such that it is pressed by elasticity against the anterior portion of the mitral annulus, i.e., the outer wall of the aorta, thereby holding the sleeve covering the linking member against the aortic wall.

For some applications, at least two of tissue anchors 38 are coupled to sleeve 26 at respective, different longitudinal sites alongside linking member 250, within 6 cm of first linking member end 252, such as within 2 to 6 cm of the first end. These tissue anchors may help set the proper direction of curvature of the linking member, for applications in which the linking member is curved.

Reference is made to FIGS. 8A-D, which are schematic illustrations of coupling elements 256 and 260, in accordance with respective applications of the present invention. For some applications, at least one of first and second coupling elements 256 and 260 comprises a hook 270. Alternatively or additionally, for some applications, at least one of the first and second coupling elements comprises a loop 272. In the configuration shown in FIG. 8A (and FIGS. 6 and 7A-B), first coupling element 256 comprises hook 270, and second coupling element 260 comprises a loop 272. In the configuration shown in FIG. 8B, both first and second coupling elements 256 and 260 comprises respective loops 272, and the coupling elements are coupled together such as by placing one of anchors 38 through both loops and into cardiac tissue.

Figure 8C:
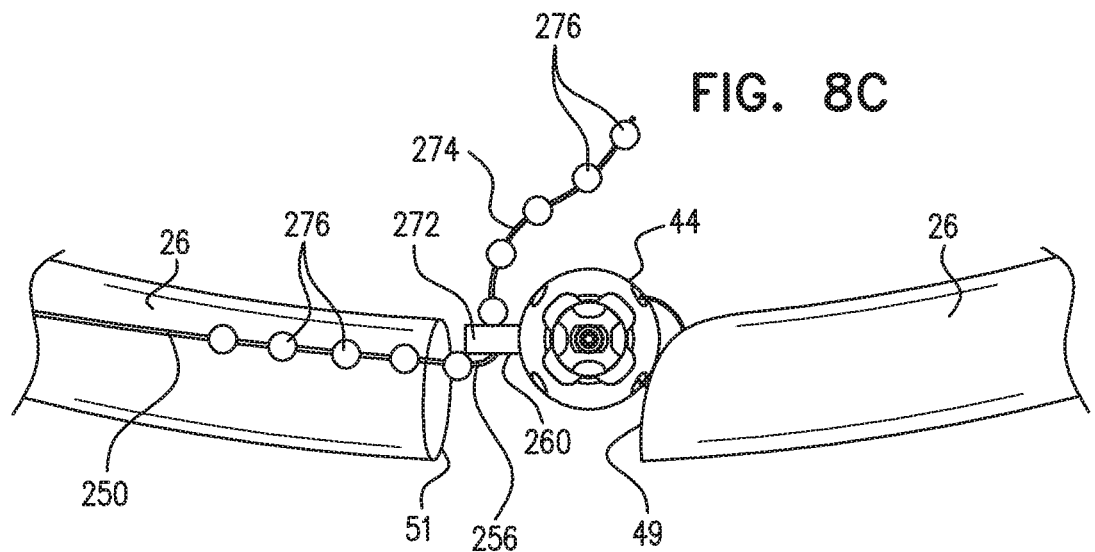
Figure 8D:
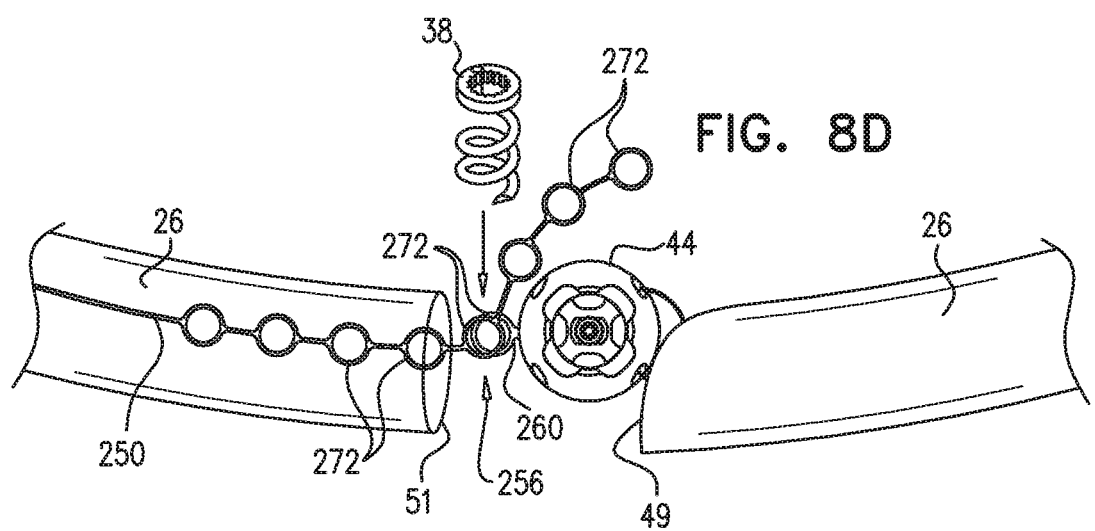

For some applications, first and second coupling elements 256 and 260 are configured to provide an adjustable-length connection between linking member 250 and the first end of sleeve. Such an adjustable-length connection allows the effective length of linking member 250 to be set during the implantation procedure in order to accommodate variations in individual patient anatomy. For some applications, such as shown in FIG. 8C, first coupling element 256 comprises a flexible elongate member 274, which comprises a plurality of protrusions 276 distributed along a portion of flexible elongate member 274. Flexible elongate member 274 is drawn through a loop defined by second coupling element 260 until a desired length of linking member 250 is achieved; one of the protrusions prevents loosening. Alternatively, second coupling element 260 comprises flexible elongate member 274 (having protrusions 276), and first coupling element 256 defines the loop through which flexible elongate member 274 is drawn (configuration not shown). For some applications, such as shown in FIG. 8D, first coupling element 256 comprises a plurality of loops 272, arranged longitudinally (each loop is connected to an adjacent loop, either directly or such as by a short length of wire), and second coupling element 260 comprises a single loop 272. The healthcare professional selects which of loops 272 of first coupling element 256 to couple with the single loop 272 of second coupling element 260, in order to set the length of linking member 250. Alternatively, second coupling element 260 comprises the plurality of loops 272, and first coupling element 256 comprises the single loop 272, or both first and second coupling elements 256 and 260 comprise pluralities of loops (configurations not shown).

Reference is now made to FIGS. 9-17, which are schematic illustrations of additional configurations of implantable structure 22, in accordance with respective applications of the present invention. FIGS. 9 and 12-16B show implantable structure 22 (which typically comprises an annuloplasty ring) in a relaxed, non-contracted state. FIGS. 11A-D show several configurations of an elongated radial-force application element 482, labeled with reference numerals 482A, 482B, 482C, and 482D, respectively. These configurations of implantable structure 22 are generally similar to the configuration described hereinabove with reference to FIG. 1, except as follows, and may incorporate any of the features of the configuration described hereinabove with reference to FIG. 1, mutatis mutandis.

Figure 10:
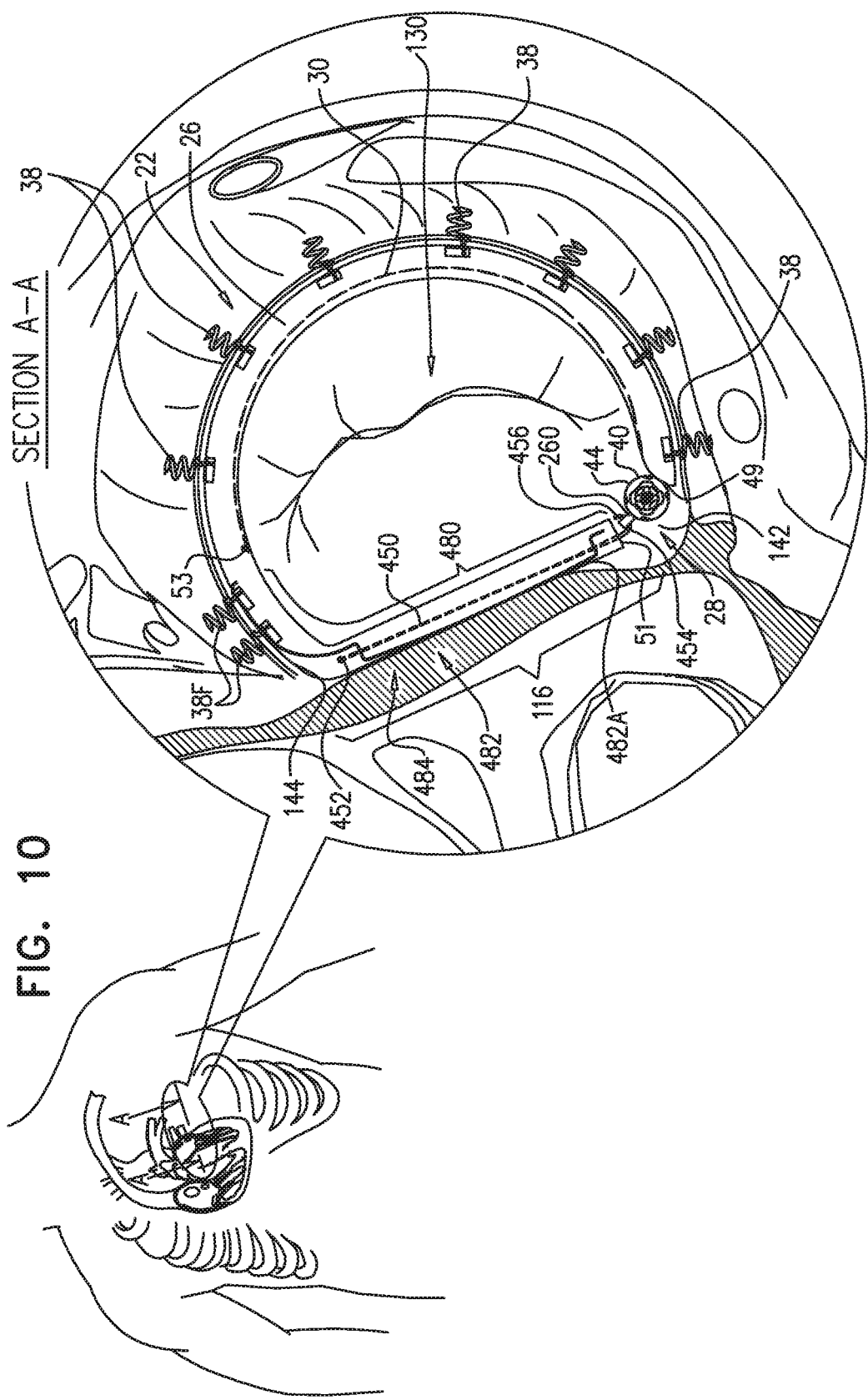
FIG. 10 is a schematic illustration of the implantable structure of FIG. 9 implanted around the mitral valve, in accordance with an application of the present invention.

FIG. 10 shows implantable structure 22 implanted around mitral valve 130, before a longitudinal portion of sleeve 26 has been contracted. For some applications, as shown in FIG. 10, implantable structure 22 is implanted with contracting mechanism 28 disposed near left fibrous trigone 142, while for other applications (not shown, but similar to the arrangement shown in FIG. 7B), implantable structure 22 is implanted with contracting mechanism 28 disposed near right fibrous trigone 144. This latter arrangement may facilitate placement of the first-deployed, distal-most anchor 38 near right fibrous trigone 144, which is above the fossa ovalis, and the linking of first and second coupling elements 456 and 260 later in the implantation procedure, for applications in which these coupling elements are provided, such as described hereinbelow.

In these configurations, implantable structure 22 further comprises elongated radial-force application element 482, which is disposed entirely within a first longitudinal portion of sleeve 26. Elongated radial-force application element 482 is configured to apply a force against a wall of the first longitudinal portion of sleeve 26 in at least one radially-outward direction. The applied force pushes the first longitudinal portion of sleeve 26 against tissue of the left atrium, such as against tissue of the annulus and/or the atrial wall, so as to inhibit blood flow between sleeve 26 and the tissue. It is generally desirable to inhibit blood flow between sleeve 26 and the annulus on anterior side, to avoid creating turbulence.

For some applications, elongated radial-force application element 482 is configured to apply a force against the wall of at least 20 gram-force, no more than 1 kg-force, and/or between 20 gram-force and 1 kg-force, such as at least 50 gram-force, no more than 500 gram-force (e.g., no more than 300 gram-force), and/or between 50 gram-force and 500 gram-force (e.g., between 50 gram-force and 300 gram-force). For some applications, elongated radial-force application element 482 is configured to apply the force generally constantly along the length of elongated radial-force application element 482, e.g., with a variation of less than 20% along the length.

When implanting implantable structure 22, elongated radial-force application element 482 is placed along anterior portion 116 of the annulus, between fibrous trigones 142 and 144 (a portion of elongated radial-force application element 482 may extend beyond one or both of the trigones, such as for coupling to anchors 38F, as described hereinbelow). If, upon initial placement, radial-force application element 482 does not apply the force against the wall of sleeve 26 in the desired radial direction (e.g., in the direction of the atrial wall), the healthcare professional may rotate the radial-force application element 482 within the sleeve, and/or rotate (e.g., twist) the first longitudinal portion of sleeve 26. Typically, longitudinal portion 480 extends along at least 20 mm of anterior portion 116 of the annulus, and/or along at least 20%, no more than 100%, and/or between 20% and 100% of anterior portion 116 of the annulus, such as at least 30%, no more than 60%, and/or between 30% and 60% of anterior portion 116. Typically, in the configuration of implantable structure 22 shown in FIGS. 9-10 and 12-16B, none of anchors 38 is coupled to anterior portion 116 of the annulus.

Typically, elongated radial-force application element 482 has a length of no more than 6 cm, measured when sleeve 26 is fully longitudinally extended.

For some applications, elongated radial-force application element 482 is rotationally asymmetric and not helically symmetric, such as shown in FIGS. 9-12 and 14-16B.

For some applications, such as shown in FIGS. 9-16B, elongated radial-force application element 482 comprises a springy element 484. For some applications, at least a portion of springy element 484 is curved at least partially about an inner surface of the wall of sleeve 26, such as shown in FIGS. 9, 10, 12, 14, 15, and 16A-B. Typically, springy element 484 comprises an elastic material, such as a metal, such as Nitinol or stainless steel.

Figure 11A:
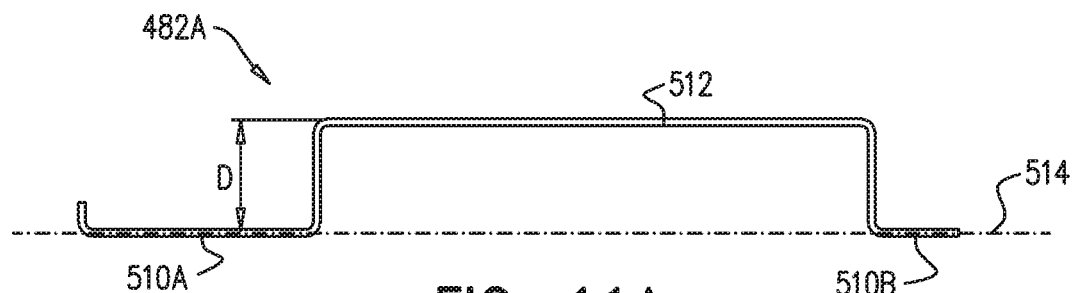
FIGS. 11A-D are schematic illustrations of several configurations of the elongated radial-force application element of the implantable structure of FIGS. 9 and 10, in accordance with an application of the present invention.
Figure 11B:
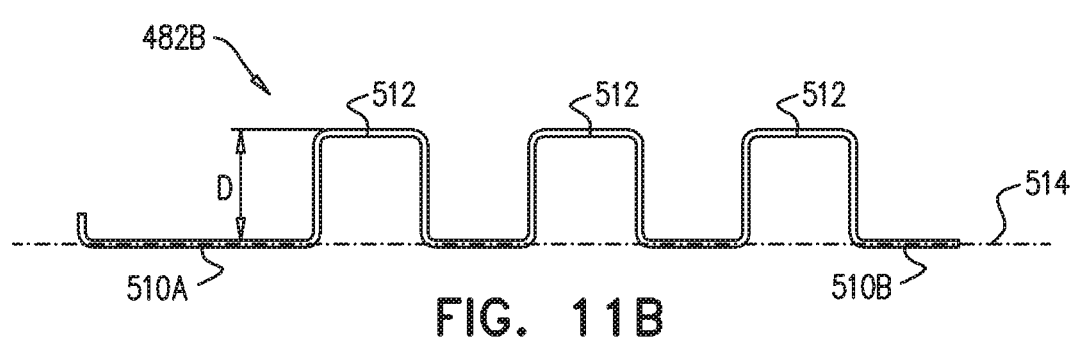
Figure 11C:
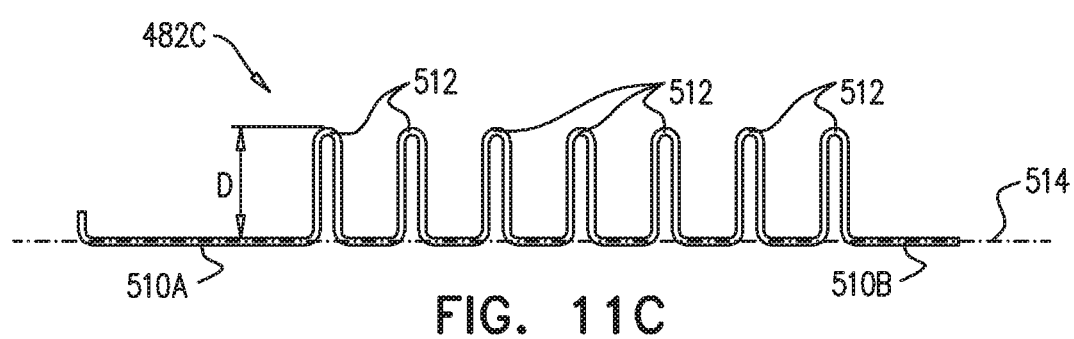
Figure 11D:
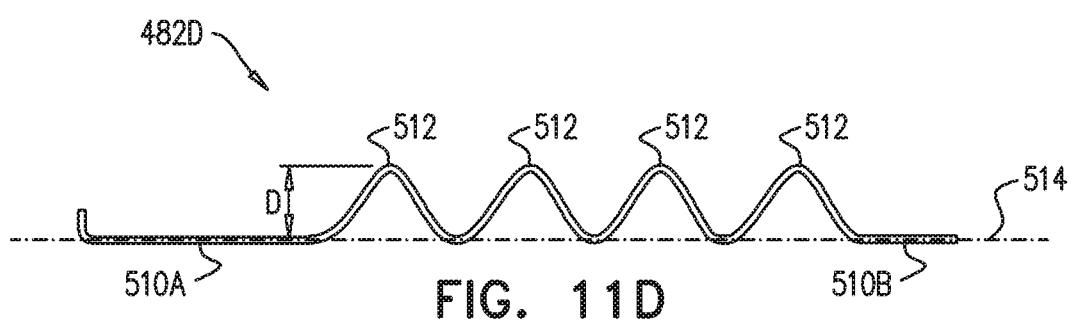

For some applications (such as when elongated radial-force application element 482 comprises springy element 484), as labeled in FIGS. 11A-D, elongated radial-force application element 482 is shaped so as to define one or more axial base sections 510 (e.g., exactly two axial base sections 510A and 510B, as shown in FIGS. 11A-D), and one or more offset sections 512 (e.g., exactly one offset section 512, as shown in FIG. 11A (and FIG. 10), or a plurality of offset sections 512 (e.g., between two and 20, e.g., between two and ten, such as between two and six), as shown in FIGS. 11B-D). The one or more axial base sections 510 are coaxial with a longitudinal axis 514 of elongated radial-force application element 482, and the one or more offset sections 512 are not coaxial with longitudinal axis 514. A greatest distance D between the one or more offset sections 512 and longitudinal axis 514 is typically at least 2 mm, no more than 10 mm (e.g., no more than 6 mm), and/or between 2 and 10 mm (e.g., between 2 and 6 mm), e.g., 4 mm.

For some applications, offset section(s) 512 are at least partially straight, such as shown in FIGS. 11A and 11B. For some applications, offset sections 512 are at least partially curved, such as shown in FIGS. 11C and 11D. For some applications, offset sections 512 are at least partially serpentine, such as shown in FIG. 11D.

Figure 12:
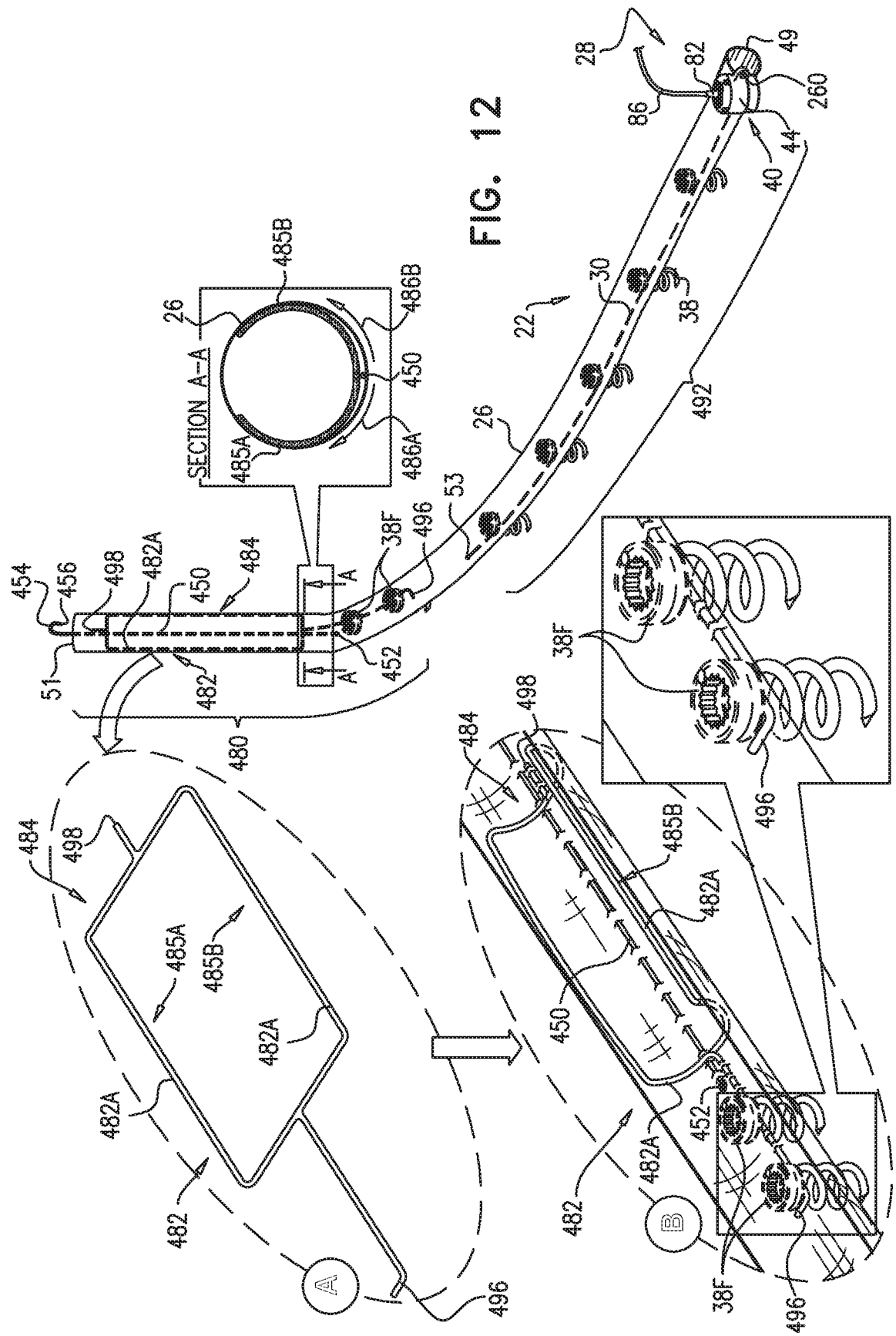
FIG. 12 is a schematic illustration of another configuration of the elongated radial-force application element of the implantable structure of FIGS. 9 and 10, in accordance with an application of the present invention.

For some applications, the at least a portion of springy element 484 is curved at least partially about the inner surface of the wall of sleeve 26 in a single circumferential direction, such as shown in FIGS. 9, 10, 14, 15, and 16A-B. Alternatively, for some applications, at least a first portion 485A of springy element 484 is curved at least partially about the inner surface of the wall of sleeve 26 in a first circumferential direction 486A, and at least a second portion 485B of springy element 484 is curved at least partially about the inner surface of the wall of sleeve 26 in a second circumferential direction 486B circumferentially opposite the first circumferential direction, such as shown in FIG. 12.

This configuration may use any of the shapes shown in FIGS. 11A-D (with the shapes doubled), or other shapes. This configuration pushes against the wall of sleeve 26 and the tissue at at least two circumferential locations around the sleeve, and may help hold the rotational position of the sleeve, allow less accurate rotational alignment, and/or help compensate for anatomical variability.

For some applications, such as shown in Section A-A of FIG. 9, elongated radial-force application element 482 is configured to apply the force against the wall of sleeve 26 around an angle α (alpha) that is less than 100% of a perimeter of the wall of sleeve 26 around a central longitudinal axis 516 of sleeve 26, such as around less than 75%, e.g., less than 50%, such as less than 25%, of the perimeter of the wall of sleeve 26. (Central longitudinal axis 516 runs along sleeve 26; the cross-section shown in Section A-A of FIG. 9 is perpendicular to the central longitudinal axis.) Force is not required to be applied around 100% of the perimeter of the wall of sleeve 26 because a circumferential portion of the wall faces the blood-filled volume of the chamber, rather than atrial tissue, and there would be no benefit to pushing the wall of sleeve 26 against the blood-filled volume.

Figure 13:
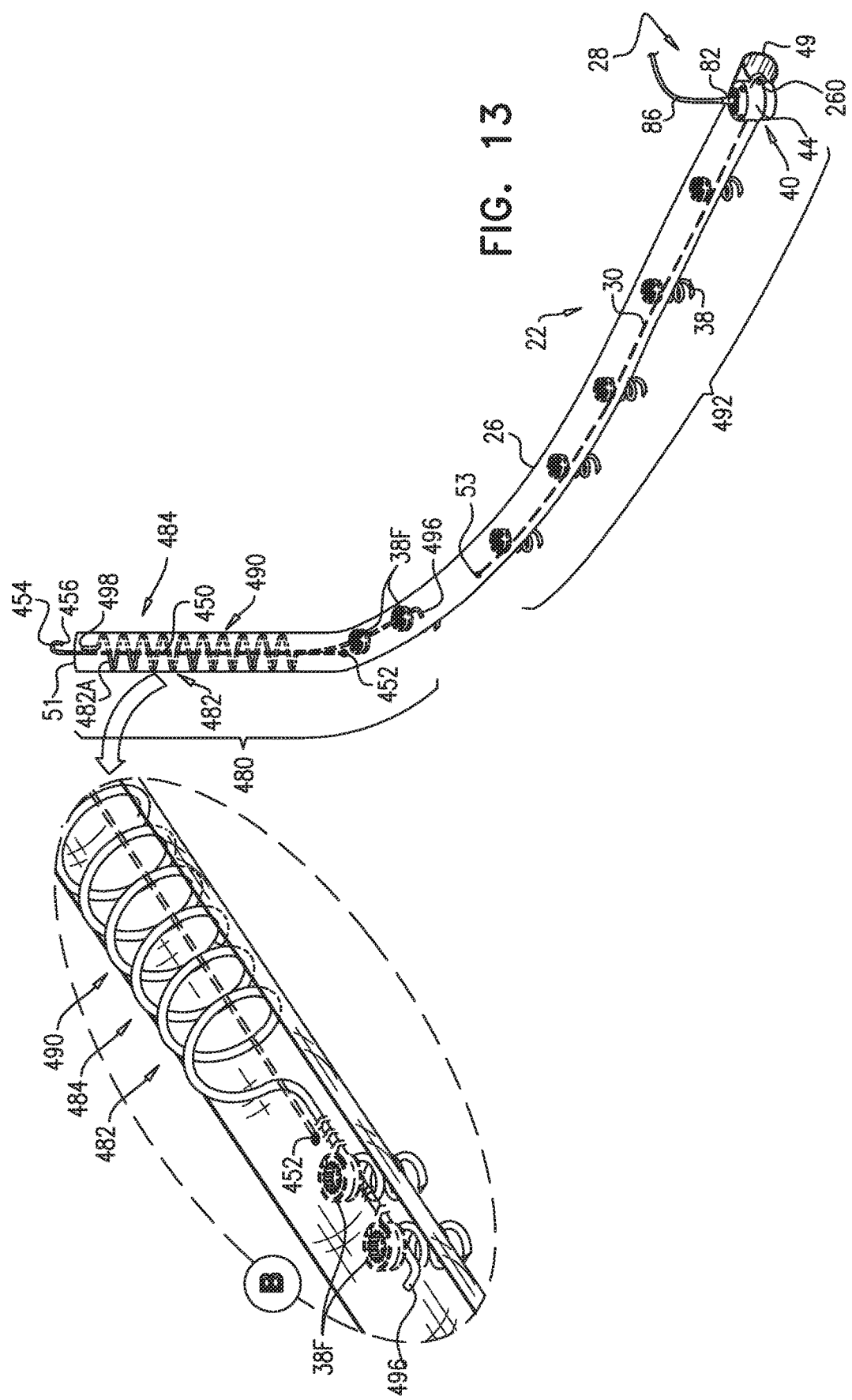
FIG. 13 is a schematic illustration of yet another configuration of the elongated radial-force application element of the implantable structure of FIGS. 9 and 10, in which the elongated radial-force application element is helically symmetric, in accordance with an application of the present invention.

For some applications, such as shown in FIG. 13, elongated radial-force application element 482 is helically symmetric; for these applications, springy element 484 typically comprises a coiled spring 490. For some applications, when in a relaxed state, coiled spring 490 has an outer diameter of at least 2.5 mm, no more than 10 mm, and/or between 2.5 and 10 mm, such as at least 3.5 mm, no more than 6 mm, and/or between 3.5 and 6 mm. For some applications, when in a relaxed state, the outer diameter of coiled spring 490 is greater than (e.g., equals at least 110% of, such as at least 130% of, e.g. at least 150% of) an inner diameter of a second longitudinal portion 492 that is entirely longitudinally distinct from first longitudinal portion 480 of sleeve 26, when second longitudinal portion 492 is fully radially expanded. Coiled spring 490 is typically initially held constrained with a smaller diameter in a separate tube smaller than the inner diameter of the deployment sheath.

Reference is again made to FIGS. 9-16B. For some applications, longitudinal contracting member 30 of contracting assembly 40 is arranged only along at least a portion of second longitudinal portion 492. For some of these applications, contracting assembly 40 is configured to contract the at least a portion of the second longitudinal portion 492.

Figure 14:
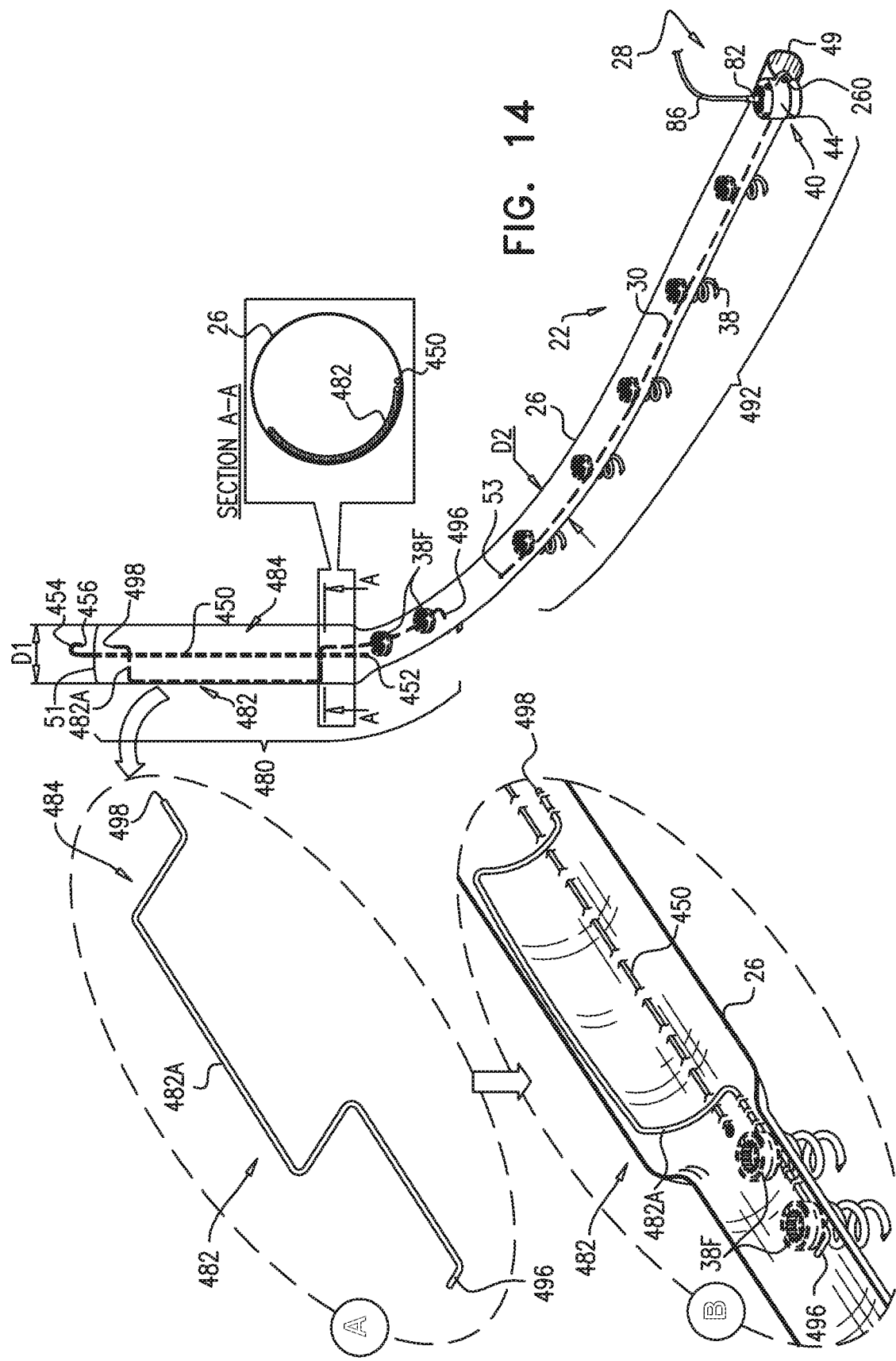
FIG. 14 is a schematic illustration of a configuration of the sleeve of the implantable structure of FIGS. 9 and 10, in accordance with an application of the present invention.

Reference is made to FIG. 14. For some applications, first and second longitudinal portions 480 and 492 of sleeve 26 are configured such that first longitudinal portion 480 either has, or is configured to assume, a first average internal diameter D1 that is greater than a second average internal diameter D2 of second longitudinal portion 492. For example, first average internal diameter D1 may be at least 110% of D2, such as at least 150% of second average internal diameter D2. This larger average diameter enables elongated radial-force application element 482 (e.g., springy element 484) to push a large surface area of sleeve 26 against the atrial tissue, thereby better encouraging tissue growth, better inhibiting blood between the sleeve and the atrial tissue, and accommodating variations in individual patient anatomy. For some applications, first and second longitudinal portions 480 and 492 collectively extend along an entire length of sleeve 26. This configuration, as well as the various options described below, may be used in combination with any of the configurations described herein with reference to FIGS. 9-13 and/or 15.

For some applications, first average internal diameter D1 of first longitudinal portion 480 of sleeve 26 is greater than second average internal diameter D2 of second longitudinal portion 492 of sleeve 26, when both first and second longitudinal portions 480 and 492 are fully radially expanded (in these applications, typically both first and second longitudinal portions 480 and 492 are substantially radially non-extensible).

For some other applications, first longitudinal portion 480 of sleeve 26 is radially elastic and thus able to stretch from an initial smaller average internal diameter to first average internal diameter D1, and second longitudinal portion 492 of sleeve 26 is substantially radially non-extensible, and thus cannot expand to a diameter beyond second average internal diameter D2. For example, first longitudinal portion 480 may comprise a first plurality of substantially non-extensible fibers that extend longitudinally along the first longitudinal portion, and a second plurality of elastic fibers that are arranged circumferentially around the first longitudinal portion (typically, woven with the first plurality of fibers). Typically, first and second longitudinal portions 480 and 492 of sleeve 26 are substantially longitudinally non-extensible, i.e., a length thereof is substantially constant, i.e., cannot be longitudinally stretched, under normal usage conditions. Optionally, first and second longitudinal portions 480 and 492 of sleeve 26 have a same diameter (equal to second average internal diameter D2) when first longitudinal portion 480 is not elastically stretched. Alternatively, for some applications, first and second longitudinal portions 480 and 492 of sleeve 26 are woven, and first longitudinal portion 480 of sleeve 26 is more loosely woven than second longitudinal portion 492 of sleeve 26. Further alternatively, for some applications, first longitudinal portion 480 of sleeve 26 is radially stretchable, and second longitudinal portion 492 of sleeve 26 is substantially radially non-extensible. For example, first longitudinal portion 480 may comprise a first plurality of substantially non-extensible fibers that extend longitudinally along the first longitudinal portion, and a second plurality of stretchable fibers that are arranged circumferentially around the first longitudinal portion (typically, woven with the first plurality of fibers).

For some applications, such as shown in FIGS. 9-10 and 12-15, sleeve 26 has (a) a first sleeve end 51 (which may correspond to distal end 51 of sleeve 26, as shown, or to the proximal end, configuration not shown), and (b) a second sleeve end 49 (which may correspond to proximal end 49 of sleeve 26, as shown, or to the distal end, configuration not shown). For some applications, elongated radial-force application element 482 has (a) a first radial-force-applicationelement longitudinal end 496 that is between 2 and 6 cm from first sleeve end 51, measured when sleeve 26 is fully longitudinally extended, and (b) a second radial-force-application-element longitudinal end 498 that is within 1.5 cm of first sleeve end 51, measured when sleeve 26 is fully longitudinally extended.

For some applications, such as shown in FIGS. 9-10 and 12-15, implantable structure 22 (e.g., the annuloplasty ring) further comprises (a) a first coupling element 456, which is coupled to the annuloplasty ring within 1.5 cm of first sleeve end 51, measured when sleeve 26 is fully longitudinally extended, and (b) second coupling element 260, as described above with reference to FIGS. 6 and 7A-B. Second coupling element 260 is configured to be coupleable to first coupling element 456, and is fixed to implantable structure 22 (e.g., the annuloplasty ring) within 1.5 cm of second sleeve end 49, measured when sleeve 26 is fully longitudinally extended. For some applications, at least one of first and second coupling elements 456 and 260 comprises a hook. Alternatively or additionally, for some applications, at least one of the first and second coupling elements comprises a loop. For example, in the configurations shown in FIGS. 9-15, first coupling element 456 comprises a hook, and second coupling element 260 comprises a loop. Alternatively, for example, both the first and the second coupling elements comprises loops, such as shown in FIGS. 8B and 8D, and the coupling elements are coupled together such as by placing one of anchors 38 through both loops and into cardiac tissue.

Elongated radial-force application element 482 is typically fixed to sleeve 26 at least near first radial-force-application-element longitudinal end 496, such that elongated radial-force application element 482 is arranged as a cantilever. Typically, elongated radial-force application element 482 is fixed to sleeve 26 at least near first radial-force-application-element longitudinal end 496, such that first radial-force-application-element longitudinal end 496 is rotationally fixed with respect to the sleeve, in order to allow twisting of elongated radial-force application element 482 to store spring energy in elongated radial-force application element 482 near first radial-force-application-element longitudinal end 496. The shape of first radial-force-application-element longitudinal end 496 may aid in rotationally fixing the end with respect to the sleeve. For example, first radial-force-application-element longitudinal end 496 may include a circumferentially-oriented component, as shown in the figures.

A portion of elongated radial-force application element 482 may be threaded through the fabric of the sleeve, and/or sewn (e.g., sutured) to the fabric of the sleeve to hold the elongated radial-force application element in place during deployment, and/or the elongated radial-force application element may be held in place after implantation by one or more of anchors 38, such as two or more anchors 38F.

For some applications, such as shown in FIGS. 9-15, contracting mechanism 28 (e.g., housing 44 thereof) is fixed along sleeve 26 within 30 mm, such as within 15 mm, of second sleeve end 49 (i.e., the same end of the sleeve near which second coupling element 260 is coupled), measured when sleeve 26 is fully longitudinally extended. For example, contracting mechanism 28 (e.g., housing 44 thereof) may be fixed at second sleeve end 49.

Alternatively, for some applications, contracting mechanism 28 (e.g., housing 44 thereof) is fixed at least 5 mm from second sleeve end 49, e.g., between 5 and 30 mm, such as between 5 and 15 mm, from second sleeve end 49. Second coupling element 260 may be coupled to contracting mechanism 28 (e.g., to housing 44). Alternatively, second coupling element 260 may be otherwise coupled to sleeve 26 (such as directly coupled), in which case contracting mechanism 28, e.g., housing 44 thereof, may be coupled to sleeve 26 at a greater longitudinal distance from the end of the sleeve, and one or more of anchors 38 may be coupled to the sleeve longitudinally between the contracting mechanism and the sleeve end, such as described hereinabove with reference to FIGS. 1, 2A-I, 3, and 4.

For some applications, such as shown in FIGS. 9-14, implantable structure 22 (e.g., the annuloplasty ring) further comprises a substantially longitudinally non-extensible linking member 450, i.e., a length thereof is substantially constant, i.e., cannot be longitudinally stretched, under normal usage conditions. Linking member 450 typically helps prevent long-term dilation of the anterior annulus. Linking member 450 is typically configured not to apply any force to the wall of first longitudinal portion 480 of sleeve 26.

Typically, linking member 450 is not configured as a spring. For some applications, linking member 450 comprises a metal (e.g., Nitinol or stainless steel) or a polymer. For some applications, linking member 450 is rigid, while for other applications, the linking member is not rigid.

Linking member 450 has first and second linking-member ends 452 and 454. Linking member 450 is at least partially disposed within and covered by first longitudinal portion 480 of sleeve 26. Typically, at least 30%, such as at least 75% or at least 90% of a length of linking member 450 is disposed within and covered by first longitudinal portion 480 of sleeve 26. Over time after implantation, linking member 450 becomes fixed to anterior portion 116 of the annulus. Second linking-member end 454 comprises (e.g., is shaped so as to define, or is fixed to) first coupling element 456. Second linking-member end 454 either protrudes from first sleeve end 51, or is recessed within first sleeve end 51. A longitudinal portion of linking member 450 in a vicinity of first linking-member end 452 is typically coupled to sleeve 26. For example, the portion may be threaded through the fabric of the sleeve, and/or sewn (e.g., sutured) to the fabric of the sleeve to hold the linking member in place during deployment. Optionally, a longitudinal portion of linking member 450 in a vicinity of first linking-member end 452 is held in place after implantation by one or more of anchors 38, such as two or more anchors 38F (configuration not shown). Optionally, the linking member is not initially coupled to the sleeve, but is instead held in place by a delivery tool during the implantation procedure, until being coupled to the sleeve during the implantation procedure. Typically, linking member 250 has a length of at least 2 cm, no more than 6 cm, and/or between 2 and 6 cm.

For some applications, at least first longitudinal portion 480 of sleeve 26 is substantially longitudinally non-extensible, i.e., a length thereof is substantially constant, i.e., cannot be longitudinally stretched, under normal usage conditions. In these applications, first longitudinal portion 480 typically helps prevent long-term dilation of the anterior annulus.

For some applications, such as shown in FIG. 15, first coupling element 456 is fixed to the wall of sleeve 26 within 1.5 cm of first sleeve end 51, measured when sleeve 26 is fully longitudinally extended. Implantable structure 22 typically does not comprise linking member 450 in these applications. In these applications, at least first longitudinal portion 480 of sleeve 26 is substantially longitudinally non-extensible, and first longitudinal portion 480 typically helps prevent long-term dilation of the anterior annulus.

Reference is made to FIGS. 9-15. Typically, sleeve 26 is placed entirely around an annulus of the atrioventricular valve, e.g., the mitral valve. For applications in which sleeve 26 has first and second sleeve ends 51 and 49, as described hereinabove with reference to FIGS. 9-14, sleeve 26 is introduced into the left atrium while first and second sleeve ends 51 and 49 are not coupled to each other, and thereafter, in the left atrium, sleeve 26 is arranged entirely around the annulus to form the closed loop.

Reference is still made to FIGS. 9-16. For some applications, during placement, after fastening sleeve 26 to the portion of the annulus, the healthcare professional twists elongated radial-force application element 482 (and optionally first longitudinal portion 480 of sleeve 26), and then, typically, links first and second coupling elements 456 and 260. Optionally, such twisting may serve one or both of the following purposes: (1) the twisting may store energy in springy element 484 for exertion of torque against the wall of the sleeve, and (2) the twisting may rotationally align springy element 484 in the desired radial direction. Alternatively or additionally to twisting for the first of these purposes, springy element 484 may be pre-loaded (twisted) to store energy before implantation in the subject, such as immediately before implantation or during manufacture.

Reference is again made to FIGS. 8A-D. The techniques described with reference to these figures regarding coupling element 256 may be implemented for coupling element 456 of the configuration described with reference to FIGS. 9-15.

Reference is made to FIGS. 16A-B, which are schematic illustrations of implantable structure 22 in which sleeve 26 is shaped so as to define an integrally closed loop having no sleeve ends, in accordance with respective applications of the present invention. In these applications, the wall of sleeve 26 typically is shaped so as to define a lateral opening 500 through which anchor deployment manipulator 24 is introduced. For some applications, elongated radial-force application element 482 has (a) a first radial-force-application-element longitudinal end 496 that is at least 2 cm, no more than 6 cm, and/or between 2 and 6 cm from housing 44 of contracting assembly 40 (housing 44 is fixed to sleeve 26), measured when sleeve 26 is fully longitudinally extended, and (b) a second radial-force-application-element longitudinal end 498 that is within 1.5 cm of housing 44, measured when sleeve 26 is fully longitudinally extended. Alternatively, for some applications, first radial-force-application-element longitudinal end 496 is within 1.5 cm of housing 44, measured when sleeve 26 is fully longitudinally extended, and second radial-force-application-element longitudinal end 498 is at least 2 cm, no more than 6 cm, and/or between 2 and 6 cm from housing 44 of contracting assembly 40, measured when sleeve 26 is fully longitudinally extended.

For some applications, such as shown in FIG. 16B, first and second longitudinal portions 480 and 492 of sleeve 26 are configured such that first longitudinal portion 480 either has, or is configured to assume, a first average internal diameter D1 that is greater than a second average internal diameter D2 of second longitudinal portion 492. For example, first average internal diameter D1 may be at least 110% of second average internal diameter D2, such as at least 150% of second average internal diameter D2. First average internal diameter D1 may be achieved using the techniques described hereinabove with reference to FIG. 14. For other applications, such as shown in FIG. 16A, the entire sleeve (i.e., first and second longitudinal portions 480 and 492) has a constant internal diameter.

For some applications, as shown in FIGS. 16A-B, implantable structure 22 is implanted with contracting mechanism 28 disposed near left fibrous trigone 142, while for other applications (not shown, but similar to the arrangement shown in FIG. 7B), implantable structure 22 is implanted with contracting mechanism 28 disposed near right fibrous trigone 144.

Reference is now made to FIG. 17, which is a schematic illustration of another configuration of implantable structure 22 implanted around the mitral valve, in accordance with an application of the present invention. In this configuration, elongated radial-force application element 482 comprises an inflatable element 494, such as a balloon. After fastening sleeve 26 to the portion of the annulus (and, optionally, after linking first and second coupling elements 456 and 260), the healthcare professional inflates inflatable element 494, typically with a liquid (such as saline solution) or a gel. For some applications, inflatable element 494 is provided separately from implantable structure 22, and the healthcare professional introduces inflatable element 494, while uninflated, into sleeve 26, typically after fastening sleeve 26 to the portion of the annulus (and, optionally, after linking first and second coupling elements 456 and 260), and then inflates inflatable element 494. These inflation techniques may be used with any of the techniques described herein with reference to FIGS. 9-16B, mutatis mutandis.

For some applications, as shown in FIG. 17, implantable structure 22 is implanted with contracting mechanism 28 disposed near left fibrous trigone 142, while for other applications (not shown, but similar to the arrangement shown in FIG. 7B), implantable structure 22 is implanted with contracting mechanism 28 disposed near right fibrous trigone 144. This latter arrangement may facilitate placement of the first-deployed, distal-most anchor 38 near right fibrous trigone 144, which is above the fossa ovalis, and the linking of first and second coupling elements 456 and 260 later in the implantation procedure, for applications in which these coupling elements are provided, such as described hereinbelow.

Figure 18B:
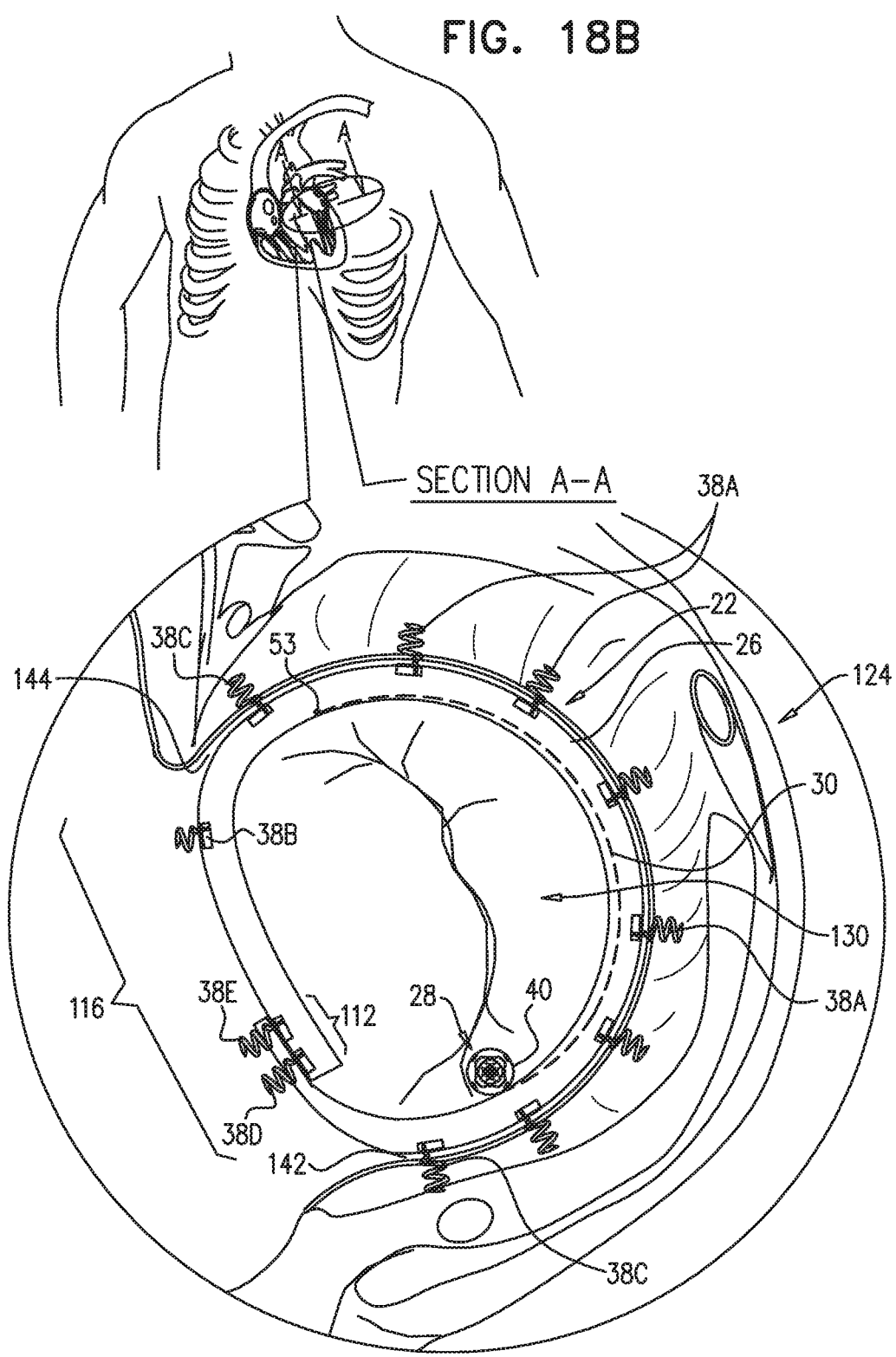

Reference is now made to FIGS. 18A and 18B. FIG. 18A is a schematic illustration of another configuration of implantable structure 22, prior to implantation, in accordance with an application of the present invention, and FIG. 18B is a schematic illustration of implantable structure 22 in the configuration of FIG. 18A after implantation entirely around the annulus of mitral valve 130, before a longitudinal portion of sleeve 26 has been contracted, in accordance with an application of the present invention. In this configuration, flexible sleeve 26 is placed entirely around an annulus of mitral valve 130 in a closed loop. For some applications, sleeve 26 is introduced into left atrium 124 while first and second sleeve ends are not coupled to each other. Thereafter, in the left atrium, the sleeve is arranged entirely around the annulus to form the closed loop.

Sleeve 26 is fastened to the annulus by coupling a plurality of tissue anchors 38 to the annulus. Tissue anchors 38 are coupled with:
  a first non-zero longitudinal density along a posterior portion of the annulus between left and right fibrous trigones 142 and 144 of the annulus, including the trigones, which density is equal to (a) a number of tissue anchors 38 coupled to the annulus along the posterior portion of the annulus divided by (b) a length of the posterior portion of the annulus (measured along the annulus),
  and a second non-zero longitudinal density along an anterior portion of the annulus between left and right fibrous trigones 142 and 144 of the annulus, not including the trigones, which density is equal to (a) a number of tissue anchors 38 coupled to the annulus along the anterior portion of the annulus divided by (b) a length of the anterior portion of the annulus (measured along the annulus).

The first longitudinal density is greater than the second longitudinal density. For some applications, the first longitudinal density is at least twice the second longitudinal density, such as at least 2.5 the second longitudinal density, e.g., at least 3 times the second longitudinal density. For example, tissue anchors 38A (and, optionally 38C) may be fastened along the posterior portion of the annulus, and tissue anchors 38B may be fastened along the anterior portion of the annulus. After the tissue anchors are fastened to the annulus, a longitudinal portion of the sleeve is contracted, such as by causing the longitudinal contracting member to apply a force to the longitudinal portion of the sleeve, such as by actuating contracting assembly 40.

Alternatively or additionally, for some applications, sleeve 26 comprises a plurality of radiopaque markers 39, which are positioned along the sleeve at respective longitudinal sites, such as described hereinabove with reference to FIG. 1. The markers may provide an indication in a radiographic image (such as a fluoroscopy image) of how much of the sleeve has been deployed at any given point during an implantation procedure, in order to enable setting a desired distance between anchors 38 along the sleeve, and thus the desired differing longitudinal densities of the anchors.

For some applications, as shown in FIG. 18B, implantable structure 22 is implanted with contracting mechanism 28 disposed near left fibrous trigone 142, while for other applications (not shown, but similar to the arrangement shown in FIG. 7B), implantable structure 22 is implanted with contracting mechanism 28 disposed near right fibrous trigone 144.

Figure 19:
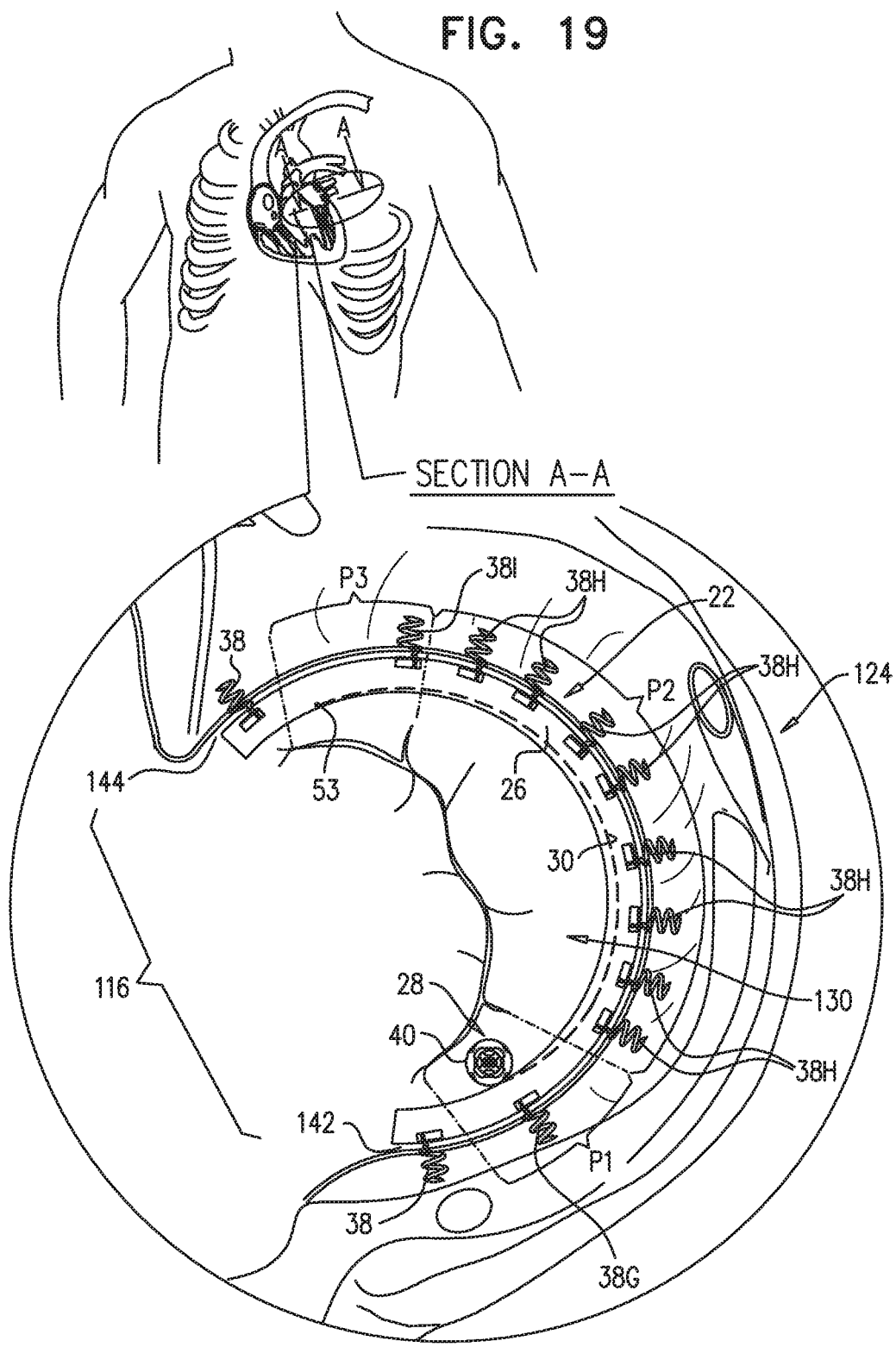
FIG. 19 is a schematic illustration of still another configuration of the implantable structure of FIG. 1 implanted around the mitral valve, in accordance with an application of the present invention.

Reference is now made to FIG. 19, which is a schematic illustration of implantable structure 22 after implantation around the annulus of mitral valve 130, in accordance with an application of the present invention. In this configuration, flexible sleeve 26 is placed at least partially around an annulus of mitral valve 130, such as partially around the annulus, as shown in FIG. 19, or entirely around the annulus in a closed loop, such as shown in FIG. 4, 5, 7A-B, 10, 16A-B, 17, or 18B, optionally using any of the techniques described herein with reference to these figures. For some applications in which the sleeve is placed entirely around the annulus, sleeve 26 is introduced into left atrium 124 while first and second sleeve ends are not coupled to each other; thereafter, in the left atrium, sleeve 26 is arranged entirely around the annulus to form the closed loop. FIG. 19 shows the annulus before a longitudinal portion of sleeve 26 has been contracted, as described below.

Sleeve 26 is fastened to the annulus by coupling a plurality of tissue anchors 38 to the annulus, including first, second, and third tissue anchors 38G, 38H, and 38I, as follows:

one or more first tissue anchors 38G are coupled to the annulus along a lateral scallop (P1) of the posterior leaflet, with a first longitudinal density, which density is equal to (a) a number of first tissue anchors 38G coupled to the annulus along the lateral scallop (P1) divided by (b) a length of the lateral scallop (P1) along the annulus, a plurality of second tissue anchors 38H (e.g., at least 3 tissue anchors, such as at least five tissue anchors) are coupled to the annulus along a middle scallop (P2) of the posterior leaflet, with a second longitudinal density, which density is equal to (a) a number of second tissue anchors 38H coupled to the annulus along the middle scallop (P2) divided by (b) a length of the middle scallop (P2) along the annulus, and one or more third tissue anchors 38I are coupled to the annulus along a medial scallop (P3) of the posterior leaflet, with a third longitudinal density, which density is equal to (a) a number of third tissue anchors 38I coupled to the annulus along the medial scallop (P3) divided by (b) a length of the medial scallop (P3) along the annulus.

Tissue anchors 38 may optionally comprise additional tissue anchors other than tissue anchors 38G, 38H, and 38I, not coupled along the posterior leaflet. After the tissue anchors are fastened to the annulus, a longitudinal portion of sleeve 26 is contracted, such as by causing the longitudinal contracting member to apply a force to the longitudinal portion of the sleeve, such as by actuating contracting assembly 40.

The longitudinal densities are characterized by at least one of the following: (a) the second longitudinal density is at least twice the first longitudinal density (such as at least 2.5 the first longitudinal density, e.g., at least 3 times the first longitudinal density), and (b) the second longitudinal density is at least twice the third longitudinal density (such as at least 2.5 the third longitudinal density, e.g., at least 3 times the third longitudinal density). For some applications, both (a) the second longitudinal density is at least twice the first longitudinal density (such as at least 2.5 the first longitudinal density, e.g., at least 3 times the first longitudinal density), and (b) the second longitudinal density is at least twice the third longitudinal density (such as at least 2.5 the third longitudinal density, e.g., at least 3 times the third longitudinal density).

For some applications, as shown in FIG. 19, implantable structure 22 is implanted with contracting mechanism 28 disposed near left fibrous trigone 142, while for other applications (not shown, but similar to the arrangement shown in FIG. 7B), implantable structure 22 is implanted with contracting mechanism 28 disposed near right fibrous trigone 144.

Figure 20:
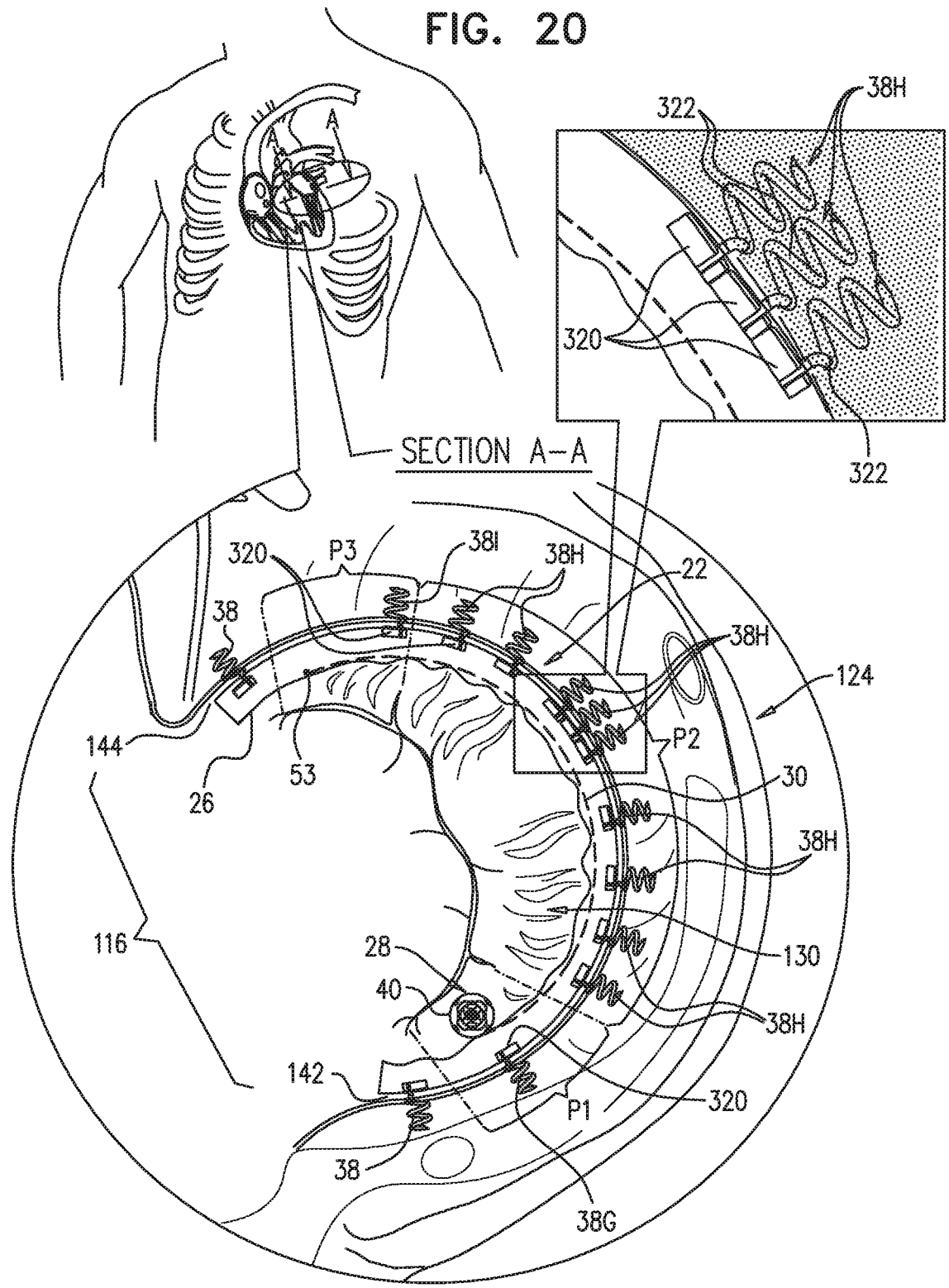
FIG. 20 is a schematic illustration of another configuration of the implantable structure of FIG. 1 implanted around the mitral valve, in accordance with an application of the present invention.
Figure 21:
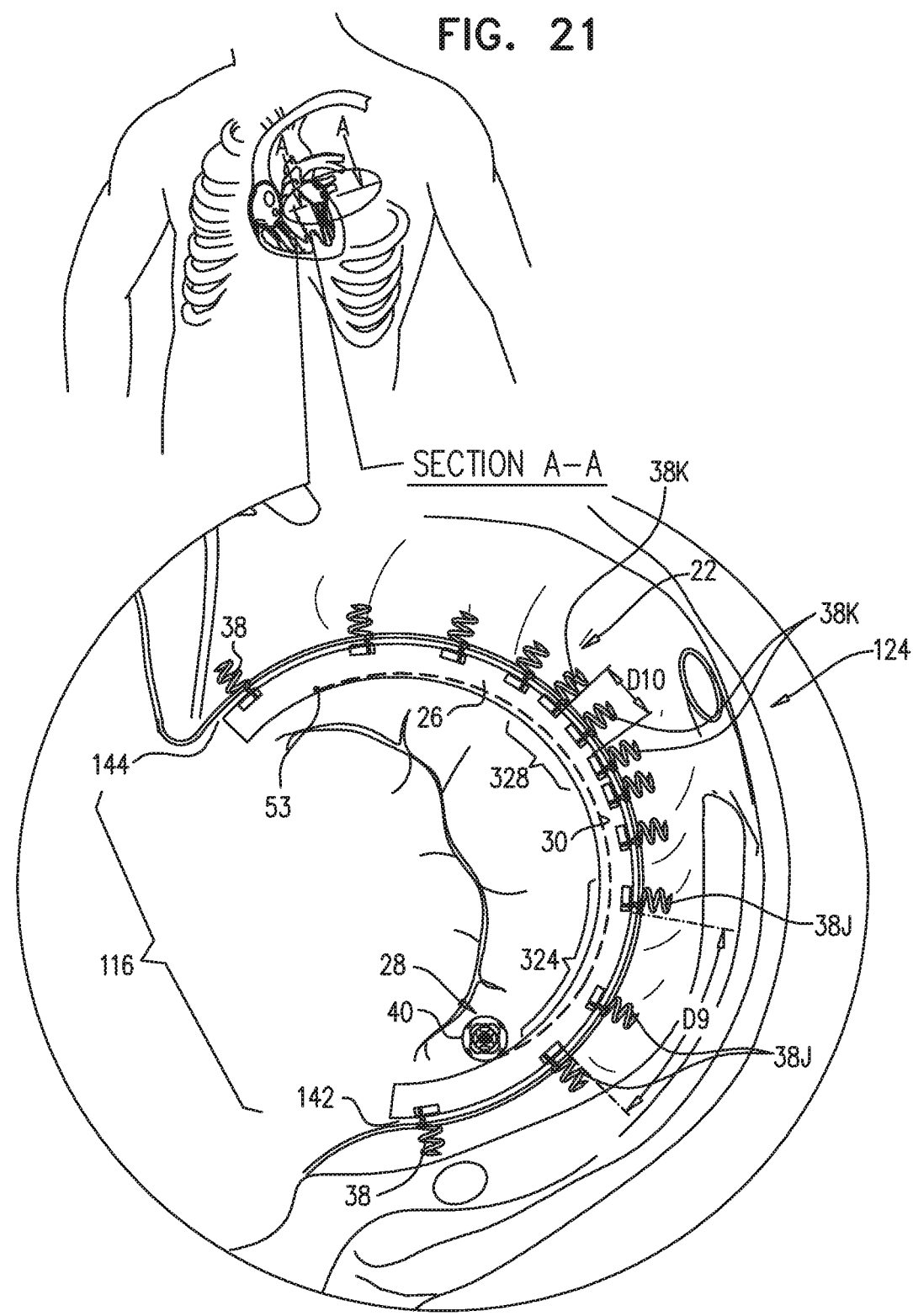

Reference is now made to FIG. 20, which is a schematic illustration of implantable structure 22 after implantation around the annulus of mitral valve 130, in accordance with an application of the present invention. FIG. 20 shows implantable structure 22 after a longitudinal portion of sleeve 26 has been contracted, such as by actuating contracting assembly 40. The techniques described with reference to FIG. 20 may optionally be used in combination with the techniques described above with reference to FIG. 19.

Tissue anchors 38, including second tissue anchors 38H, comprise respective anchor heads 320 and tissue coupling elements 322. Typically, anchor heads 320 are circular; alternatively, they have another shape, such as of an ellipse or a polygon (e.g., a hexagon or a square). The plurality of tissue anchors 38 are coupled to the annulus such that, after the longitudinal portion of sleeve 26 has been contracted (such as by actuating contracting assembly 40 to contract the longitudinal portion), each of anchor heads 320 of at least two of second tissue anchors 38H coupled along the middle scallop (P2) touches at least one longitudinally-adjacent anchor head 320; for example, each of anchor heads 320 of at least three of tissue anchors 38H touches at least one longitudinally-adjacent anchor head 320.

Typically, before the longitudinal portion of sleeve 26 has been contracted, anchor heads 320 of the at least two of second tissue anchors 38H do not touch any longitudinally-adjacent anchor heads 320. Before the longitudinal portion of sleeve 26 has been contracted, the anchors are coupled to the sleeve and tissue at distances between the anchors that are less than the planned distances that the anchors move toward each other during contraction of the longitudinal portion of sleeve 26. As a result, the anchor heads touch each other upon such contraction.

By way of example, FIG. 20 shows three of tissue anchors 38H touching at least one longitudinally-adjacent anchor head 320. Each of the longitudinally-outer touching anchor heads touches one longitudinally-adjacent anchor head (the middle longitudinally-touching anchor head), and the middle longitudinally-touching anchor head touches two longitudinally-adjacent anchor heads (the outer touching anchor heads).

This touching of longitudinally-adjacent anchor heads 320 inhibits longitudinal contraction of sleeve 26 in the longitudinal area of these anchors, so as to facilitate reshaping of the annulus in a desired manner. These longitudinally-adjacent anchor heads 320 thus are dual-function, and serve to both anchor their respective anchors to the sleeve and to inhibit contraction of the sleeve.

For some applications, as shown in FIG. 20, the plurality of tissue anchors 38 is coupled to the annulus such that, after the longitudinal portion of sleeve 26 has been contracted, such as by causing the longitudinal contracting member to apply a force to the longitudinal portion of the sleeve, such as by actuating contracting assembly 40:
  none of anchor heads 320 of first tissue anchors 38G coupled along the lateral scallop (P1) touches any of the other anchor heads of tissue anchors 38; and/or
  none of anchor heads 320 of third tissue anchors 38I coupled along the medial scallop (P3) touches any of the other anchor heads of tissue anchors 38.

For some applications, the plurality of tissue anchors 38 are coupled to the annulus such that, after the longitudinal portion of sleeve 26 has been contracted, such as by causing the longitudinal contracting member to apply a force to the longitudinal portion of the sleeve, such as by actuating contracting assembly 40:
  a first number of anchor heads 320 of first tissue anchors 38G coupled along the lateral scallop (P1) touch at least one longitudinally-adjacent anchor head, and (b) a second number of anchor heads 320 of the tissue anchors coupled along the middle scallop (P2) touch at least one longitudinally-adjacent anchor head, the second number greater than the first number; and/or
  a second number of anchor heads 320 of second tissue anchors 38H coupled along the middle scallop (P2) touch at least one longitudinally-adjacent anchor head, and (b) a third number of anchor heads 320 of third tissue anchors 38I coupled along the medial scallop (P3) touch at least one longitudinally-adjacent anchor head, the second number greater than the third number.

For some applications, as shown in FIG. 20, implantable structure 22 is implanted with contracting mechanism 28 disposed near left fibrous trigone 142, while for other applications (not shown, but similar to the arrangement shown in FIG. 7B), implantable structure 22 is implanted with contracting mechanism 28 disposed near right fibrous trigone 144.

Figure 21:
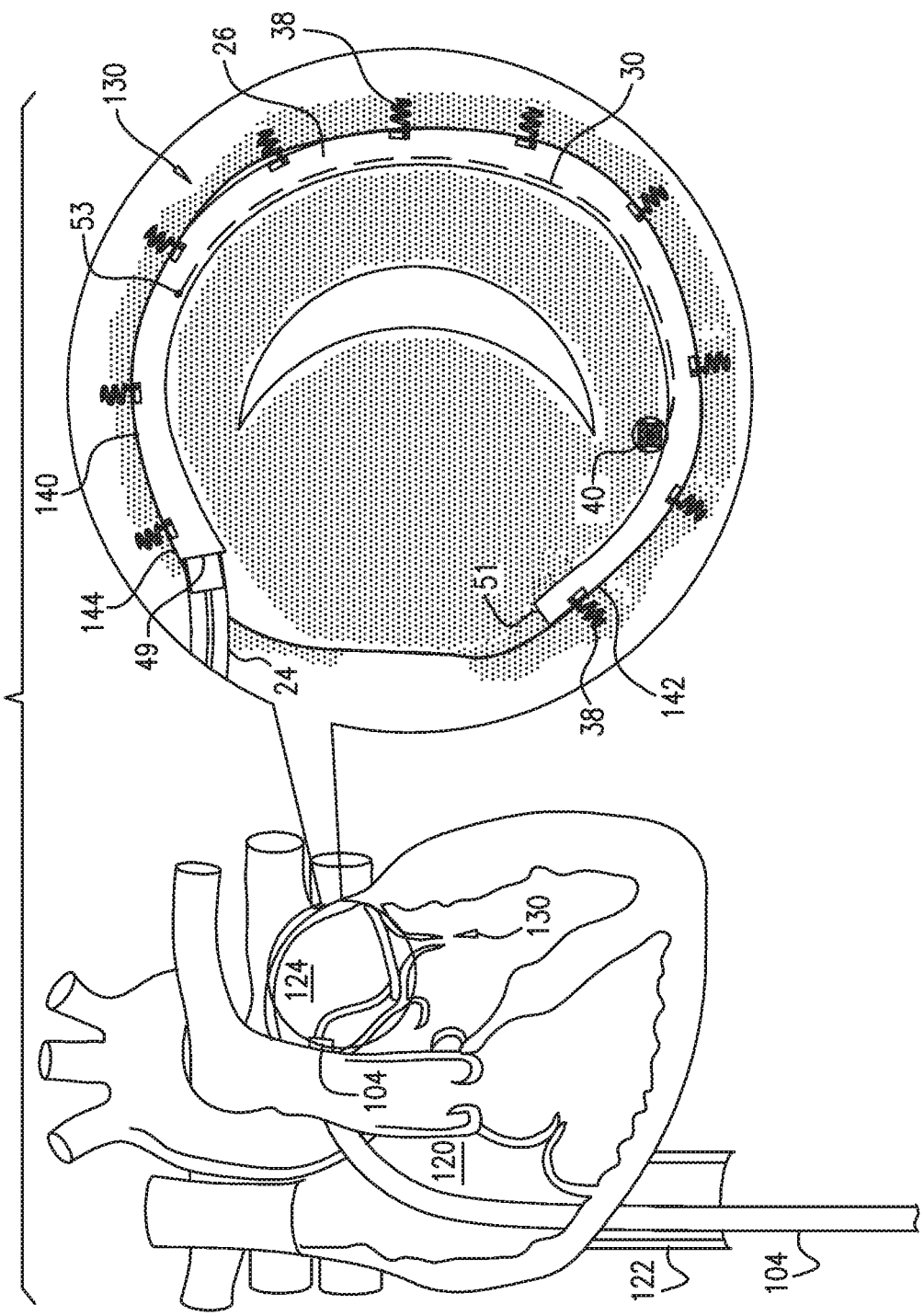
FIG. 21 is a schematic illustration of still another configuration of the implantable structure of FIG. 1 implanted around the mitral valve, in accordance with an application of the present invention.

Reference is now made to FIG. 21, which is a schematic illustration of implantable structure 22 after implantation around the annulus of mitral valve 130, in accordance with an application of the present invention. FIG. 21 shows the annulus before a longitudinal portion of sleeve 26 has been contracted, as described below. The techniques described with reference to FIG. 21 may optionally be used in combination with the techniques described hereinabove with reference to FIG. 19, and/or the techniques described hereinabove with reference to FIG. 20.

In this configuration, flexible sleeve 26 is placed at least partially around an annulus of mitral valve 130, such as partially around the annulus, as shown in FIG. 21, or entirely around the annulus in a closed loop, such as shown in FIG. 4, 5, 7A-B, 10, 16A-B, 17, or 18B, optionally using any of the techniques described with reference to these figures. For some applications in which the sleeve is placed entirely around the annulus, sleeve 26 is introduced into left atrium 124 while first and second sleeve ends are not coupled to each other; thereafter, in the left atrium, sleeve 26 is arranged entirely around the annulus to form the closed loop.

Sleeve 26 is fastened to the annulus by coupling a plurality of tissue anchors 38 to the annulus, including tissue anchors 38J and 38K, such that:
  a first set 324 of exactly three of tissue anchors 38J is disposed in succession along a first portion of longitudinal contracting member 30 with a first distance D9 between longitudinal-end tissue anchors of first set 324, measured along the annulus, and
  a second set 328 of exactly three of tissue anchors 38K is disposed in succession along a second portion of longitudinal contracting member 30 with a second distance D10 between longitudinal-end tissue anchors of second set 328, measured along the annulus,
  First distance D9 equals at least twice second distance D10, such as at least 2.5 times second distance D10, e.g., at least 3 times second distance D10. First distance D9 is measured between closest portions of the longitudinal-end tissue anchors of first set 324, and second distance D10 is measured between closest portions of the longitudinal-end tissue anchors of second set 328. First and second sets 324 and 328 do not share any common tissue anchors 38. Typically, the plurality of tissue anchors 38 comprises additional tissue anchors other than tissue anchors 38J and 38K. After the tissue anchors are fastened to the annulus, a longitudinal portion of sleeve 26 is contracted by causing the longitudinal contracting member to apply a force to the longitudinal portion of the sleeve, such as by actuating contracting assembly 40. Providing the greater number of anchoring points with second set 328 better distributes forces among the anchors of this set.

For some applications, as shown in FIG. 21, implantable structure 22 is implanted with contracting mechanism 28 disposed near left fibrous trigone 142, while for other applications (not shown, but similar to the arrangement shown in FIG. 7B), implantable structure 22 is implanted with contracting mechanism 28 disposed near right fibrous trigone 144.

Reference is now made to FIGS. 22A-D, which are schematic illustrations of another configuration of system 20 for repairing a dilated atrioventricular valve, and a method for deploying the system, in accordance with an application of the present invention. This configuration may be used in combination with any of the techniques and configurations described herein with reference to FIGS. 1, 2A-I, 3, 19, 20, 21, 24, 25A-B, and/or 26.

In this configuration, system 20 further comprises a linking bridge element 200, which is configured to be coupled to sleeve 26 in order to link first and second sleeve ends 51 and 49 of sleeve 26 of implantable structure 22 via linking bridge element 200. To this end, linking bridge element 200 typically comprises first and second bridge coupling interfaces 210A and 210B, which are configured to be coupled to corresponding first and second sleeve coupling interfaces 212A and 212B of sleeve 26, which are disposed within 1.5 cm of first and second sleeve ends 51 and 49, respectively, measured when the sleeve is fully longitudinally extended, such as at first and second sleeve ends 51 and 49, respectively. For example, first and second bridge coupling interfaces 210A and 210B may comprise female interfaces (as shown), and first and second sleeve coupling interfaces 212A and 212B may comprise male interfaces (as shown), which are configured to snap into the female interfaces. Alternatively, first and second sleeve coupling interfaces 212A and 212B may comprise female interfaces, such as rings (e.g., comprising a metal or a plastic) integrated into the wall of sleeve 26 (configurations not shown), and first and second bridge coupling interfaces 210A and 210B may comprise male interfaces (configuration not shown), which are configured to snap into the female interfaces. Further alternatively, the interfaces comprise other coupling structures, as is known in the art, such as coupling structures that snap together.

Typically, linking bridge element 200 has a length of at least 1 cm, no more than 5 cm, and/or between 1 and 5 cm, such as at least 1.5 cm, no more than 3.5 cm, and/or between 1.5 and 3.5 cm, e.g., 2 cm. Typically, first and second bridge coupling interfaces 210A and 210B are disposed within 1 cm (such as within 0.5 cm) of first and second ends 216A and 216B of linking bridge element 200, respectively, e.g., between 0.5 cm and 1 cm of first and second ends 216A and 216B of linking bridge element 200, respectively. For some applications, linking bridge element 200 comprises a metal or a polymer that provides longitudinal stability while maintaining some flexibility in other directions. Optionally, linking bridge element 200 further comprises a fabric or other coating for tissue growth enhancement. For some applications, linking bridge element 200 comprises elongated radial-force application element 482, such as described hereinabove with reference to FIGS. 9-15 and/or 17.

For some applications, system 20 comprises first and second flexible longitudinal guide members 214A and 214B, which are removably coupled to sleeve 26 within 1.5 cm of first and second sleeve ends 51 and 49 (e.g., with 0.5 cm of the sleeve ends, or at the sleeve ends), respectively, measured when the sleeve is fully longitudinally extended. First and second flexible longitudinal guide members 214A and 214B extend from first and second sleeve ends 51 and 49, respectively, away from sleeve 26. First and second flexible longitudinal guide members 214A and 214B may be directly or indirectly coupled to sleeve 26. For configurations in which first and second flexible longitudinal guide members 214A and 214B are indirectly coupled to sleeve 26, the longitudinal guide members may be coupled to respective intermediary elements at locations beyond the end of the sleeve (but still within 1.5 cm of the respective sleeve ends). For example, first and second flexible longitudinal guide members 214A and 214B may be (a) removably coupled to first and second sleeve coupling interfaces 212A and 212B, respectively (in which case the longitudinal guide members may be indirectly coupled to the sleeve), and/or (b) the wall of sleeve 26 (in which case the longitudinal guide members are directly coupled to the sleeve). For example, first and second flexible longitudinal guide members 214A and 214B may comprise respective sutures, wires, or strings.

Figure 22A:
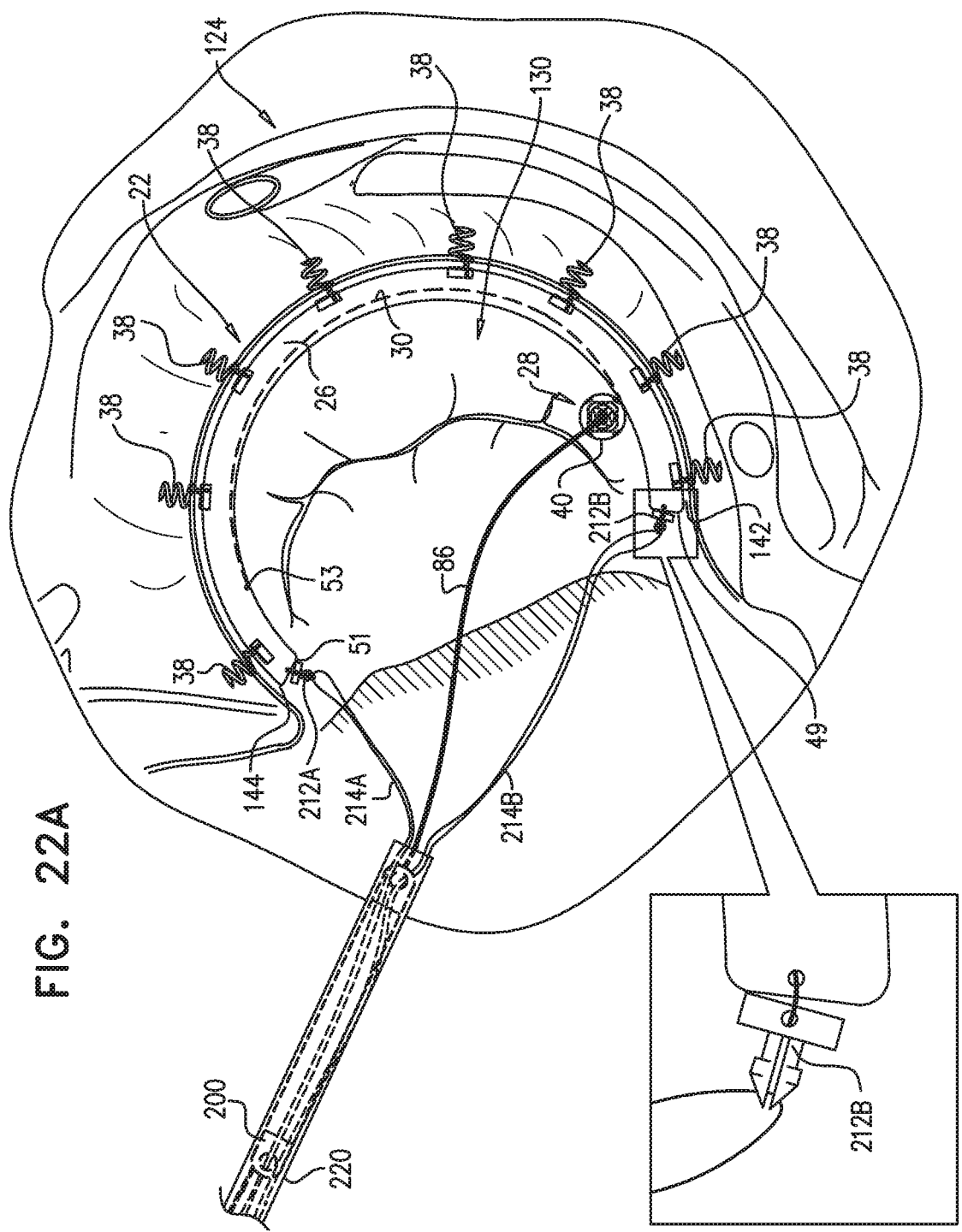
FIGS. 22A-D are schematic illustrations of another system for repairing a dilated atrioventricular valve, and a method for deploying the system, in accordance with an application of the present invention.
Figure 22B:
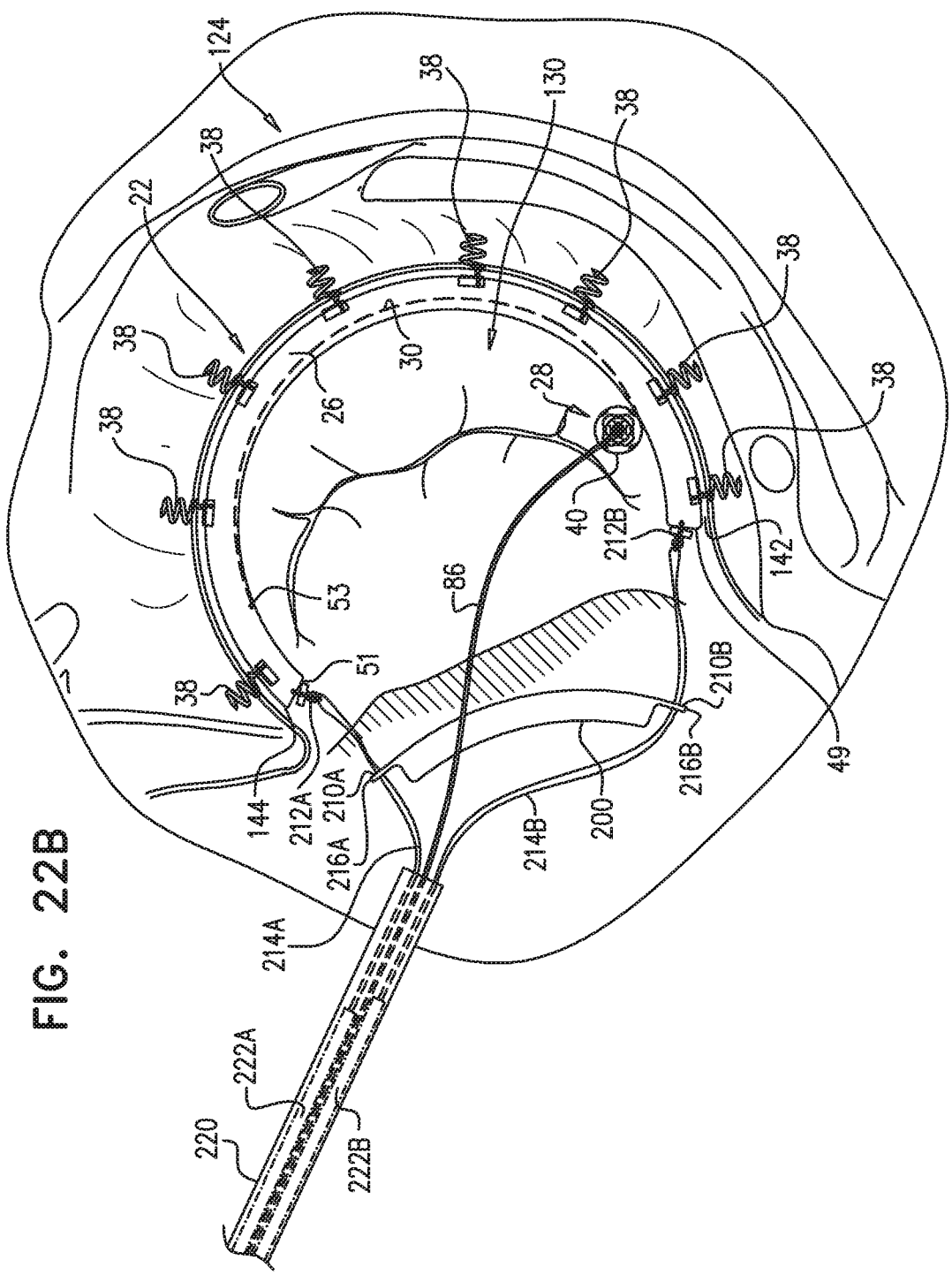
Figure 22C:
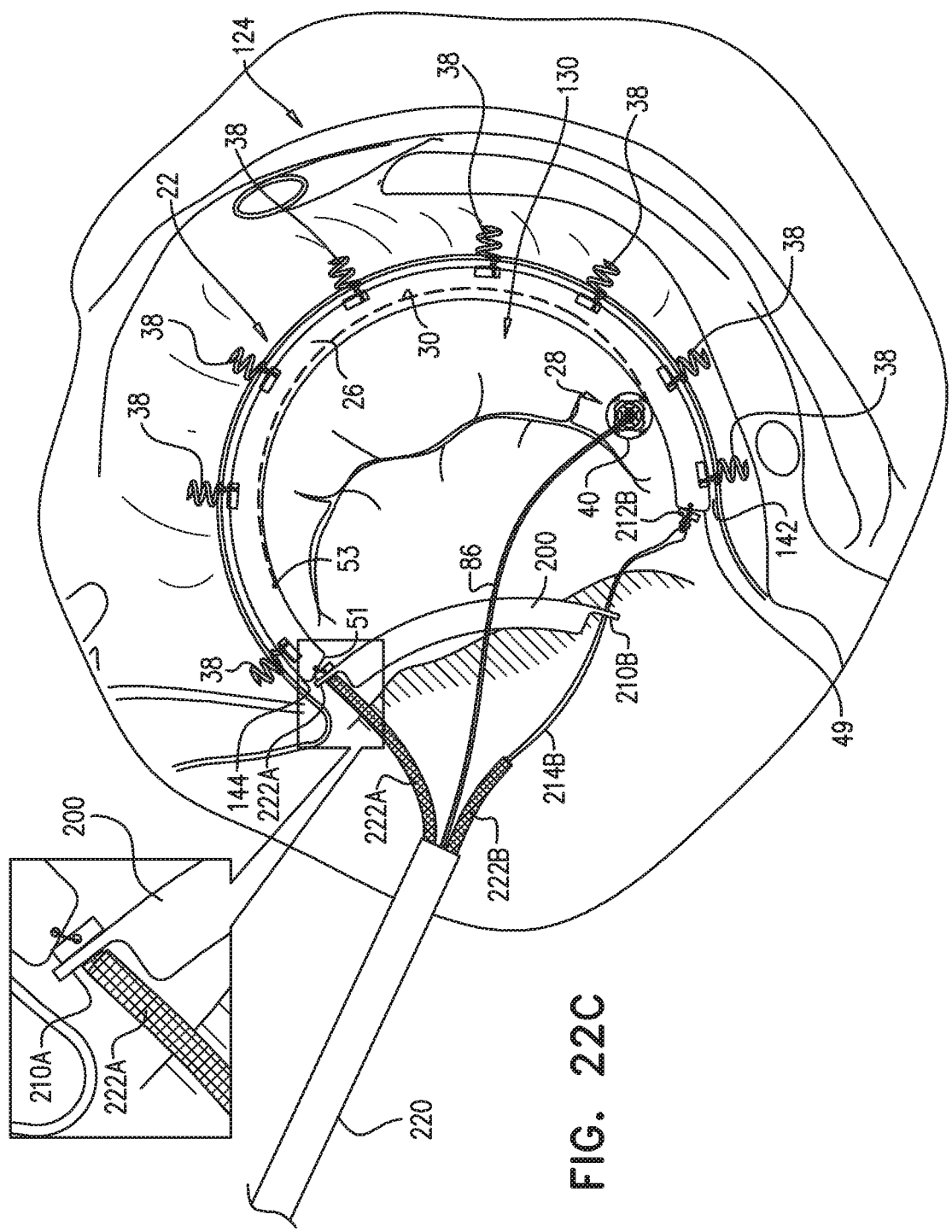

The longitudinal guide members are configured to guide first and second bridge coupling interfaces 210A and 210B to corresponding locations on sleeve 26, such as first and second sleeve coupling interfaces 212A and 212B, during an implantation procedure, as shown in FIGS. 22A-C. The longitudinal guide members removably pass through respective openings defined by linking bridge element 200, and then through a delivery tube 220 in which linking bridge element 200 is disposed for delivery to the atrium. For some applications, the respective openings are defined by first and second bridge coupling interfaces 210A and 210B, respectively (as shown). For other applications, the respective openings are located elsewhere on linking bridge element 200, typically within 10 mm, such as within 5 mm, of first and second bridge coupling interfaces 210A and 210B, respectively. (Optionally, longitudinal member 86, described hereinabove with reference to FIG. 21, also passes through delivery tube 220.)

For some applications, each of the longitudinal guide members is doubled over and threaded through its respective sleeve coupling interface and/or sleeve end. After the linking bridge element has been coupled to sleeve 26 of implantable structure 22, the longitudinal guide members are removed by pulling on one end of each of the longitudinal guide members, typically from outside of the patient's body. Alternatively, each of the longitudinal guide members is decoupled from the sleeve in some other manner, such as using techniques described in the above-mentioned '604 application for decoupling longitudinal member 86 from contracting mechanism 40.

Typically, as described hereinabove, implantable structure 22 comprises longitudinal contracting member 30, which is configured to longitudinally contract a longitudinal portion of sleeve 26, as described hereinabove. Longitudinal contracting member 30 may be disposed with respect to the sleeve in any of the arrangements described hereinabove, including those regarding the extent to which the contracting member extends along the length of sleeve. First and second flexible longitudinal guide members 214A and 214B are separate and distinct from longitudinal contracting member 30; in other words, first and second flexible longitudinal guide members 214A and 214B are not fixed to longitudinal contracting member 30, and are not parts of a common longitudinal member.

Typically, when first and second flexible longitudinal guide members 214A and 214B are removably coupled to sleeve 26 of implantable structure 22:
- no portion of either first flexible longitudinal guide member 214A or second flexible longitudinal guide member 214B is disposed more than 1.5 cm from first and second sleeve ends 51 and 49, respectively, measured when the sleeve is fully longitudinally extended;
- first and second flexible longitudinal guide members 214A and 214B are collectively disposed along less than 30% of a length of sleeve 26, such as less than 5% of the length of the sleeve, measured when the sleeve is fully longitudinally extended; and/or
- for applications in which implantable structure 22 comprises longitudinal contracting member 30, first and second flexible longitudinal guide members 214A and 214B do not longitudinally overlap longitudinal contracting member 30 (i.e., are not disposed at any common longitudinal locations with longitudinal contracting member 30).

Alternatively, for some applications, system 20 comprises a single flexible longitudinal guide member 214 which removably passes through the entire sleeve 26 (configuration not shown). After the linking bridge element has been coupled to sleeve 26 of implantable structure 22, the longitudinal guide member is removed by pulling on one end of the longitudinal guide member, typically from outside of the patient's body. Alternatively, the longitudinal guide member is decoupled from the sleeve in some other manner, such as using techniques described in the above-mentioned '604 application for decoupling longitudinal member 86 from contracting mechanism 40.

After first and second bridge coupling interfaces 210A and 210B have been guided over first and second flexible longitudinal guide members 214A and 214B to corresponding first and second sleeve coupling interfaces 212A and 212B, as shown in FIGS. 22A-C, first and second bridge coupling interfaces 210A and 210B are coupled to corresponding first and second sleeve coupling interfaces 212A and 212B, also as shown in FIG. 24C. For example, first and second tubes 222A and 222B may be introduced through delivery tube 220 and over first and second flexible longitudinal guide members 214A and 214B, respectively, and used to push the corresponding coupling interfaces against each other, until they snap together, as shown in FIG. 22C.

Figure 22D:
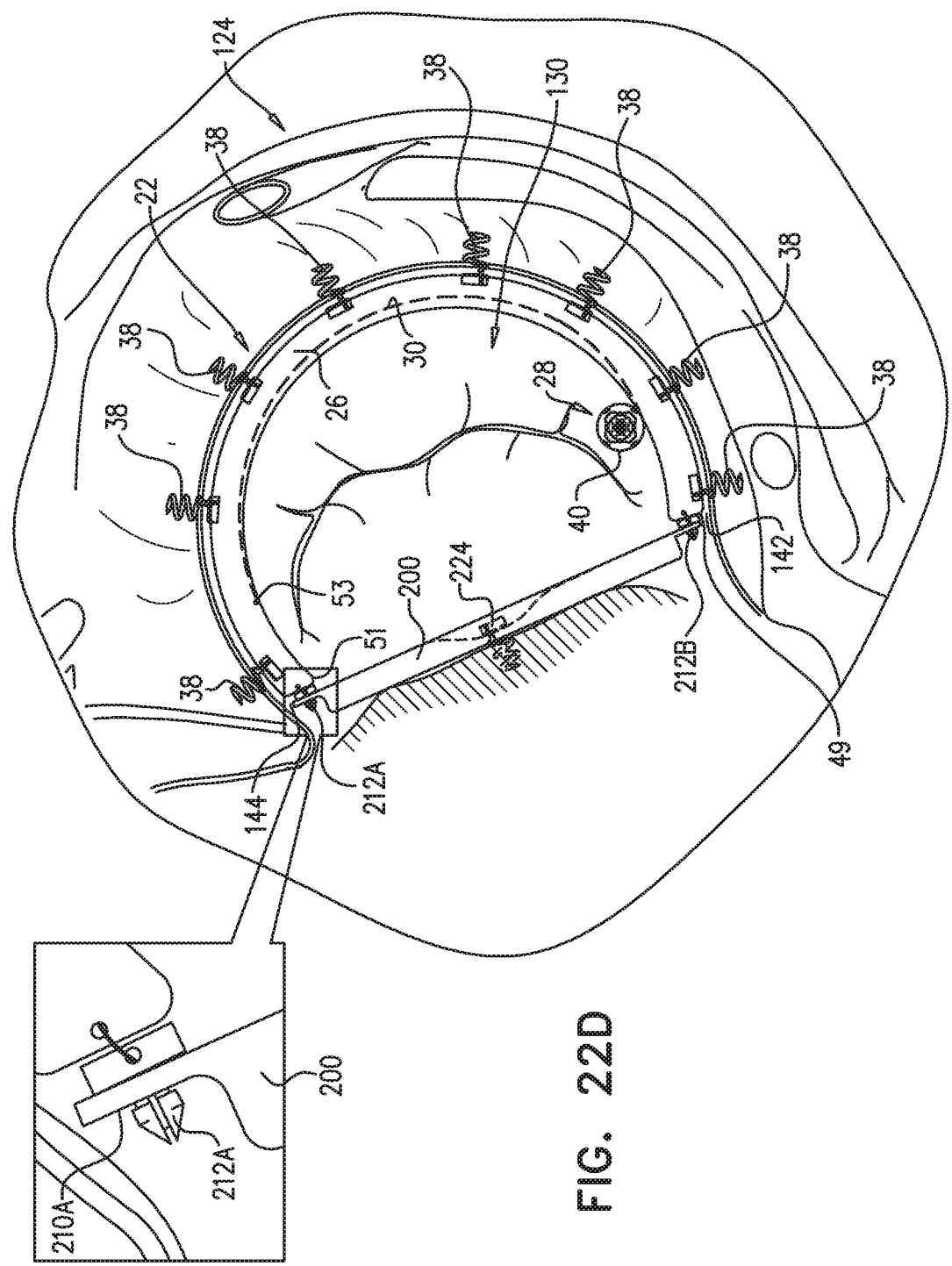

FIG. 22D shows linking bridge element 200 coupled to sleeve 26 of implantable structure 22, after the delivery tool has been removed from the atrium.

For applications in which implantable structure 22 comprises longitudinal contracting member 30, the implantation method typically comprises:

during a percutaneous transcatheter procedure, placing sleeve 26 of implantable structure 22 partially around an annulus of a valve of a subject, such as a mitral valve or tricuspid valve (typically around all or a portion of a posterior portion of the annulus between fibrous trigones of the valve);

anchoring sleeve 26 to cardiac tissue, such as described hereinabove with reference to FIGS. 2G-I;

coupling linking bridge element 200 to sleeve 26, as described hereinabove, typically along all or a portion of an anterior portion of the annulus between the fibrous trigones; and thereafter, contracting a longitudinal portion of sleeve 26 by causing longitudinal contracting member 30 to apply a contracting force to the longitudinal portion of the sleeve, as described hereinabove.

Thus, the contracting of the sleeve is not performed simultaneously with the coupling of the linking bridge element to the sleeve. Moreover, longitudinal contracting member 30 does not serve as either of first and second flexible longitudinal guide members 214A and 214B.

Optionally, for some applications, system 20 comprises one or more bridge anchors 224 (e.g., one, two, or three bridge anchors 224), which are used to couple linking bridge element 200 to tissue at the anterior portion of the annulus. For some applications, the one or more bridge anchors 224 are deployed using anchor deployment manipulator 24, described hereinabove.

Figure 23A:
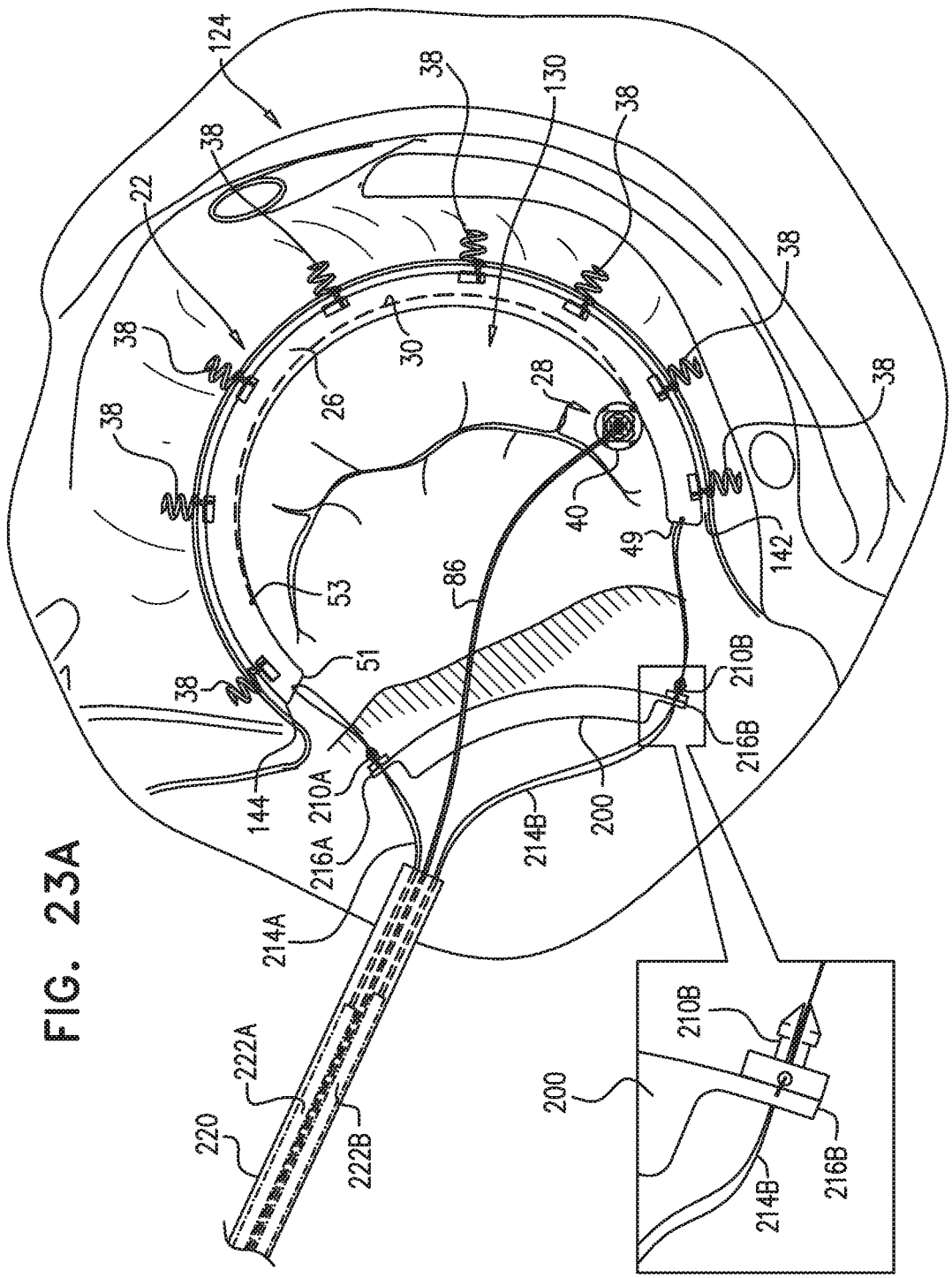
FIGS. 23A-B are schematic illustrations of another configuration of a linking bridge element of the system of FIGS. 22A-D, in accordance with an application of the present invention.
Figure 23B:
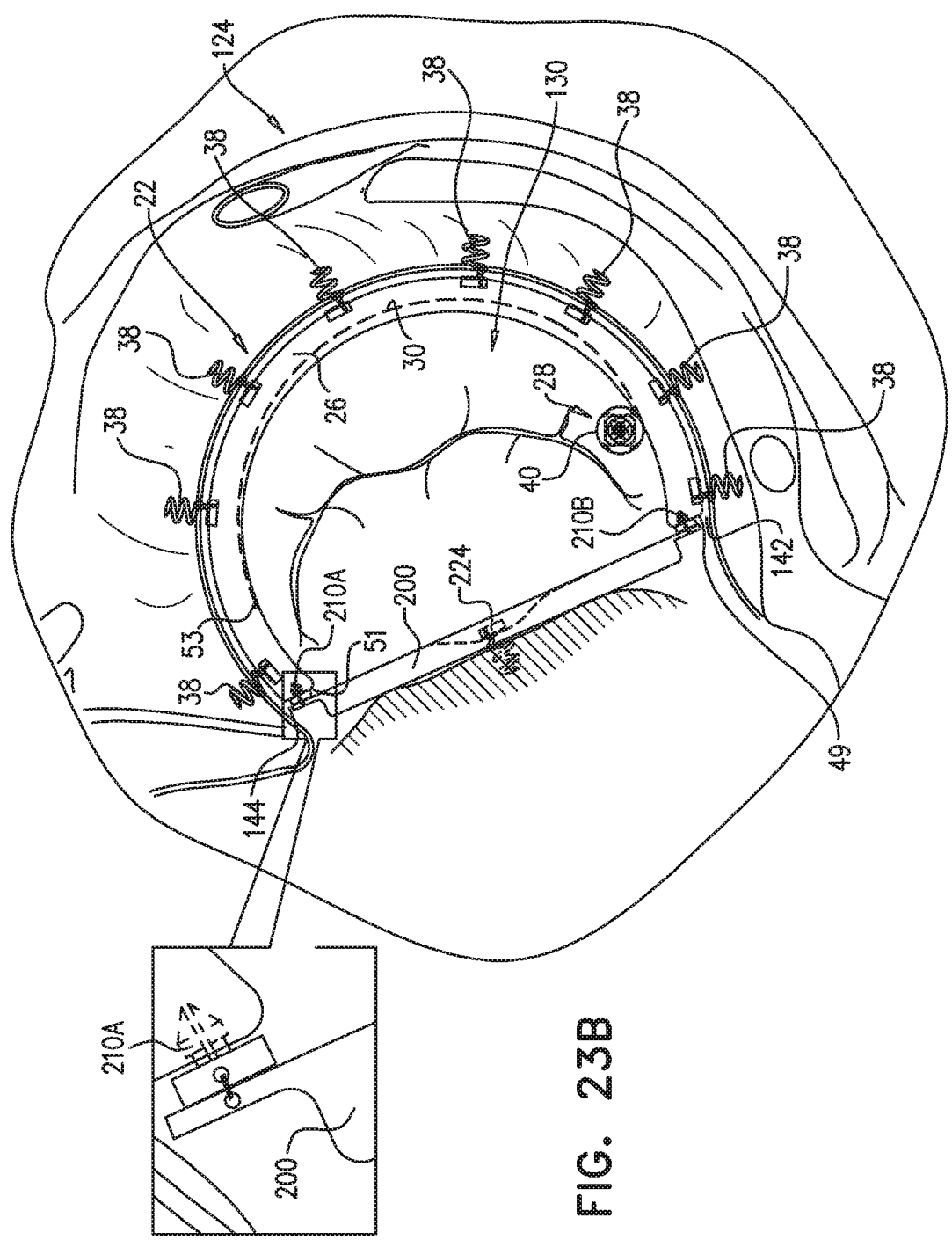

Reference is now made to FIGS. 23A-B, which are schematic illustrations of another configuration of linking bridge element 200, in accordance with an application of the present invention. Other than as described below, this configuration is identical to the configuration described hereinabove with reference to FIGS. 22A-D.

In this configuration, first and second bridge coupling interfaces 210A and 210B are male interfaces, which are configured to pierce the wall of sleeve 26, thereby becoming coupled to the sleeve. For example, the coupling elements may be shaped as harpoons or other barbed structures. In this configuration, sleeve 26 typically does not comprise any coupling interfaces or coupling elements.

Figure 24:
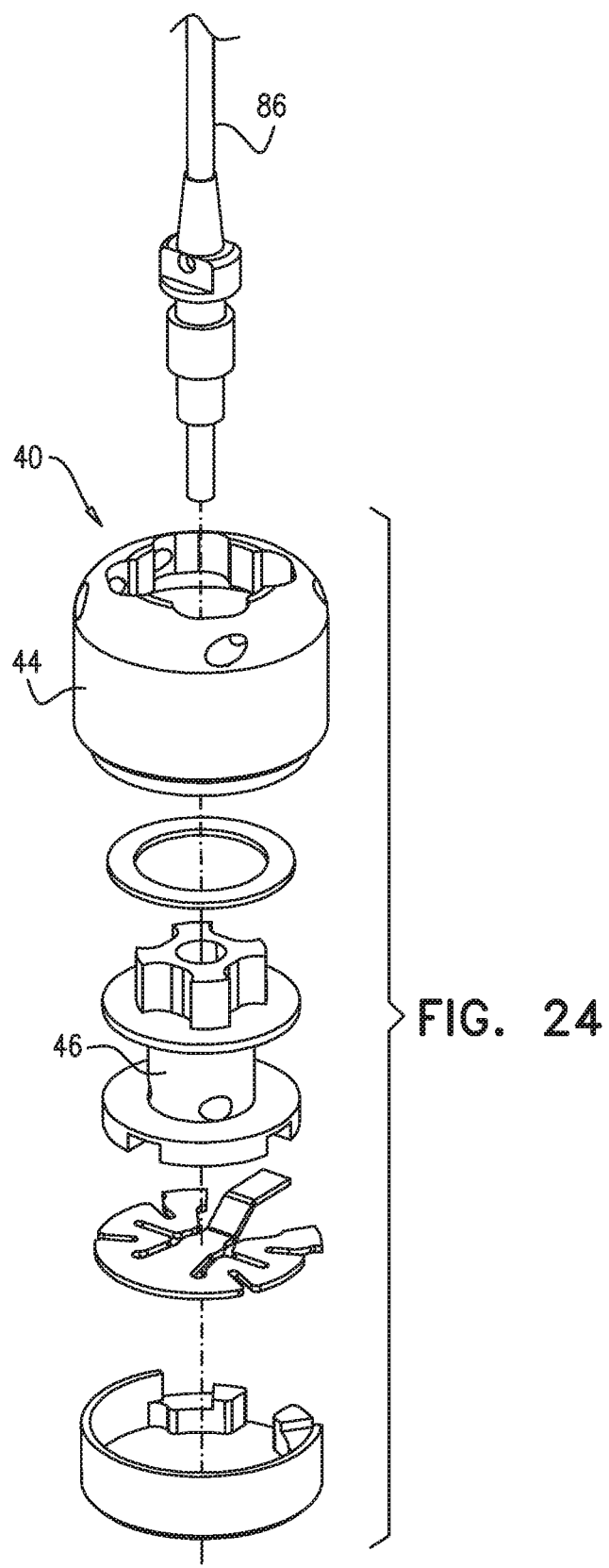
FIG. 24 is a schematic illustration of a contracting mechanism, disassembled to show a relationship among individual components of the contracting mechanism, in accordance with an application of the present invention.

Reference is now made to FIG. 24, which is a schematic illustration of contracting mechanism 28, disassembled to show a relationship among individual components of the contracting mechanism, in accordance with an application of the present invention. The components are arranged and function as described with reference to FIG. 7 of the above-mentioned '604 publication, mutatis mutandis.

Figure 25A:
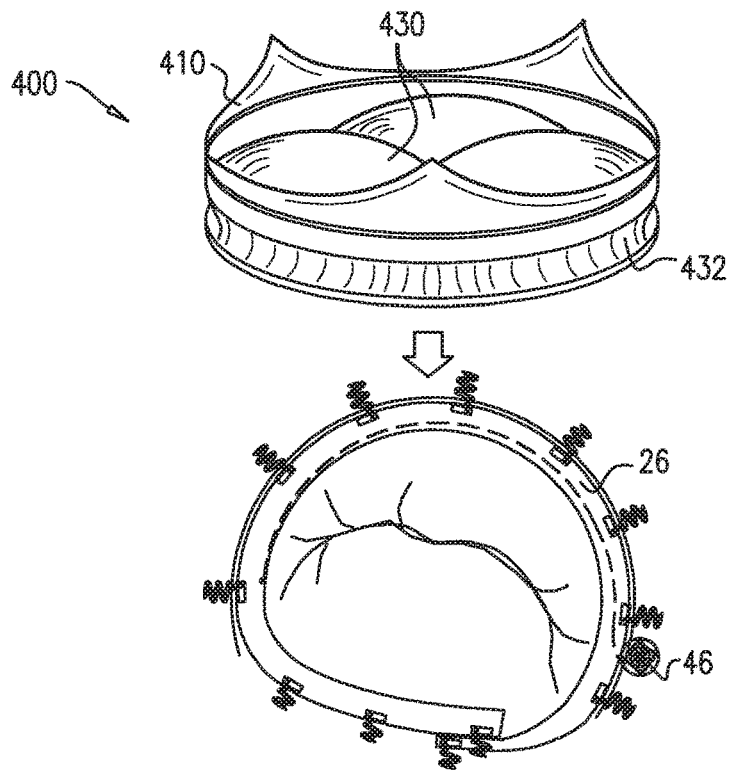
FIGS. 25A-B and 26 are schematic illustrations of a valve prosthesis assembly, in accordance with respective applications of the present invention.
Figure 25B:
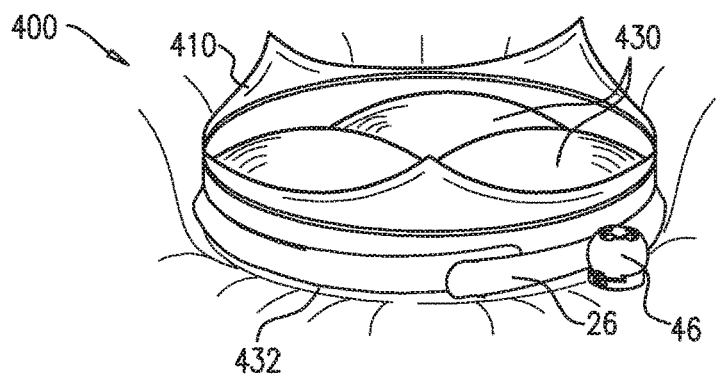
Figure 26:
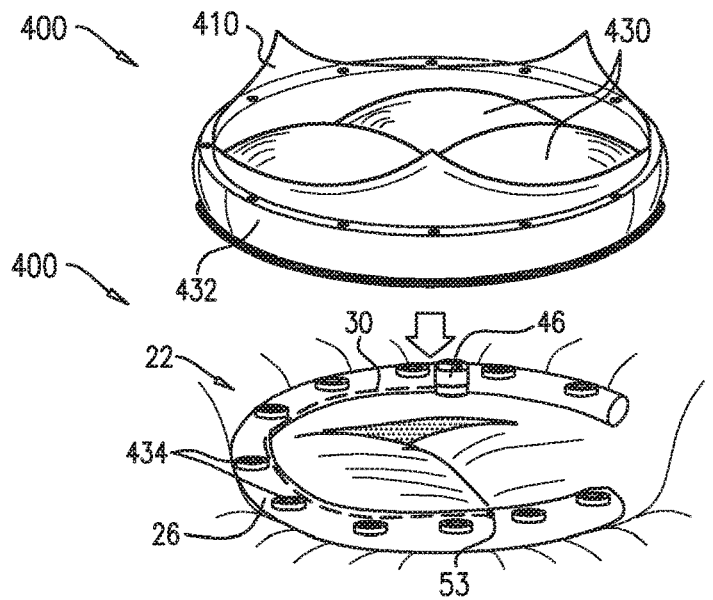

Reference is made to FIGS. 25A-B and 26, which are schematic illustrations of a valve prosthesis assembly 400, in accordance with respective applications of the present invention. Valve prosthesis assembly 400 comprises a prosthetic heart valve 410 that is couplable to a base ring 422. Prosthetic heart valve 410 is used to replace a native diseased heart valve. Valve 410 comprises a plurality of artificial leaflets 430, which comprise a pliant material. Valve 410 may implement techniques known in the artificial valve art, such as described, for example, in US Patent Application Publication 2007/0255400 to Parravicini et al., US Patent Application Publication 2004/0122514 to Fogarty et al., US Patent Application Publication 2007/0162111 to Fukamachi et al., and/or US Patent Application Publication 2008/0004697 to Lichtenstein et al., all of which are incorporated herein by reference.

Valve 410 further comprises an annular base 432, to which artificial leaflets 430 are coupled. Annular base 432 is configured to be couplable to base ring 422 during an implantation procedure. For example, as shown in FIG. 26, base ring 422 may comprise one or more coupling elements 434, such as clips or magnets, which are configured to be coupled to corresponding coupling elements on a lower surface of annular base 432 (not visible in the figures). Alternatively or additionally, annular base 432 may be configured to be placed within the opening defined by base ring 422, as shown in FIG. 25A. To hold the annular base coupled to the base ring, the base ring is tightened around the annular base, as shown in FIG. 25B, typically using one or more of the techniques described hereinabove for contracting implantable structures. Typically, valve prosthesis assembly 400, such as annular base 432 thereof, is configured to push and hold open the intact diseased native leaflets.

Base ring 422 implements one or more of the techniques of implantable structure 22 described hereinabove. In particular, base ring 422 may be coupled to the annulus of the native diseased valve using the anchoring techniques described hereinabove. In addition, base ring 422 typically comprises sleeve 26 and contracting mechanism 28, which may, for some applications, comprise a rotatable structure, such as a spool 46, which is typically implemented using techniques described herein. The contracting mechanism is arranged to contract base ring 422, e.g., the rotatable structure is arranged such that rotation thereof contracts base ring 422, typically using techniques described herein. Such tightening may serve to couple base ring 422 to annular base 432, as shown in FIG. 25B. Alternatively or additionally, such tightening sets the desired dimensions of the base ring, in order to align the coupling elements of the base ring with those of valve 410, thereby enabling tight coupling, such as for the applications described with reference to FIG. 26.

For some applications, as shown in FIG. 26, base ring 422 comprises a partial ring, such as described hereinabove with reference to FIGS. 2A-I, 19, 20, and 21. For other applications, as shown in FIGS. 25A-B, the base ring is arranged as a full ring, such as described hereinabove with reference to FIGS. 4, 5, 7A-B, 10, 16A-B, 17, and 18B.

Valve prosthesis assembly 400 is typically implanted in a minimally invasive transcatheter or percutaneous procedure. The procedure begins with the introduction and implantation of base ring 422 into the heart, such as using techniques for implanting implantable structure 22, described hereinabove with reference to FIGS. 2A-I. Prosthetic heart valve 410 is subsequently introduced into the heart and coupled to base ring 422, as described above. Valve prosthesis assembly 400 is typically used for replacement of a diseased native mitral valve, aortic valve, tricuspid valve, or pulmonary valve.

For some applications, system 20 further comprises a closure mechanism, such as described in above-mentioned US Patent Application Publication 2012/0330411, with reference to FIGS. 16-17B thereof.

For some applications, system 20 further comprises a flexible pusher element, such as described and shown in US Patent Application Publication 2010/0286767, which is incorporated herein by reference, with reference to FIG. 8 thereof. The pusher element aids with accurately positioning successive anchors 38 during an implantation procedure, such as described hereinabove with reference to FIGS. 2H and 21. For some applications, system 20 further comprises a pusher tube that is applied to proximal end 49 of sleeve 26, such as described in the above-mentioned '604 publication, with reference to FIGS. 14 and/or 18A-B thereof. For some applications, system 20 further comprises a steerable tube, such as described in the above-mentioned '604 publication, with referenced to FIG. 15 thereof, or with reference to FIG. 16 thereof. For some applications, system 20 further comprises a pulling wire, such as described in the above-mentioned '604 publication, with referenced to FIG. 17 thereof. For some applications, system 20 further comprises an external control handle, such as described in the above-mentioned '604 publication, with referenced to FIG. 19 thereof. For some applications, contracting assembly 40 and implantable structure 22 are configured as described with reference to FIG. 23 of the above-mentioned '604 publication, mutatis mutandis.

For some applications of the present invention, system 20 is used to treat an atrioventricular valve other than the mitral valve, i.e., the tricuspid valve. For these applications, implantable structure 22 and other components of system 20 described hereinabove as being placed in the left atrium are instead placed in the right atrium.

Although implantable structure 22 is described hereinabove as being placed in an atrium, for some application the implantable structure is instead placed in either the left or right ventricle.

The scope of the present invention includes applications described in the following applications, which are incorporated herein by reference. In an application, techniques and apparatus described in one or more of the following applications are combined with techniques and apparatus described herein:

PCT Publication WO 06/097931 to Gross et al., entitled, "Mitral Valve treatment techniques," filed Mar. 15, 2006;

U.S. Provisional Patent Application 60/873,075 to Gross et al., entitled, "Mitral valve closure techniques," filed Dec. 5, 2006;

U.S. Provisional Patent Application 60/902,146 to Gross et al., entitled, "Mitral valve closure techniques," filed on Feb. 16, 2007;

U.S. Provisional Patent Application 61/001,013 to Gross et al., entitled, "Segmented ring placement," filed Oct. 29, 2007;

PCT Patent Application PCT/IL07/001503 to Gross et al., entitled, "Segmented ring placement," filed on Dec. 5, 2007, which published as PCT Publication WO 08/068756;

U.S. patent application Ser. No. 11/950,930 to Gross et al., entitled, "Segmented ring placement," filed on Dec. 5, 2007, which published as US Patent Application Publication 2008/0262609;

U.S. Provisional Patent Application 61/132,295 to Gross et al., entitled, "Annuloplasty devices and methods of delivery therefor," filed on Jun. 16, 2008;

U.S. patent application Ser. No. 12/341,960 to Cabiri, entitled, "Adjustable partial annuloplasty ring and mechanism therefor," filed on Dec. 22, 2008, which published as US Patent Application Publication 2010/0161047;

U.S. Provisional Patent Application 61/207,908 to Miller et al., entitled, "Actively-engageable movement-restriction mechanism for use with an annuloplasty structure," filed on Feb. 17, 2009;

U.S. patent application Ser. No. 12/435,291 to Maisano et al., entitled, "Adjustable repair chords and spool mechanism therefor," filed on May 4, 2009, which published as US Patent Application Publication 2010/0161041;

U.S. patent application Ser. No. 12/437,103 to Zipory et al., entitled, "Annuloplasty ring with intra-ring anchoring," filed on May 7, 2009, which published as US Patent Application Publication 2010/0286767;

PCT Patent Application PCT/IL2009/000593 to Gross et al., entitled, "Annuloplasty devices and methods of delivery therefor," filed on Jun. 15, 2009, which published as PCT Publication WO 10/004546;

U.S. patent application Ser. No. 12/548,991 to Maisano et al., entitled, "Implantation of repair chords in the heart," filed on Aug. 27, 2009, which published as US Patent Application Publication 2010/0161042;

U.S. patent application Ser. No. 12/608,316 to Miller et al., entitled, "Tissue anchor for annuloplasty ring," filed on Oct. 29, 2009, which published as US Patent Application Publication 2011/0106247;

U.S. Provisional Patent Application 61/265,936 to Miller et al., entitled, "Delivery tool for implantation of spool assembly coupled to a helical anchor," filed Dec. 2, 2009;

PCT Patent Application PCT/IL2009/001209 to Cabiri et al., entitled, "Adjustable annuloplasty devices and mechanisms therefor," filed on Dec. 22, 2009, which published as PCT Publication WO 10/073246;

U.S. patent application Ser. No. 12/689,635 to Zipory et al., entitled, "Over-wire rotation tool," filed on Jan. 19, 2010, which published as US Patent Application Publication 2010/0280604;

U.S. patent Ser. No. 12/689,693 to Hammer et al., entitled, "Deployment techniques for annuloplasty ring," filed on Jan. 19, 2010, which published as US Patent Application Publication 2010/0280605;

U.S. patent application Ser. No. 12/706,868 to Miller et al., entitled, "Actively-engageable movement-restriction mechanism for use with an annuloplasty structure," filed on Feb. 17, 2010, which published as US Patent Application Publication 2010/0211166;

PCT Patent Application PCT/IL2010/000357 to Maisano et al., entitled, "Implantation of repair chords in the heart," filed May 4, 2010, which published as PCT Publication WO 10/128502;

PCT Patent Application PCT/IL2010/000358 to Zipory et al., entitled, "Deployment techniques for annuloplasty ring and over-wire rotation tool," filed May 4, 2010, which published as PCT Publication WO 10/128503; and/or U.S. patent application Ser. No. 13/167,476 to Hammer et al., filed Jun. 23, 2011, entitled, "Closure element for use with an annuloplasty structure," which published as US Patent Application Publication 2012/0330410.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method for use with a plurality of tissue anchors, each of the tissue anchors having a respective anchor head, the method comprising:
   (1) during a percutaneous transcatheter procedure, securing an annuloplasty structure at least partially around an annulus of a mitral valve of a subject by coupling the plurality of tissue anchors of the annuloplasty structure to the annulus, such that (i) a longitudinal contracting member of the annuloplasty structure extends at least partially around the annulus, and (ii) the plurality of tissue anchors is distributed at least partially around the annulus, with:
      a first longitudinal density of the tissue anchors along a lateral scallop (P1) of a posterior leaflet of the mitral valve, which density is equal to (a) a number of the tissue anchors coupled to the annulus along the lateral scallop (P1) divided by (b) a length of the lateral scallop (P1) along the annulus,
      a second longitudinal density of the tissue anchors along a middle scallop (P2) of the posterior leaflet, which density is equal to (a) a number of the tissue anchors coupled to the annulus along the middle scallop (P2) divided by (b) a length of the middle scallop (P2) along the annulus, and
      a third longitudinal density of the tissue anchors along a medial scallop (P3) of the posterior leaflet, which density is equal to (a) a number of the tissue anchors coupled to the annulus along the medial scallop (P3) divided by (b) a length of the medial scallop (P3) along the annulus, wherein the second longitudinal density is at least twice as great as at least one of the following: (a) the first longitudinal density, and (b) the third longitudinal density; and
   (2) thereafter, contracting at least part of the annulus by contracting a longitudinal portion of the annuloplasty structure by tightening the longitudinal contracting member, the second longitudinal density being sufficiently great that the tightening causes contact between adjacent anchor heads of at least two of the anchors coupled to the annulus along the middle scallop.

2. The method according to claim 1, wherein the annuloplasty structure includes a locking mechanism, and wherein the method further comprises, after step (2), locking the longitudinal contracting member with respect to the locking mechanism.

3. The method according to claim 2, wherein the annuloplasty structure includes a contracting assembly, and wherein the tightening, in step (2), of the longitudinal contracting member comprises tightening the longitudinal contracting member by actuating the contracting assembly.

4. The method according to claim 1, wherein both (a) the second longitudinal density is at least twice the first longitudinal density, and (b) the second longitudinal density is at least twice the third longitudinal density.

5. The method according to claim 1, wherein the coupling, in step (1), of the plurality of tissue anchors to the annulus comprises coupling the plurality of tissue anchors to the annulus such that, before step (2), the adjacent anchor heads of the at least two of the anchors do not touch.

6. The method according to claim 1, wherein the coupling, in step (1), of the plurality of tissue anchors to the annulus comprises coupling the plurality of tissue anchors to the annulus such that, after step (2), (a) none of the anchor heads of the tissue anchors coupled along the lateral scallop (P1) touches any of the other anchor heads of the tissue anchors, and (b) none of the anchor heads of the tissue anchors coupled along the medial scallop (P3) touches any of the other anchor heads of the tissue anchors.

7. The method according to claim 1, wherein the coupling, in step (1), of the plurality of tissue anchors to the annulus comprises coupling the plurality of tissue anchors to the annulus such that, after step (2), (a) a first number of the anchor heads of the tissue anchors coupled along the lateral scallop (P1) touch at least one longitudinally-adjacent anchor head, and (b) a second number of the anchors heads of the tissue anchors coupled along the middle scallop (P2) touch at least one longitudinally-adjacent anchor head, the second number greater than the first number.

8. The method according to claim 1, wherein the coupling, in step (1), of the plurality of tissue anchors to the annulus comprises coupling the plurality of tissue anchors to the annulus such that, after step (2), (a) a second number of the anchor heads of the tissue anchors coupled along the middle scallop (P2) touch at least one longitudinally-adjacent anchor head, and (b) a third number of the anchors heads of the tissue anchors coupled along the medial scallop (P3) touch at least one longitudinally-adjacent anchor head, the second number greater than the third number.

9. The method according to claim 1, wherein the coupling, in step (1), of the plurality of tissue anchors to the annulus comprises coupling the plurality of tissue anchors to the annulus such that, after step (2): a first number of the anchor heads of the tissue anchors coupled along the lateral scallop (P1) touch at least one longitudinally-adjacent anchor head, a second number of the anchors heads of the tissue anchors coupled along the middle scallop (P2) touch at least one longitudinally-adjacent anchor head, and a third number of the anchors heads of the tissue anchors coupled along the medial scallop (P3) touch at least one longitudinally-adjacent anchor head, the second number greater than the first number, and the second number greater than the third number.

10. The method according to claim 1, wherein the annuloplasty structure has first and second ends, and wherein the method comprises introducing the annuloplasty structure into a left atrium of the subject while the first and the second ends are not coupled to each other.

11. The method according to claim 10, wherein step (1) comprises securing the annuloplasty structure entirely around the annulus to form a closed loop, after the introducing of the annuloplasty structure into the left atrium while the first and the second ends are not coupled to each other.

12. The method according to claim 1, wherein the annuloplasty structure is shaped so as to define an integrally closed loop having no ends, and wherein the method comprises introducing, into a left atrium of the subject, the annuloplasty structure that is shaped so as to define the integrally closed loop having no ends.

13. A method comprising:
during a percutaneous transcatheter procedure, securing an annuloplasty structure at least partially around an annulus of a mitral valve of a subject by coupling a plurality of tissue anchors of the annuloplasty structure to the annulus, such that (i) a longitudinal contracting member of the annuloplasty structure extends at least partially around the annulus, and (ii) the plurality of tissue anchors is distributed at least partially around the annulus, with:
a first subset of the tissue anchors distributed along a lateral scallop (P1) of a posterior leaflet of the mitral valve,
a second subset of the tissue anchors distributed along a middle scallop (P2) of the posterior leaflet, and
a third subset of the tissue anchors distributed along a medial scallop (P3) of the posterior leaflet, wherein the anchors of the second subset are distributed at least twice as close to each other compared with the anchors of an other subset selected from the group consisting of the first subset, and the third subset; and
thereafter, contracting the annulus by drawing anchors of the plurality toward each other by tightening the longitudinal contracting member such that (i) proximity between anchors of the second subset obstructs the anchors of the second subset from being drawn toward each other, whereas (ii) proximity between anchors of the other subset facilitates the anchors of the other subset being drawn toward each other.

14. A method comprising:
during a percutaneous transcatheter procedure, securing an annuloplasty structure at least partially around an annulus of a mitral valve of a subject by coupling a plurality of tissue anchors of the annuloplasty structure to the annulus, such that (i) a longitudinal contracting member of the annuloplasty structure extends at least partially around the annulus, and (ii) the plurality of tissue anchors is distributed at least partially around the annulus, with:
a first subset of the tissue anchors distributed along a lateral scallop (P1) of a posterior leaflet of the mitral valve,
a second subset of the tissue anchors distributed along a middle scallop (P2) of the posterior leaflet, and
a third subset of the tissue anchors distributed along a medial scallop (P3) of the posterior leaflet, wherein the anchors of the second subset are distributed at least twice as close to each other compared with the anchors of an other subset selected from the group consisting of the first subset, and the third subset; and
thereafter, contracting the annulus by drawing anchors of the plurality toward each other by tightening the longitudinal contracting member such that contact between anchors of the second subset obstructs the anchors of the second subset from being drawn toward each other.

15. The method according to claim 13, wherein the annuloplasty structure includes a locking mechanism, and wherein the method further comprises, after the contracting of the annulus, locking the longitudinal contracting member with respect to the locking mechanism.

16. The method according to claim 13, wherein both (a) the anchors of the second subset are distributed at least twice as close to each other compared with the anchors of the first subset, and (b) the anchors of the second subset are distributed at least twice as close to each other compared with the anchors of the third subset.

17. The method according to claim 13, wherein at least one of either (a) the anchors of the second subset are distributed at least twice as close to each other compared with the anchors of the first subset, and (b) the anchors of the second subset are distributed at least twice as close to each other compared with the anchors of the third subset.

18. The method according to claim 13, wherein the coupling of the plurality of tissue anchors to the annulus comprises coupling at least 3 tissue anchors to the annulus along the middle scallop.

19. The method according to claim 13, wherein the annuloplasty structure has first and second ends, and wherein the method comprises introducing the annuloplasty structure into a left atrium of the subject while the first and the second ends are not coupled to each other.

20. The method according to claim 19, wherein the securing comprises securing the annuloplasty structure entirely around the annulus to form a closed loop, after the introducing of the annuloplasty structure into the left atrium while the first and the second ends are not coupled to each other.

21. The method according to claim 13, wherein the annuloplasty structure is shaped so as to define an integrally closed loop having no ends, and wherein the method comprises introducing, into a left atrium of the subject, the annuloplasty structure that is shaped so as to define the integrally closed loop having no ends.

22. The method according to claim 14, wherein the annuloplasty structure includes a locking mechanism, and wherein the method further comprises, after the contracting of the annulus, locking the longitudinal contracting member with respect to the locking mechanism.

23. The method according to claim 22, wherein the annuloplasty structure includes a contracting assembly, and wherein the tightening of the longitudinal contracting member comprises tightening the longitudinal contracting member by actuating the contracting assembly.

24. The method according to claim 14, wherein both (1) the anchors of the second subset are distributed at least twice as close to each other compared with the anchors of the first subset, and (2) the anchors of the second subset are distributed at least twice as close to each other compared with the anchors of the third subset.

25. The method according to claim 14, wherein at least one of (1) the anchors of the second subset are distributed at least twice as close to each other compared with the anchors of the first subset, and (2) the anchors of the second subset are distributed at least twice as close to each other compared with the anchors of the third subset.

26. The method according to claim 14, wherein the coupling of the plurality of tissue anchors to the annulus comprises coupling at least 3 tissue anchors to the annulus along the middle scallop.

27. The method according to claim 14, wherein the annuloplasty structure has first and second ends, and wherein the method comprises introducing the annuloplasty structure into a left atrium of the subject while the first and the second ends are not coupled to each other.

28. The method according to claim 27, wherein the securing comprises securing the annuloplasty structure entirely around the annulus to form a closed loop, after the introducing of the annuloplasty structure into the left atrium while the first and the second ends are not coupled to each other.

29. The method according to claim 14, wherein the annuloplasty structure is shaped so as to define an integrally closed loop having no ends, and wherein the method comprises introducing, into a left atrium of the subject, the annuloplasty structure that is shaped so as to define the integrally closed loop having no ends.

\* \* \* \* \*